US006719969B1

(12) United States Patent
Hogaboam et al.

(10) Patent No.: US 6,719,969 B1
(45) Date of Patent: Apr. 13, 2004

(54) TREATMENT OF LIVER DISEASE AND INJURY WITH CXC CHEMOKINES

(75) Inventors: Cory M. Hogaboam, Ann Arbor, MI (US); Cynthia L. Bone-Larson, Petersburg, MI (US); Kenneth J. Simpson, Edinburgh (GB); Nicholas W. Lukacs, Brighton, MI (US); Steven L. Kunkel, Ann Arbor, MI (US); Lisa M. Colletti, Webberville, MI (US); Robert M. Strieter, Sherman Oaks, CA (US)

(73) Assignees: The Regents of The University of Michigan, Ann Arbor, MI (US); University Court of The University of Edinburgh (GB)

( * ) Notice: Subject to any disclaimer, the term of this patent is extended or adjusted under 35 U.S.C. 154(b) by 0 days.

(21) Appl. No.: 09/632,531

(22) Filed: Aug. 4, 2000

Related U.S. Application Data
(60) Provisional application No. 60/147,855, filed on Aug. 9, 1999.

(51) Int. Cl.[7] .................... A61K 38/20; A61K 38/00; A01N 63/00; A01N 25/00; C07K 17/00

(52) U.S. Cl. ................ 424/85.2; 424/85.1; 424/93.1; 424/93.21; 514/12; 514/44; 514/893; 530/350

(58) Field of Search ................ 424/85.1, 85.2, 424/93.1, 93.21; 514/12, 44, 893; 530/350

(56) References Cited

U.S. PATENT DOCUMENTS

| | | | |
|---|---|---|---|
| 5,474,981 A | 12/1995 | Leder et al. | 514/12 |
| 5,728,377 A | 3/1998 | Sarris et al. | 424/85.1 |
| 5,824,299 A | 10/1998 | Luster et al. | 424/85.1 |
| 5,871,723 A | 2/1999 | Strieter et al. | 424/85.1 |
| 5,919,763 A | * 7/1999 | Galun et al. | 514/12 |
| 5,935,567 A | 8/1999 | Leder et al. | 424/93.21 |

FOREIGN PATENT DOCUMENTS

WO   WO 98/14581   4/1998

OTHER PUBLICATIONS

Diehl et al., Regulation of liver regeneration by pro–inflammatory cytokines (1996), Journal of Gastroenterology and Hepatology, 11, pp. 466–470.*
Murdoch et al., Chemokine receptors and their role in inflammation and infectious diseases (2000), Blood, 95, pp. 3032–3043.*
Baggiolini et al., Human Chemokines: An Update (1997), Annual Review Immunology, 15, pp. 675–705.*
Bao et al., "Adenoviral delivery of recombinant DNA into transgenic mice bearing hepatocellular carcinomas," *Hum. Gene Ther.*, 7(3):355–365, 1996.
Bautista, "Chronic alcohol intoxication induces hepatic injury through enhanced macrophage inflammatory protein–2 production and intercellular adhesion molecule–1 expression in the liver," *Hepatol.*, 25(2):335–342, 1997.

Bell et al., "Recombinant human adenovirus with rat MIP–2 gene insertion causes prolonged PMN recruitment to the murine brain," *Eur. J. Neurosci.*, 8(9):1803–1811, 1996.
Chanda and Mehandale, "Hepatic cell division and tissue repair: a key to survival after liver injury," *Mol. Med. Today,* 2:82–89, 1996.
Chanda et al., "Stimulated hepatic tissue repair underlies heteroprotection by thioacetamide against acetaminophen––induce lethality," *Hepatol.*, 21(2):477–486, 1995.
Colletti et al., "Role of tumor necrosis factor–α in the pathophysiologic alterations after hepatic ischemia/reperfusion injury in the rat," *J. Clin. Invest.*, 85:1936–1943, 1990.
Colletti et al., "The production of tumor necrosis factor–α and the development of a pulmonary capillary injury following hepatic ischemia/reperfusion," *Transplant.*, 49:268–272, 1990.
Colletti et al., "LPS pretreatment protects from hepatic ischemia/reperfusion," *J. Surg. Res.*, 57:337–343, 1994.
Colletti et al., "TNF triggers the release of ENA–78 which mediates liver injury following hepatic ischemia–reperfusion (I/R)," *FASEB J.*, 8(5):A663, Abstract No. 3845, 1994.
Colletti et al., "Chemokine expression during hepatic ischemia/reperfusion–induced lung injury in the rat. The role of epithelial neutrophil activating protein," *J. Clin. Invest.*, 95(1):134–141, 1995.
Colletti et al., "Hepatic inflammation following 70% hepatectomy may be related to up–regulation of epithelial neutrophil activating protein–78," *Shock*, 6(6):397–402, 1996.
Colletti et al., "The role of cytokine networks in the local liver injury following hepatic ischemia/reperfusion in the rat," *Hepatol.*, 23:506–514, 1996.
Colletti et al., "Proliferative effects of CXC chemokines in rat hepatocytes in vitro and in vivo," *Shock*, 10(4):248–257, 1998.
Colletti et al., "The ratio of ELR+ to ELR–CXC chemokines affects the lung and liver injury followign hepatic ischemia/reperfusion in the rat," *Hepatol.*, 31:435–445, 2000.
Diehl, and Rai, "Review: regulation of liver regeneration by pro–inflammatory cytokines," *J. Gastroent. Hepatol.*, 11:466–470, 1996.
Fahey et al., "Cytokine production in a model of wound healing: The appearance of MIP–1, MIP–2, cachectin/TNF, and IL–1," *Cytokine*, 2(2):92–99, 1990.

(List continued on next page.)

*Primary Examiner*—Lorraine Spector
*Assistant Examiner*—Jegatheesan Seharaseyon
(74) *Attorney, Agent, or Firm*—Williams, Morgan and Amerson

(57) ABSTRACT

Disclosed is the surprising discovery that CXC chemokines function to induce rapid hepatocyte proliferation and liver regeneration after injury. The invention thus provides a range of compositions and methods for use in treating liver injury, including those suitable for treating acetaminophen overdose outside the therapeutic window for N-acetyl-cysteine treatment, and those that limit the hepatotoxic side-effects of gene therapy regimens.

51 Claims, 16 Drawing Sheets

OTHER PUBLICATIONS

Fausto et al., "Liver regeneration. 2. Role of growth factors and cytokines in hepatic regeneration," *FASEB J.,* 9:1527–1536, 1995.

Foley et al., "Adenoviral gene transfer of macrophage inflammatory protein-2 in rat lung," *Am. J. Pathol.,* 149(4):1395–1403, 1996.

Frevert et al., "Functional characterization of rat chemokine macrophage inflammatory protein-2," *Inflamm.,* 19(1):133–142, 1995.

Hogaboam et al., "Novel CXCR2–dependent liver regenerative qualities of ELR–containing CXC chemokines," *FASEB J.,* 13(12):1565–1574, 1999.

Hogaboam et al., "Macrophage inflammatory protein-2 gene therapy attenuates adenovirus– and acetaminophen––mediated hepatic injury," *Gene Therapy,* 6:573–584, 1999.

Hogaboam et al., "Therapeutic use of chemokines," *Curr. Pharm. Des.* 6(6):651–663, 2000.

Hogaboam et al., "Exaggerated hepatic injury due to acetaminophen challenge in mice lacking C–C chemokine receptor 2," *Am. J. Pathol.,* 156(4):1245–1252, 2000.

Huang et al., "Serum levels of interleukin-8 in alcoholic liver disease: relationship with disease stage, biochemical parameters and survival," *J. Hepatol.,* 24:377–384, 1996.

Jaeschke, "Chemokines, neutrophils, and inflammatory liver injury" *Shock,* 6(6):403–404, 1996.

Kay and Fausto, "Liver regeneration: Prospects for therapy based on new technologies," *Mol. Med. Today,* 3(3):108–115, 1997.

Lentsch et al., "Chemokine involvement in hepatic ischemia/reperfusion injury in mice: Roles for macrophage inflammatory protein-2 and KC," [corrected and republished article orginally printed in *Hepatol.,* 27(2): 507–512, 1998,] *Hepatol.,* 27(4):1172–1177, 1998.

Louis et al., "Hepatoprotective role of interleukin 10 in galactosamine/lipopolysaccharide mouse liver injury," *Gastroenterol.,* 112(3):935–942, 1997.

Maher et al., "Adenovirus–mediated expression of CINC/GRO (IL–8) in rat liver induces a neutrophilic hepatitis," *Hepatol.,* 22(4 Pt. 2):228A, Abstract No. 725, 1995.

Muruve et al., "Adenoviral gene therapy leads to rapid induction of multiple chemokines and acute neutrophil–dependent hepatic injury in vivo," *Hum Gene Ther.,* 10:965–976, 1999.

Shimoda et al., "Interleukin–8 and hIRH (SDF1–α/PBSF) mRNA expression and histological activity index in patients with chronic hepatitis C," *Hepatol.,* 28:108–115, 1998.

Sprenger et al., "Induction of neutrophil–attracting chemokines in transforming rat hepatic stellate cells," *Gastroenterol.,* 113(1):277–285, 1997.

Strieter et al., "'The good, the bad, and the ugly.' The role of chemokines in models of human disease," *J. Immunol.,* 156(10):3583–3586, 1996.

Takada et al., "Chemotactic factors released from hepatocytes exposed to acetaminophen," *Dig. Dis. Sci.,* 40(8):1831–1836, 1995.

Thornton et al., "Kupffer cell–derived cytokines induce synthesis of a leukocyte chemotactic peptide, interleukin–8, in human hepatoma and primary hepatocyte cultures," *Hepatol.,* 14:1–11, 1991.

Yoshidome et al., "Roles of MIP–2 and KC in hepatic ischemia/reperfusion injury in mice," *FASEB J.,* 11(3):A295, Abstract No. 1712, 1997.

Co–pending U.S. Patent Application Serial No.: 09/213,383; Entitled: "CXC Chemokines as Regulators of Angiogenesis, "; Filed: Dec. 9, 1998; Inventors: Robert M. Strieter, Peter J. Polverini and Steven L. Kunkel (Reference No. 41000.000799); Divisional of U.S. Patent No. 5,871,723, disclosed as Reference A4.

Hogaboam et al., "Novel CXCR2–dependent liver regenerative qualities of ELR–containing CXC chemokines," *FASEB J.,* A397, 1999.

Partial International Search Report for PCT/US00/21306, mailed Feb. 22, 2001.

International Search Report for PCT/US00/21306, mailed May 29, 2001.

\* cited by examiner

TREATMENT OF LIVER DISEASE AND INJURY WITH CXC CHEMOKINES

The present application claims priority to U.S. provisional application Serial No. 60/147,855, filed Aug. 9, 1999, the entire text and figures of which application is incorporated herein by reference without disclaimer.

The United States Government has certain rights in the present invention pursuant to Grants HL03072-03, IP50HL56402, IP50HL60289, CA66180, HL35276, HL31963 and A136302 from the National Institutes of Health.

BACKGROUND OF THE INVENTION

1. Field of the Invention

The present invention relates generally to the fields of liver injury and regeneration. More particularly, it concerns the surprisingly effective use of CXC chemokines to induce rapid hepatocyte proliferation and liver regeneration. The invention thus provides advantageous methods to treat liver injury caused by a variety of agents, including that associated with acetaminophen overdose and with gene therapy.

2. Description of Related Art

The liver is the only vital organ, aside from the brain, for which there is no pharmacological, mechanical, or extra corporeal means of support for a failing organ. In contrast, there is mechanical ventilation to support patients with pulmonary failure, dialysis to support patients with kidney failure, and a variety of mechanical and pharmacological interventions to maintain the failing heart. The liver is also unique in that it is the only mammalian organ that can regenerate its biologically functional parenchymal mass following resection or injury, instead of healing with biologically nonfunctional scar tissue.

A patient's ability to restore his or her pre-operative hepatic mass following major liver resection is well-known (Weinbren and Hadjis, 1990). A variety of mediators are known to be hepatic mitogens, both in vitro and in vivo, but the precise mechanisms involved in liver regeneration remain to be defined (Hoffman et al., 1994; Fausto et al., 1996). A significant problem with efforts to promote hepatic regeneration is that many agents have limited effectiveness in vivo, involving either the magnitude and/or time of response. The availability of biological or pharmacological maneuvers to accelerate the regeneration of an adequate functional hepatic mass would therefore be a significant advance that could prevent many deaths from liver failure.

The ability to induce or enhance hepatocyte proliferation in the clinical setting would have several important applications. It would allow previously unresectable hepatic malignancies to be resected by increasing the quantity of healthy hepatic tissue, preventing the patient's death from liver failure in the post-operative period due to inadequate remaining functional liver mass. Further, patients suffering from fulminant hepatic failure from toxic, metabolic, or viral causes may be spared death or a liver transplant if the native liver could be induced to regenerate at a rate that would restore adequate hepatic function prior to death from liver failure.

Treatments aimed at inducing liver regeneration would likely have particular benefits in connection with acetaminophen (APAP) overdoses. This is partly because the deleterious effects of accidental or intentional (Makin and Williams, 1997) acetaminophen overdose often manifest many hours after major hepatic injury has occurred. When administered within 8 hours, N-acetyl-cysteine (NAC), a precursor of glutathione that is the standard medical treatment for acetaminophen overdose cases, effectively inhibits liver injury and prevents fulminant hepatic failure (De Groote and Van Steenbergen, 1995). However, because the onset of symptoms of acetaminophen overdose may be delayed or misinterpreted, the therapeutic window for NAC treatment of acetaminophen toxicity is frequently missed (Delanty and Fitzgerald, 1996).

A more recent area for attention within clinical hepatology is connected with the side effects of gene therapy. Acute hepatocellular injury characterized by centrilobular hepatocyte necrosis is a major side effect of viral-based gene therapies targeted to the liver (Yang et al., 1996; Nielsen et al., 1998; Bao et al., 1996). The development of strategies to abrogate the hepatic injury associated with viral-mediated gene therapy is necessary as most viral vectors, including the replication-deficient adenoviruses, efficiently deliver transgenes into hepatocytes without altering the biochemical functions of these cells (Castell et al., 1997; Raper and Wilson, 1995). Although the inhibition of T cell function in the liver is partially effective in limiting the hepatotoxic effects of viral vectors, the prolonged use of immunosuppressants during hepatic gene therapy protocols may predispose patients to opportunistic infections (Yang et al., 1996; Kay et al., 1997; Sullivan et al., 1997). In addition, the potential for greatly enhanced liver injury exists when analgesics are concurrently administered during hepatic gene therapy.

At present, considerable attention is being directed to elucidating factors that promote rapid and maximal liver regeneration following exposure of the liver to toxic or mechanical insults (Fausto et al., 1995). Cytokines such as interleukin-1 (IL-1), and particularly TNFα and interleukin-6 (IL-6), are among the factors believed to possess unique liver regenerative qualities (Khoruts et al., 1991; Diez-Ruiz et al., 1995; Yamada et al., 1997; Cressman et al., 1996).

IL-6-deficient mice have been shown to have impaired liver regeneration following partial hepatectomy (Cressman et al., 1996). Mice lacking type I TNF receptors exhibit impaired liver regeneration following partial hepatectomy, which was also reported to act through an IL-6-dependent pathway (Yamada et al., 1997). Similarly, Rai and colleagues have shown that TNF is important in hepatic regeneration and is further down-regulated by interleukin-10 (IL-10) in this setting (Rai et al., 1997).

Despite ongoing research efforts, there remains in the art a need for improved methods of promoting liver regeneration and repair. Few substances are known that exhibit the required properties and many of these, such as NAC, have limits to their effectiveness in a clinical setting. The development of therapeutic strategies capable of treating liver damage caused by a range of hepatotoxic agents and gene therapy vectors are thus urgently needed, particularly those that promote rapid hepatocyte proliferation. The development of new regimens for treating acetaminophen overdose outside the therapeutic window of NAC therapy would represent a particularly marked advance in this field.

SUMMARY OF THE INVENTION

The present invention overcomes the foregoing and other drawbacks inherent in the prior art by providing a range of new treatments by which to induce liver regeneration and repair. The invention is broadly based upon the surprising finding that CXC chemokines induce rapid hepatocyte proliferation in vitro and stimulate liver repair and regeneration in vivo. Particularly advantageous uses of the invention are in the treatment and/or prevention of liver injury caused by acetaminophen overdose and associated with gene therapy.

The invention is generally based on the use of components or agents, preferably CXC chemokines or CXC chemokine components, that activate or upregulate the CXC chemokine receptor 1 (CXCR1), or more preferably, that activate or upregulate the CXC chemokine receptor 2 (CXCR2). As used herein, the terms "CXC chemokines and CXC chemokine components" are used generically to indicate that the CXC chemokine may be a protein or nucleic acid that encodes a protein.

Therefore, unless otherwise specifically stated, all CXC chemokine biological agents are included within the term "CXC chemokine". Although human CXC chemokines will be preferred for use in human therapy, CXC chemokines from any species may be used in the invention. For use in other animal species, such as in veterinary embodiments, a species of CXC chemokine matched to the animal being treated will be preferred.

A CXC chemokine "protein", as used herein, refers to a proteinaceous CXC chemokine component that has sufficient biological activity to be biologically effective. Accordingly, "CXC chemokine proteins" include full-length CXC chemokine proteins and polypeptides, including those prior to natural biological processing and, preferably, those subsequent to the type of biological processing that occurs naturally.

CXC chemokine proteins and polypeptides also include CXC chemokine proteins and polypeptides that have been subject to non-native processing or biological modification. Such modifications include truncations, extensions, active domains or fragments, fusion proteins, mutants with substantial or sufficient biological activity, peptidomimetics and the like.

Any form of CXC chemokine protein may be used in the invention, including those isolated from natural sources. CXC chemokines prepared by recombinant expression will often be preferred, i.e., those obtained by expressing a CXC chemokine nucleic acid in a recombinant host cell and collecting the expressed CXC chemokine protein. Further preferred CXC chemokine proteins are those prepared by automated peptide synthesis.

"CXC chemokine nucleic acids" are DNA or RNA coding regions that encode, and under conditions appropriate for expression, encode and express any one or more of the biological active CXC chemokine protein- and polypeptide-based components described above, including full-length proteins and polypeptides, and active variants, fragments and fusions thereof. Recombinant vectors, viral vectors and recombinant viruses are preferred for use in various embodiments, as described in detail herein.

A component "that activates or upregulates" the CXC chemokine receptor 1 (CXCR1), or more preferably, the CXC chemokine receptor 2 (CXCR2), is a chemical or biological component or agent that stimulates cell signaling via the CXCR1 or CXCR2 receptor. "Cell signaling" via the CXCR1 or CXCR2 receptor is indicated by the capacity to "transduce" a signal, i.e., transmit a biological effect, to the intracellular environment by binding of an agent to an extracellular portion of the receptor.

Agents that "stimulate" cell signaling via these receptors may do so directly or indirectly. Preferred agents that directly stimulate or "activate" such receptors, preferably the CXCR2 receptor, are generally the biological ligand counterparts to the receptor. Therefore, ELR-containing CXC chemokines will be preferred for directly activating the CXCR2 receptor, as such components are known to bind to and stimulate this receptor in the natural environment.

The term an "ELR-containing CXC chemokine" means a CXC chemokine that includes the ELR motif, i.e., the amino acid sequence ELR (Glu Leu Arg). The ELR sequence is important in defining the receptor binding and biological properties of these chemokines.

Exemplary ELR-containing CXC chemokines for use in all aspects of the invention are MIP-2 (macrophage inflammatory protein-2), ENA-78 (epithelial neutrophil activating protein-78), IL-8 (interleukin-8), GCP-2 (granulocyte chemotactic protein-2), NAP-2 (neutrophil activating peptide-2), CTAP-III (connective tissue activating protein-III), βTG (β-thromboglobulin) and the GRO (growth related oncogene peptide) chemokines, such as GRO-α, GRO-β and GRO-γ. The amino acid and nucleic acid sequences of all such ELR CXC chemokines are known to those of ordinary skill in the art and are further disclosed herein. Certain preferred ELR-containing CXC chemokines for use in the invention are MIP-2, ENA-78 and IL-8.

Where "indirect" stimulation or activation of these receptors, preferably the CXCR2 receptor, is concerned, agents other than biological ligand counterparts will be effective. Such agents are capable of increasing cell signaling via the CXCR2 receptor without themselves binding to the receptor. Accordingly, these components include accessory and accessory signaling molecules, co-stimulators and the like, and agents that remove, inactivate or downregulate inhibitors.

Preferred components that indirectly stimulate the CXCR2 receptor are agents that stimulate or "upregulate" the expression of the CXCR2 receptor. Such components will therefore increase the amount of the receptor expressed at the cell surface and available for binding to the natural biological ligand counterpart, i.e., the "ELR-containing CXC chemokine". Agents that preferentially or specifically upregulate CXCR2 receptor expression are preferred for use in the invention.

The use of agents that specifically upregulate the CXCR2 receptor is exemplified by the surprising use of the non-ELR CXC chemokine, IP-10 (γ-interferon-inducible protein-10). The amino acid and nucleic acid sequences of this component are again known to those of ordinary skill in the art and are further disclosed herein.

In light of the present discoveries, CXC chemokines, preferably ELR CXC chemokines and the non-ELR CXC chemokine, IP-10, may be used in all in vitro and in vivo methods of stimulating hepatocytes and promoting hepatocytes proliferation. All that is required is to contact a composition comprising hepatocytes with a biologically effective amount of at least a first composition comprising at least a first CXC chemokine component that activates or upregulates the CXC chemokine receptor 2 (CXCR2).

Such methods and uses include the addition of the CXC chemokine composition to hepatocytes in vitro. Accordingly, the invention provides methods and uses in culturing hepatocytes in vitro and in generating artificial liver tissue ex vivo. The methods and uses generally comprise providing a biologically effective amount of at least a first composition comprising at least a first CXC chemokine that activates or upregulates the CXCR2 receptor to an in vitro or ex vivo biological sample that contains a population of hepatocytes.

Preferred methods, uses and medicaments of the invention are those in which the CXC chemokine compositions are provided to hepatocytes in vivo, simply by administering the composition to an animal or patient. The invention thus provides methods and uses of inducing liver growth, stimulating hepatic regeneration and, generally, treating animals and patients with various forms of liver damage and disease.

These methods and uses of the invention comprise providing to an animal or patient at least a first composition that comprises at least a first CXC chemokine that activates or upregulates the CXCR2 receptor. The CXC chemokines are provided in amounts effective to promote hepatocyte proliferation, induce liver growth, stimulate hepatic regeneration and/or to generally treat or prevent liver damage, diseases and/or disorders in the animal or patient. This is the meaning of the terms "biologically and therapeutically effective amounts", as used herein, i.e., amounts effective to promote hepatocyte proliferation, induce liver growth, stimulate hepatic regeneration and/or treat or prevent liver damage when administered to an animal or patient.

The in vivo treatment methods of the invention generally require the administration of pharmaceutically or pharmacologically acceptable formulations of CXC chemokine proteins, nucleic acids, vectors and/or recombinant viruses. Systemic administration, including intravenous administration, is suitable for use in the invention. More localized delivery to the liver is also contemplated, including all forms of intra-hepatic administration.

Where protein administration is concerned, the invention contemplates that the CXC chemokine proteins will be administered to animals or patients in doses of between about 1 and about 500 µg/kg body weight; preferably between about 20 and about 400 µg/kg body weight, preferably between about 50 and about 350 µg/kg body weight, and more preferably, between about 100 and 250 µg/kg body weight, such as at about 200 µg/kg body weight.

All intermediate ranges are included, such as 1 to 10, 20, 50, 100, 200, 300, 400 and 500 µg/kg body weight; 20 to 50, 100, 200, 300, 400 and 500 µg/kg body weight; 50 to 100, 200, 300, 400 and 500 µg/kg body weight; 100 to 200, 300, 400 and 500 µg/kg body weight; 200 to 300, 400 and 500 µg/kg body weight, and such like.

In fact, all doses themselves are included, such as 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 and 500 µg/kg body weight, and such like.

The therapeutic aspects of the invention include methods and uses employing at least a first CXC chemokine nucleic acid that expresses a CXC chemokine protein. In these embodiments, the CXC chemokines are preferably, although not exclusively, expressed in cells within or proximal to the liver of the animal or patient, including the hepatocytes themselves.

Recombinant vectors that include one or more exogenous promoters to express the CXC chemokine nucleic acid(s) will generally be preferred for use in these aspects of the invention. Constitutive promoters may be used, generally to obtain high levels of CXC chemokine expression. Exemplary constitutive promoters include SV40, CMV, RSV and ribosomal (RS) promoters.

Alternatively, the use of liver tissue or liver cell-specific or liver tissue or liver cell-preferential promoters may be preferred. Such promoters will specifically or preferentially direct expression of the CXC chemokine in cells within or proximal to the liver, including in hepatocytes. Suitable examples of such promoters include transphyretin, α1-antitrypsin, plasminogen activator inhibitor type 1 (PAI-1), apolipoprotein AI and LDL receptor gene promoters, each of which specifically or preferentially direct expression in liver cells and tissue.

Using administration via recombinant adenovirus to exemplify the recombinant CXC chemokine delivery aspects of the invention, the CXC chemokine nucleic acids may be provided by administering a recombinant adenovirus to the animal or patient at a dose of between about $1 \times 10^8$ PFU per animal and about $1 \times 10^{12}$ PFU per animal. Those of ordinary skill in the art will understand that the lower doses are preferably administered by infusion into the hepatic artery, whereas higher doses are suitable for systemic administration. Administration of recombinant adenoviruses that comprise at least a first CXC chemokine nucleic acid at doses of about $1 \times 10^9$, $1 \times 10^{10}$ and $1 \times 10^{11}$ PFU per animal are also contemplated.

Whether proteins or nucleic acids are employed in the methods and uses of the invention, the CXC chemokines may be used alone or in combination. Accordingly, the invention encompasses the use of one, two, three, four, five, six or more CXC chemokines. The CXC chemokines may also be used in combination with other therapeutic or hepatoproliferative agents. For example, NAC (N-acetylcysteine), HGF (hepatocyte growth factor), stem cell factor (SCF), TNF-α (tumor necrosis factor-α) and/or IL-6 (interleukin-6) may be used in combination with the present invention.

A wide range of diseases, disorders and conditions associated with liver damage may be treated by the compositions, kits, formulations, methods, uses and medicaments of the invention. These include liver damage associated with exposure to alcohol, hepatotoxic drugs and combinations thereof. Exemplary damaging agents are anticonvulsants, phenytoin, carbamazepine and phenobarbital, and recreations drugs, such as ecstasy (3,4-methylenedioxymethamphetamine).

Side effects resulting from other therapies may also be treated by the invention, including the liver damage associated with exposure to antituberculosis agents and chemotherapeutic agents, such as isoniazid and rifampicin. Liver damage associated with a reduction in viable liver tissue may also be treated, such as occurs after resecting a carcinoma.

Liver damage resulting from or associated with infectious agents may also be counteracted using the present invention. This includes liver damage associated with bacterial, parasitic, fungal and viral infections. For example, liver damage results from Aspergillus fungal infections, Schistosoma parasitic infections and a variety of viral infections, such as adenovirus, retrovirus, adeno-associated virus (AAV), hepatitis virus A, hepatitis virus B, hepatitis virus C, hepatitis virus E, herpes simplex virus (HSV), Epstein-Barr virus (EBV) and paramyxovirus infections. All of which may be treated hereby.

A particularly important use of the present invention is in the treatment or even prevention of liver damage associated with excess acetaminophen (paracetamol) ingestion. This may occur over a prolonged time period, leading to chronic liver damage; or during a short or immediate time period, leading to acute liver damage. The latter embodiments include deliberate and accidental overdoses, including in both adults and children.

The invention therefore provides methods and uses in treating acetaminophen-induced liver damage, which generally comprise administering to an animal or patient with acetaminophen-induced liver damage a biologically effective amount of at least a first composition comprising at least a first CXC chemokine that activates or upregulates the CXC chemokine receptor 2 (CXCR2).

These methods and uses are suitable for treating an acetaminophen overdose, wherein they comprise administering to an animal or patient suffering from an acetaminophen overdose at least a first composition that comprises at least a first CXC chemokine in an amount effective to activate or upregulate the CXC chemokine receptor 2 (CXCR2), thereby promoting liver cell proliferation and liver regeneration in the animal or patient.

Excess acetaminophen ingestion may be effectively treated by the present invention after more time delay than currently available methods, particularly NAC treatment. Accordingly, the invention provides methods and uses for treating an acetaminophen overdose comprising identifying an animal or patient presenting with acetaminophen overdose outside the therapeutic window for NAC treatment and administering to the animal or patient at least a first composition that comprises an amount of at least a first CXC chemokine effective to overcome the acetaminophen overdose.

The importance of the invention is such that the methods and uses include those for avoiding liver transplantation in an acetaminophen overdose animal or patient. These comprise treating the animal or patient with at least a first CXC chemokine that activates or upregulates the CXC chemokine receptor 2 (CXCR2) in a manner effective to regenerate sufficient operative liver tissue so as to render a liver transplant unnecessary.

Treatment of acute liver damage is not limited to that caused by excess acetaminophen ingestion, but is widely applicable. The invention therefore provides methods and uses for treating acute liver damage wherein at least a first dose of the CXC chemokine composition is administered to an animal or patient within a biologically effective time period after onset of the liver damage.

The "biologically effective time periods" after onset of liver damage are exemplified by time periods of between about ten minutes and about 72 hours; preferably, between about half an hour and about 18 hours; and more preferably, between about an hour and about 10, 12 or 15 hours after onset of liver damage. The invention includes all such ranges and particular times.

For example, administration at between about ten minutes and about 1, 2, 3, 5, 8, 10, 12, 15, 18, 24, 36, 48, 60 and 72 hours; between about half an hour and about 1, 2, 3, 5, 8, 10, 12, 15, 18, 24, 36, 48, 60 and 72 hours; between about an hour and about 2, 3, 5, 8, 10, 12, 15, 18, 24, 36, 48, 60 and 72 hours; between about 2 hours and about 3, 5, 8, 10, 12, 15, 18, 24, 36, 48, 60 and 72 hours; between about 5 hours and about 10, 12, 15, 18, 24, 36, 48, 60 and 72 hours; between about 10 hours and about 12, 15, 18, 24, 36, 48, 60 and 72 hours; between about 11 or 12 hours and about 15, 18, 24, 36, 48, 60 and 72 hours; between about 15 hours and about 18, 24, 36, 48, 60 and 72 hours; between about 18 hours and about 24, 36, 48, 60 and 72 hours; between about 24 hours and about 36, 48, 60 and 72 hours; between about 36 hours and about 48, 60 and 72 hours; and between about 48 hours and about 55, 60 and about 72 hours after onset of liver damage.

Rapid administration is desirable, although not essential. The invention therefore includes administration at about 10, 20, 30, 60 or 90 minutes, and at about 1, 2, 3, 4, 5, 6, 7, 8, 9 or 10 hours or so after onset of liver damage.

Effective administration at times unsuitable for other therapies is important. These aspects of the invention include administration at about 10, 11, 12, 13, 14, 15, 16, 17, 18, 19, 20, 21, 22, 23, 24, 25, 26, 27, 28, 39, 30, 31, 32, 33, 34, 35 and 36 hours or so after onset of liver damage.

Administration of at least a first dose of the CXC chemokine composition at a time between about ten hours and about 72 hours after onset of said liver damage is one of these important, although not limiting, features of the present invention as these effective treatment times are outside the effective window of NAC treatment. Administration at any effective time after about 10 hours after onset of liver damage is therefore important. These includes administration at a time of about 38, 40, 42, 44, 46, 48, 50, 52, 54, 56, 58, 60, 62, 64, 66, 68, 70 and 72 hours after onset of liver damage.

The invention thus provides methods and uses for timely treating animals and patients with acute liver damage, comprising administering to the animal or patient a biologically effective amount of at least a first CXC chemokine composition at a time between about ten hours and about 72 hours after the onset of liver damage; wherein the CXC chemokine composition comprises at least a first CXC chemokine that activates or upregulates the CXC chemokine receptor 2 (CXCR2) in the animal or patient.

A further method and use of timely therapeutic intervention in an animal or patient with acute liver failure comprises the steps of:
  identifying an animal or patient presenting with acute liver failure outside the therapeutic window for NAC treatment; and
  administering to the animal or patient at least a first CXC chemokine composition that comprises an amount of at least a first CXC chemokine effective to overcome acute liver failure; wherein the CXC chemokine activates or upregulates the CXC chemokine receptor 2 (CXCR2) in the animal or patient.

Still further methods and uses of timely therapeutic intervention in an animal or patient with acute liver failure comprise the steps of:
  identifying an animal or patient exposed to a liver damaging agent between about ten hours and about 72 hours before intended therapy; and
  administering to the animal or patient an amount of at least a first CXC chemokine composition that comprises at least a first CXC chemokine effective to overcome the acute liver failure in the animal or patient by activating or upregulating the CXC chemokine receptor 2 (CXCR2) in the liver of the animal or patient.

The time benefits of the invention are considerable, although not limiting. Accordingly, the invention includes methods and uses for treating chronic liver damage, wherein the CXC chemokine composition is administered to an animal or patient over an extended biologically effective time period. In such treatment, repeated administrations would likely be required, as may be readily achieved by a number of methods, including adenoviral gene therapy. Accordingly, chronic liver damage may be treated by repeated doses of CXC chemokine compositions administered said animal at about 3 day intervals for about 2 months.

In addition to the foregoing general therapeutic embodiments, the methods, uses and medicaments of the present invention that comprise recombinant viruses expressing CXC chemokines are important in connection with treating and/or preventing adenovirus-mediated liver damage, particularly that associated with gene therapy. In such aspects, the invention provides recombinant adenoviruses that comprise at least a first CXC chemokine nucleic acid in combination with a nucleic acid that expresses a therapeutic protein.

The present invention thus encompasses methods and uses for providing a therapeutic nucleic acid to an animal or patient, comprising administering to the animal or patient a single recombinant adenovirus that comprises a first nucleic acid that expresses a therapeutic protein and a second nucleic acid that expresses a CXC chemokine that activates or upregulates the CXC chemokine receptor 2 (CXCR2) in an amount effective to ameliorate hepatotoxic side effects of the recombinant adenovirus.

Such methods of gene therapy further comprise administering to an animal or patient:

a recombinant adenovirus comprising a recombinant nucleic acid that expresses a therapeutic protein in target cells of the animal or patient; and at least a first composition that comprises at least a first CXC chemokine that activates or upregulates the CXC chemokine receptor 2 (CXCR2) in an amount effective to attenuate hepatotoxic effects of the recombinant adenovirus.

Although CXC chemokine proteins may be used to attenuate hepatotoxic effects of recombinant adenoviruses, the use of CXC chemokine nucleic acids and recombinant viruses is preferred. Recombinant adenoviruses that express CXC chemokines are particularly preferred, especially where the recombinant adenovirus expresses both the CXC chemokine and the therapeutic nucleic acid (or antisense, etc.) of intended therapy.

The invention thus provides methods and uses for preventing or reducing the hepatotoxicity of adenoviral-mediated gene therapy, comprising combining the administration of an adenoviral gene therapy construct with the administration of at least a first composition that comprises at least a first CXC chemokine that activates or upregulates the CXC chemokine receptor 2 (CXCR2) in an amount effective to reduce hepatotoxicity caused by the adenoviral gene therapy construct.

In further embodiments, therapeutic kits are provided. These comprise at least a first recombinant adenovirus that comprises at least a first nucleic acid segment that expresses a therapeutic protein; and a composition comprising at least a first CXC chemokine that activates or upregulates the CXC chemokine receptor 2 (CXCR2) in an amount effective to reduce hepatotoxic effects of the recombinant adenovirus.

The kits may comprise any of the foregoing CXC chemokine proteins, polypeptides, nucleic acid segments and recombinant viruses, including wherein a single recombinant adenovirus expresses at least a first CXC chemokine and a therapeutic RNA or protein. The kits may also comprise at least a first hepatoproliferative agent other than a CXC chemokine.

Recombinant adenovirus compositions form further aspects of the invention. These comprise a recombinant adenovirus that comprises at least a first nucleic acid segment that expresses a therapeutic protein and at least a second nucleic acid segment that expresses a CXC chemokine that activates or upregulates the CXC chemokine receptor 2 (CXCR2). Packing such recombinant adenoviruses gives rise to the gene therapy formulations of the invention.

All such compositions, kits and gene therapy formulations of the invention may comprise any one or more of the CXC chemokine proteins, polypeptides and nucleic acid segments known in the art and described herein, including ELR-containing CXC chemokines, such as MIP-2, ENA-78, IL-8, and the non-ELR-containing CXC chemokine, IP-10, that upregulates CXCR2 receptor expression.

Finally, the invention provides for the use of the compositions in accordance herewith in the preparation of a variety of medicaments for treating one or more conditions associated with liver damage, including chronic and acute liver damage and liver damage associated with exposure to alcohol, surgical intervention, hepatotoxic drugs and infectious agents, including excess acetaminophen ingestion, adenoviral infection and adenoviral-mediated gene therapy.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
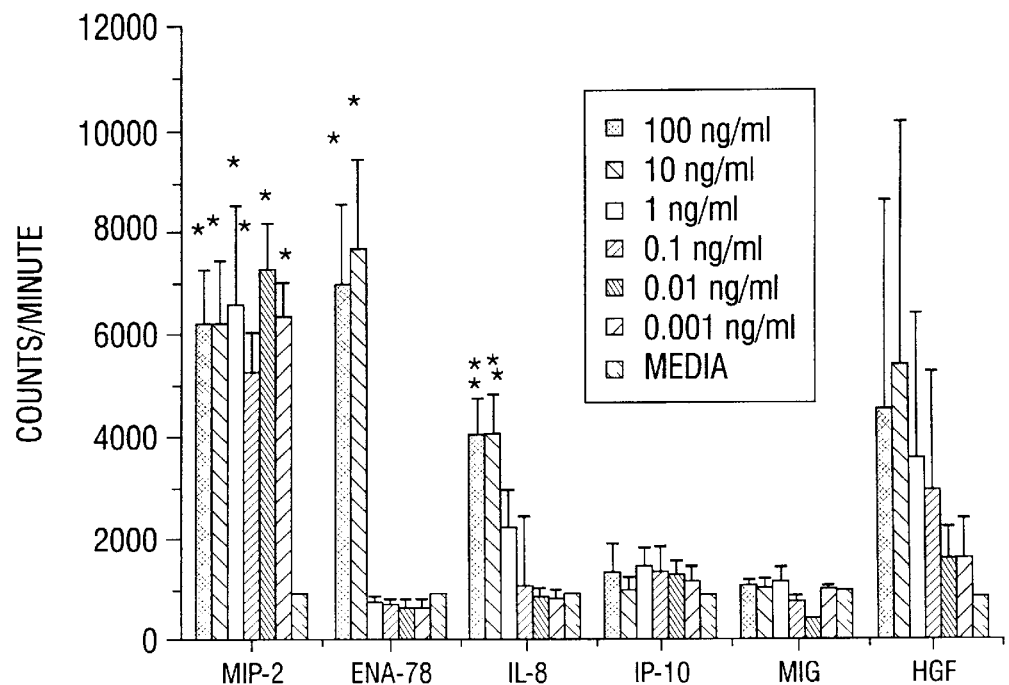
FIG. 1. Proliferation of primary rat hepatocytes in vitro in response to ELR positive and ELR negative CXC chemokines, as measured by incorporation of $^3$H-thymidine. Primary rat hepatocytes in vitro were stimulated with increasing concentrations of MIP-2, ENA-78, IL-8, IP-10, or MIG and proliferation was assessed by incorporation of $^3$H-thymidine at 24 h of incubation. Human hepatocyte growth factor (HGF), at identical concentrations, was used as a positive control. Media alone was used as a negative control. $^3$H-thymidine incorporation by hepatocytes at 24 h of incubation shows a significant proliferative response to the ELR positive CXC chemokines, MIP-2, ENA-78, and IL-8. There is no proliferative response to the ELR negative chemokines, IP-10 and MIG, at the concentrations used: *$p<0.001$ vs. media alone; +$p<0.001$ vs. media alone and $p<0.05$ vs. HGF, at comparable concentrations; **$p<0.05$ vs. media alone.

Excessive hepatocyte necrosis in the damaged liver poses a significant problem as it can lead to liver failure and death. It is critical to the integrity of an acutely injured liver that hepatocytes quickly exit the quiescent $G_0$ phase and enter the cell cycle to begin proliferating (Alison et al., 1997). The development of clinical regimens to intercept hepatocyte death, and to instead promote hepatic regeneration after injury, is of significant importance in the treatment of a wide variety of diseases and conditions.

For example, despite advances in supportive care, acute hepatic failure attributed to acetaminophen ingestion approaches 50% in the United Kingdom (Atillasoy and Berk, 1995). A liver transplant could ensure patient survival in these cases (Bernal et al., 1998), but the majority of patients affected by acetaminophen overdose do not fulfill all the necessary criteria for liver transplantation because they lack co-existent renal failure or severe acidosis (Riordan and Williams, 1999).

The elucidation of factors that promote hepatic regeneration after acute injury has thus garnered considerable attention. The list of hepatic regenerative factors now includes numerous endogenously-generated growth factors, such as hepatocyte growth factor (HGF) and basic fibroblast growth factor (bFGF), and immunomodulatory cytokines, such as interleukin-10 (Kay and Fausto, 1997; Louis et al., 1997). In addition, hepatic regeneration following acute injury due to experimental ischemia/reperfusion, hepatectomy or hepatotoxin exposure also appears to require the regulated involvement of proinflammatory mediators (Bruccoleri et al., 1997; Renic et al., 1993; Tiggelman et al., 1995; Trautwein et al., 1998).

Inflammation is a critical component of the host response to injury and infection and is intimately tied to tissue repair and wound healing. TNF and subsequently released mediators, including ENA-78, have been demonstrated to play an important role in the inflammatory process that follows many types of liver injury (Lentsch et al., 1998; Sprenger et al., 1997). However, these situations are complex, as it can be difficult to determine whether a given molecule mediates the underlying damage and injury, or whether it is part of the reparative process.

The present inventors have identified several potential explanations for the ongoing production of proinflammatory cytokines, such as IL-1α, IL-1β, TNFα and IL-6 (Bruccoleri et al., 1997; Renic et al., 1993; Tiggelman et al., 1995; Trautwein et al., 1998), during hepatic disease. First, in liver disease associated with ongoing infection, there may be persistent hepatic macrophage stimulation, with increased cytokine production. Second, there may be impaired Kupffer cell or hepatocyte clearance of circulating mediators secreted in otherwise normal amounts, allowing these substances access to the systemic circulation. Finally, the inventors reasoned, inflammatory mediators may be important in initiating hepatic regeneration following liver injury, and are therefore chronically upregulated for ongoing hepatic repair.

Although the ability of an agent to mediate an inflammatory response cannot be directly equated with defined proliferative effects on any given cell type, various studies have supported a role for certain pro-inflammatory cytokines in hepatic regeneration and repair following inflammation and/ or injury. TNF and IL-6, in particular, have been shown to be important in such processes (Cressman et al., 1996; Rai et al., 1997; Akerman et al., 1992; Feingold et al., 1988; Beyer and Stanley, 1990; Kubo et al., 1996; Diehl and Rai, 1996; Rai et al., 1996).

TNF has been demonstrated to be upregulated following partial hepatectomy and inhibition or neutralization of TNF in this setting inhibits liver regeneration (Cressman et al., 1996; Yamada et al., 1997; Rai et al., 1997; Akerman et al., 1992; Diehl and Rai, 1996; Rai et al., 1996). Further, Feingold and colleagues have illustrated that administration of exogenous TNF to normal rats stimulates hepatic DNA synthesis, with an overall increase in hepatic size and weight (Feingold et al., 1988). In similar studies, exogenous TNF administered following 70% hepatectomy increased the rate of hepatic regeneration, as compared to animals receiving a saline control (Beyer and Stanley, 1990).

Hepatocyte proliferation can be induced in rats by treatment with lead nitrate, without the need for hepatic resection or injury (Kubo et al., 1996). In this setting, a significant increase in serum TNF occurs without a concurrent increase in serum hepatocyte growth factor (HGF), and the serum TNF increases parallel hepatocyte proliferation (Kubo et al., 1996). Bruccoleri et al. (1997) have also shown that TNF-α promotes liver recovery following carbon tetrachloride challenge through its stimulation of early-immediate genes required for hepatic mitogenesis.

Despite the availability of agents such as HGF, TNF and IL-6, it is clear that the discovery of additional hepatoproliferative agents would greatly enhance a clinician's ability to successfully treat patients presenting with liver failure. The present inventors were the first to reason that mediators of the CXC chemokine group, particularly those acting through the ELR CXC chemokine receptor, CXCR2, may be important in liver regeneration and response to hepatic injury.

The primary concept that ELR CXC chemokines may actually promote liver regeneration and repair is in direct contrast the body of scientific literature available prior to the present invention. ELR CXC chemokines include IL-8, ENA-78, MIP-2 and KC (see below), each of which molecules have previously been implicated in the cause of liver injury, not as potential therapeutic agents to limit injury and/or promote repair and regeneration.

For example, IL-8, one of the first known ELR CXC chemokines, was suggested to cause neutrophil recruitment to the liver and to make an important contribution to various conditions such as alcoholic hepatitis (Maher et al., 1995). Studies with MIP-2 also led to reports that MIP-2 and other adhesion molecules may contribute to the initiation of hepatic injury during alcohol intoxication (Bautista, 1997). The underlying MIP-2 studies included those reporting that MIP-2 and KC were responsible for the neutrophil recruitment into the liver that follows ischemia and reperfusion injury (Lentsch et al., 1998; Yoshidome et al., 1997), following which, MIP-2 was proposed to play a major role in ischemic liver injury (Yoshidome et al., 1997).

MIP-2 was also earlier shown to be produced by immune-activated hepatocytes and stellate cells, and from hepatocytes exposed to acetaminophen (Bautista, 1997; Sprenger et al., 1997; Takada et al., 1995). The Sprenger et al. (1997) studies were suggested to show that chemokines play an important role in the pathogenesis of liver fibrosis.

Other reports also strengthened the former belief in the art that CXC chemokines, such as ENA-78 and IL-8, contribute to neutrophil-mediated injury in various pathophysiological conditions (Jaenschke et al., 1996). Many such studies were focused on ENA-78, which was reported to be a major mediator for neutrophil-mediated liver injury after 70% hepatectomy (Colletti et al., 1996b) and hepatic ischemia/ reperfusion (Colletti et al., 1994; 1996a; 1996c).

Therefore, although previous studies suggested that CXC chemokines, such as MIP-2 and ENA-78, mediate neutrophil influx and inflammatory responses following hepatic ischemia and reperfusion injury (Colletti et al., 1995; 1996a; 1996b; 1996c), a link to liver regeneration had not been envisioned. In fact, little was known about the role of CXC chemokines in the acutely injured liver prior to the present discoveries. The current invention is based upon the surprising discoveries that ELR-containing CXC chemokines, including IL-8, ENA-78 and MIP-2, not only stimulate hepatocyte proliferation in vitro, but also mediate timely and effective liver repair and regeneration after injury in vivo.

The invention is further strengthened by the unifying concept that agents that upregulate or activate the ELR CXC chemokine receptor, CXCR2, will have similar beneficial effects. Thus, the invention extends to the use of the non-ELR CXC chemokine, IP-10, which is herein shown to counteract acetaminophen-induced liver toxicity in vivo, an effect mediated by an increase in expression of the ELR CXC chemokine, MIP-2, and the ELR CXC chemokine receptor, CXCR2. Thus, whilst the therapeutic effects of ELR CXC chemokines are direct, non-ELR chemokines, particularly IP-10, also have significant therapeutic benefits, although these are achieved by more indirect mechanisms.

1. CXC Chemokines

CXC chemokines are best known for their neutrophil chemotactic and angiogenic actions (Strieter et al., 1995a; Strieter et al., 1993). Many members of this family have been described, including ENA-78, MIP-2, IL-8, IP-10, and MIG (Matsushima and Oppenheim, 1989; Baggiolini et al., 1989; Oppenheim et al., 1991; Miller and Krangel, 1992).

In certain CXC chemokines, an ELR (Glu-Leu-Arg) amino acid sequence is situated next to the first cysteine of the CXC sequence. The ELR sequence is important in receptor binding (Herbert et al., 1991; Clark-Lewis et al., 1993; 1995) and defines the biological activity of the molecule (Strieter et al., 1995a; Strieter et al., 1993; U.S. Pat. No. 5,871,723; application Ser. No. 09/213,383, each incorporated herein by reference).

"ELR CXC chemokines" include interleukin-8 (IL-8), epithelial neutrophil activating protein (ENA-78), macrophage inflammatory protein-2 (MIP-2) (Fahey et al., 1990) and KC. ELR-containing CXC chemokines are classically defined as factors that recruit inflammatory cells to inflamed tissues. Other molecules in the CXC chemokine family lack the ELR sequence, as exemplified by interferon-γ-inducible protein (IP-10) and monokine induced by interferon-γ (MIG). CXC chemokines without the ELR motif typically lack the biological activity of the ELR-containing chemokines.

The ELR sequence is most notably absent in PF-4, IP-10, and MIG (Strieter et al., 1995b; U.S. Pat. No. 5,871,723). These CXC molecules have a significantly decreased ability to induce neutrophil chemotaxis. When the ELR motif was introduced into PF-4, its neutrophil chemotactic properties increased 1,000-fold (Clark-Lewis et al., 1993), showing that this particular region is important for neutrophil chemotactic activity (Strieter et al., 1995a; Herbert et al., 1991; Clark-Lewis et al., 1993; Clark-Lewis et al., 1995; Chuntharapai and Kim, 1995).

The ELR motif was also discovered to account for the disparate abilities of the CXC chemokines to function as promoters or inhibitors of angiogenesis (Strieter et al., 1995a; U.S. Pat. No. 5,871,723; application Ser. No. 09/213,383). This was found to be present in all members of the CXC family that promote angiogenesis. A unifying scheme was thus proposed in which ELR-containing CXC chemokines are angiogenic, while CXC chemokines lacking the ELR sequence are angiostatic (Strieter et al., 1995a; U.S. Pat. No. 5,871,723; application Ser. No. 09/213,383). When non-ELR containing chemokines are combined with ELR-positive chemokines, the angiogenic properties of the ELR positive molecules are suppressed, confirming that the ELR motif is critical for dictating angiogenic activity (Strieter et al., 1995a; 1995b; U.S. Pat. No. 5,871,723; application Ser. No. 09/213,383).

ELR-CXC chemokines are specific for the CXC chemokine receptor 1 (CXCR1) and receptor 2 (CXCR2). The CXCR2 receptor is the main receptor for the ELR-CXC chemokines (Cacalano et al., 1994). Non-ELR-CXC chemokines, which lack angiogenic and mitogenic effects, typically bind to CXCR3 and CXCR4.

The CXC chemokines were first studied in connection with their neutrophil chemotactic properties (Matsushima and Oppenheim, 1989; Baggiolini et al., 1989; Oppenheim et al., 1991; Miller and Krangel, 1992; Strieter et al., 1996). The angiogenic properties of the CXC chemokines are also now well known (Strieter et al., 1995a; 1995b; U.S. Pat. No. 5,871,723). However, these molecules also have mitogenic actions on certain cell types (Matsushima and Oppenheim, 1989; Baggiolini et al., 1989; Oppenheim et al., 1991; Miller and Krangel, 1992; Driscoll et al., 1995; Strieter et al., 1995b; Koch et al., 1992; Maione et al., 1990; Michel et al., 1992), including keratinocytes (Michel et al., 1992), epithelial cells (Driscoll et al., 1995) and endothelial cells (Strieter et al., 1995b), and are present in damaged skin (Kulke et al., 1998).

IL-8 is the most well-studied CXC chemokine and is produced by many cell types in response to TNF and IL-1, including monocytes, alveolar macrophages, neutrophils, keratinocytes, mesangial cells, epithelial cells, hepatocytes, fibroblasts, and endothelial cells (Mawet et al., 1996; Thornton et al., 1991; Matsushima and Oppenheim, 1989; Baggiolini et al., 1989; Oppenheim et al., 1991; Miller and Krangel, 1992; Thornton et al., 1990). Michel and colleagues have demonstrated that IL-8 induces keratinocyte proliferation, with this effect being directly attributable to specific IL-8 receptors on the keratinocyte (Michel et al., 1992). Subsequent keratinocyte binding studies showed that the IL-8 receptor ligand interactions were specific for IL-8, and similar in concentration to those needed for optimal neutrophil chemotaxis and angiogenesis (Matsushima and Oppenheim, 1989; Baggiolini et al., 1989; Oppenheim et al., 1991; Miller and Krangel, 1992; Strieter et al., 1995b; Koch et al., 1992).

Similarly, ENA-78 and MIP-2 are also produced in response to TNF (Colletti et al., 1996a; Strieter et al., 1992; Walz et al., 1991; Driscoll et al., 1995). MIP-2 causes rat alveolar epithelial cell proliferation in vitro and is also mitogenic for melanoma cells (Miller and Krangel, 1992; Thornton et al., 1990; Driscoll et al., 1995).

The present invention shows that ELR CXC chemokines have surprising proliferative effects on hepatocytes, and provides extensive in vitro and in vivo data supporting their new uses in liver repair and regeneration. Any one or more of the ELR CXC chemokines may be used in the present invention, including MIP-2, ENA-78, IL-8, KC, GCP-2, NAP-2, CTAP-III, βTG, GRO-α, GRO-β and GRO-γ, of which, MIP-2, ENA-78 and IL-8 will often be preferred. The invention also extends to the therapeutic use, as validated by in vivo data, of components that activate and/or upregulate the CXCR2 receptor. A particularly surprising example is the beneficial use of the non-ELR CXC chemokine, IP-10, which unexpectedly has the same net beneficial effect, despite being from the sub-set of chemokines that typically have opposite actions to those of the ELR CXC chemokines. The overall benefit results from upregulating MIP-2 and the CXCR2 receptor, Certain preferred, although by no means limiting, ELR CXC chemokines for use in the invention are listed in Table A, from which all of the gene and protein sequences are specifically incorporated herein by reference. Table A also includes and incorporates by reference the gene and protein sequences for IP-10, the preferred non-ELR chemokine for use in the invention. Each of U.S. Pat. No. 5,871,723 and application Ser. No. 09/213,383, including their sequence listings, are also specifically incorporated herein by reference for purposes that include providing even more detail on ELR and non-ELR CXC chemokine DNA and protein sequences.

TABLE A

CXC Chemokines

| CXC Chemokine | | Accession Numbers | |
|---|---|---|---|
| | Source | Nucleic Acids | Proteins |
| IL-8 | Human | M28130 (DNA) | AAA59158 (PR1) |
| ENA-78 | Human | 246254 | AAA86426 (PR1) |
| | | L37036 (DNA) | |
| MIP-2 | Rodent | X53798 (RNA) | P10889 |
| KC | Rodent | U20527.1 (DNA) | AAB03376 |
| IP-10 | Human | 4504700 | 4504700 |
| | | NM_001565.1 | MP_001556 |

In addition to the foregoing ELR CXC chemokine sequences, representative amino acid sequences are also incorporated herein from co-owned U.S. Pat. No. 5,871,723 and application Ser. No. 09/213,383. Specifically, the IL-8 (SEQ ID NO:3), ENA-78 (SEQ ID NO:4) and IP-10 amino (SEQ ID NO:1) amino acid sequences are incorporated. As GCP-2, NAP-2, CTAP-III, βTG, GRO-α, GRO-β or GRO-γ may also be used in the present invention, the sequences of such molecules are incorporated herein by reference from U.S. Pat. No. 5,871,723 as follows: PBP (SEQ ID NO:8); GCP-2 (SEQ ID NO:12); NAP-2 (SEQ ID NO:11); CTAP-III (SEQ ID NO:9); βTG (SEQ ID NO:10); GRO-α (SEQ ID NO:5); GRO-β (SEQ ID NO:6); and GRO-γ (SEQ ID NO:7).

Several of the above sequences represent the CXC chemokine prior to processing. Using the following information, processed forms may be readily made. IP-10 is processed after Gly at position 21; IL-8 is processed after Arg at position 27; ENA-78 is processed after Ser at position 36; GROα and GROβ are processed after Gly at position 34; and GROγ is processed after Gly at position 33. Platelet basic protein (PBP) is processed after Ala at position 34. Physiologically, further processing of PBP gives CTAP-III, βTG and NAP-2, as represented by the above sequences. GCP-2 of SEQ ID NO: 12 may also be processed to give peptides with two, five and eight amino acids removed from the N-terminus.

As each of the CXC chemokines are relatively short polypeptides, these chemokines could be made using the presently available automated peptide synthesis technology. Smaller peptides could also be generated and then joined, resulting in the desired product. The CXC chemokine compositions for use in the invention may also include proteins or peptides that have been modified or "biologically protected". Biologically protected compositions, particularly peptides, have certain advantages over unprotected peptides when administered to human subjects and, as disclosed in U.S. Pat. No. 5,028,592 (incorporated herein by reference). Protected peptides therefore often exhibit increased pharmacological activity.

Compositions for use in the present invention may also comprise CXC chemokines that include all L-amino acids, all D-amino acids or a mixture thereof. The use of D-amino acids may be advantageous in certain embodiments, again particularly with peptides, as such peptides are known to be resistant to proteases naturally found within the human body, may be less immunogenic, and can therefore be expected to have longer biological half lives.

In terms of CXC chemokine nucleic acid sequences, those listed in Table A, each incorporated herein by reference, will often be preferred. In addition, U.S. Pat. No. 5,871,723 and application Ser. No. 09/213,383, as incorporated herein by reference, disclose IP-10 nucleic acid sequences from Luster et al., 1985, 1987, Luster and Ravetch, 1987a, 1987b, Mukaida et al., 1989, sand Modi et al., 1990; IL-8 nucleic acid sequences from Lindley et al. (1988), Schmid and Weissmann (1987) and Matsushima et al. (1988); ENA-78 nucleic acid sequences from Walz et al. (1991), Power et. al. (1994), Corbett et al. (1994) and Chang et. al. (1994); and GROα, GROβ and GROγ nucleic acid sequences from Anisowicz et al. (1988), Martins-Green et al. (1991), Martins-Green and Bissell (1990), Iida and Grotendorst (1990), Richmond et al. (1988) and Haskill et al. (1990). Each of the foregoing scientific articles are also incorporated herein by reference.

CTAP-III, NAP-2 and βTG protein and nucleic acid sequences are highly related. An exemplary nucleic acid sequence is described in Wenger et. al. (1989), incorporated herein by reference. The GCP-2 amino acid sequence of Proost et. al. (1993) (SEQ ID NO:12 in U.S. Pat. No. 5,871,723) may also be used to obtain GCP-2 cDNAs and genes. The following nucleic acid sequences are also specifically incorporated herein by reference from U.S. Pat. No. 5,871,723: IL-8 (SEQ ID NO:77); ENA-78 (SEQ ID NO:88); GROα (SEQ ID NO:90); GROβ (SEQ ID NO:91); GROγ (SEQ ID NO:92); and PBP (SEQ ID NO:93), which results in CTAP-III, βTG and NAP-2 sequences.

2. Hepatoproliferative Effects of ELR CXC Chemokines

One of the threads contributing to the present invention was the inventors' analysis of the actions of TNF on liver repair and regeneration. While various studies have reported that TNF causes hepatocyte proliferation (Cressman et al., 1996; Rai et al., 1997; Akerman et al., 1992; Feingold et al., 1988; Beyer and Stanley, 1990; Kubo et al., 1996; Diehl and Rai, 1996; Rai et al., 1996), the inventors realized that TNF induces a multitude of other mediators in vivo. The inventors therefore reasoned that the foregoing studies do not definitively show that TNF is directly responsible for hepatic regeneration in vivo and that other mediators, triggered in response to TNF, may be important in this process.

It has been demonstrated that hepatic TNF production following 70% hepatectomy occurs just prior to the onset of hepatocyte proliferation (Satoh et al., 1991). Hepatic inflammation has been associated with partial hepatectomy, as evidenced neutrophil influx into the remaining hepatic parenchyma (Colletti et al., 1996b; Satoh et al., 1991). Treatment with dexamethasone, which is known to suppress TNF secretion, reduced TNF levels, hepatic inflammation, and hepatocyte proliferation (Satoh et al., 1991).

Nonetheless, the Satoh et al. (1991) study still failed to demonstrate, to the satisfaction of the inventors, that TNF is directly responsible for the observed mitogenic actions. The inventors proposed that the observed hepatic inflammation was related to the presence of other TNF-induced mediators, such as the CXC chemokines. CXC chemokines are released by hepatocytes in response to TNF and have been shown to be involved in hepatic inflammation and neutrophil recruitment (Colletti et al., 1996a; 1996b). However, the potential connection between additional TNF-induced molecules, particularly the CXC chemokines, and hepatic regeneration had not been previously realized.

The present inventors provide the first evidence that TNF-inducible chemokines, such as ENA-78 and MIP-2, play an important role in liver repair and regeneration following injury. Data of the present invention show that ELR CXC chemokines stimulate hepatocyte proliferation in vitro and liver regeneration in vivo. Primary rat hepatocytes were isolated by collagenase digestion, exposed to incremental doses of IL-8, ENA-78, or MIP-2, and cellular proliferation measured via tritiated thymidine incorporation. These studies demonstrated significant increases in hepatocyte proliferation in response to IL-8, ENA-78, and MIP-2.

Next, rats were sacrificed in a time-dependent manner following 70% hepatectomy or sham laparotomy and hepatic tissue levels of MIP-2 and ENA-78 were measured using an ELISA. ENA-78 and MIP-2 were significantly elevated following 70% hepatectomy as compared to sham operated control animals. Rats undergoing 70% hepatectomy were then treated with neutralizing anti-ENA-78 serum, anti-MIP-2 serum, or pre-immune control serum and liver regeneration evaluated. These studies demonstrated that neutralization of ENA-78 or MIP-2 slowed the rate of liver regeneration.

These data are the first to show the importance of the CXC chemokines in the induction of hepatocyte proliferation and their importance in the in vivo regenerative and reparative responses to liver injury. In light of their present discoveries, the inventors can now also better interpret the results of earlier studies on hepatic regeneration, particularly those involving TNF.

Many types of hepatic insults are known to induce TNF release. TNF is also known to induce the release of a multitude of other mediators, including the CXC chemokines. Although certain CXC chemokines had been proposed to be important mediators in inflammation, the present invention now shows them to be central to hepatic regeneration following injury. The present invention thus provides a more meaningful biological connection for studies showing that TNF causes cellular cytokine production in vitro and induces the production of ENA-78, MIP-2 and IL-8 in rat and human hepatocytes (Colletti et al., 1996a; Mawet et al., 1996; Thornton et al., 1991).

Maruyama and colleagues (1995) have shown that relatively brief periods of hepatic ischemia accelerate hepatic regeneration following partial hepatectomy. This study demonstrated that ischemic periods of less than 60 min led to an enhanced regenerative capacity in the remaining liver following partial hepatectomy. While this study did not look at hepatic cytokine release following either ischemia or hepatectomy, other studies have documented hepatic TNF release after hepatic ischemia/reperfusion, as well as following partial hepatectomy (Satoh et al., 1991; Colletti et al., 1990a; Colletti et al., 1990b). TNF in the setting of either ischemia/reperfusion or partial hepatectomy has been demonstrated to cause ENA-78 release, which is important for hepatic neutrophil influx in both of these models (Colletti et al., 1996a; Colletti et al., 1996b).

The present invention provides a unifying concept for the foregoing studies, explaining that other TNF-induced mediators, present in hepatic injury and inflammation, also contribute to the reparative and regenerative processes in the liver. The explanation afforded by the present invention is that TNF induces the production of hepatic ELR CXC chemokines, e.g., ENA-78 and MIP-2, and that these molecules are important for hepatic repair and regeneration.

The surprising proliferative effects of ENA-78 and MIP-2 on hepatocytes are first demonstrated herein by in vitro studies. In addition, neutralization studies are presented, in which primary hepatocytes are treated with a combination of TNF and either anti-ENA-78 or anti-MIP-2 antibodies, and these also indicate that at least some of the mitogenic actions of TNF are related to upregulation of ENA-78 and/or MIP-2.

The results of the early in vivo studies herein also show that ENA-78 and MIP-2 are upregulated in response to partial hepatectomy and suggest that they are important in liver regrowth following partial hepatectomy. In these studies, neutralization of ENA-78 decreased the rate of hepatic regrowth following 70% hepatectomy; the absolute liver weights as well as the relative liver weights are significantly decreased in animals treated with anti-ENA-78 antibodies (Table 1). In treatment with anti-MIP-2 antibodies, the relative liver weights in the anti-MIP-2 treated animals are also significantly less than those in the control animals, although a similar effect is not seen for the absolute liver weights (Table 1).

There are many potential reasons for the results observed in vivo. First, this is a complex system, with many hepatic mitogens likely involved in the hepatic reparative process. Antibody-mediated neutralization of one or more of these mitogens in vivo may not have a statistically significant effect on the overall regenerative process. In addition, the ENA-78 antibodies that were available for these studies had a higher titer than those of the anti-MIP-2 antibodies. Since the in vitro studies suggest that MIP-2 may be the more potent mitogen, the availability of the lower titer anti-MIP-2 antibody to neutralize the potentially more potent mitogen may also account for the disparate results.

The CXC chemokine ELR motif is now known to be important in angiogenesis and other biological functions (Strieter et al., 1995a; 1995b; U.S. Pat. No. 5,871,723). The present invention also shows the ELR motif to be important for the induction of hepatocyte proliferation. The TVR and DLQ mutants of IL-8, engineered to be ELR negative, also suppressed the mitogenic activity of the ELR positive CXC chemokines. The present studies also suggested that the non-ELR-containing CXC chemokines may inhibit the effects of HGF, although this effect did not reach statistical significance in this study. This would expand the range of possible mechanisms beyond that of simple receptor competition.

The studies of this invention therefore provide further evidence that members of the CXC chemokine family are either promoters or suppressers of different biological activities, and that the balance between these promoters and suppressers regulates the overall activity of this family. The present data show that CXC chemokines cause hepatic mitogenesis and that the ELR motif is important in this process. IL-8 mutants block hepatocyte mitogenesis in response to the ELR-containing chemokines, ENA-78 and MIP-2. This suggests a receptor-mediated process and indicates the importance of the ELR region of the molecule in receptor binding and activation.

The IL-8 mutants fail to influence the mitogenic response to HGF, an unrelated molecule; however, the non-ELR-containing CXC chemokines did appear to have some inhibitory effects on HGF, although this effect did not reach statistical significance. The inhibitory effects of non-ELR-containing CXC chemokines on HGF may suggest alternative or additional mechanisms of action, apart from receptor competition. The possibility of a second receptor system or competitive antagonist is currently an open question.

Irrespective of the precise mechanism of action, the present invention shows that hepatic regeneration following injury is regulated through the balance of ELR-positive versus ELR-negative CXC chemokines. The invention thus provides new methods of using ELR CXC chemokines to initiate hepatic repair and regeneration.

3. CXC Chemokines in Acetaminophen Overdose Treatment

Acetaminophen is a widely used analgesic and antipyretic medication that is generally perceived to be nontoxic. However, large or repeated doses of acetaminophen cause profound liver injury (Makin and Williams, 1997), potentially leading to liver failure (Heubi et al., 1998). When consumed at doses outside the therapeutic range, or in the context of altered hepatic metabolism due to alcohol, drugs such as isoniazid (Murphy et al., 1990), viral infections, or other concurrent medical conditions, this drug can cause significant liver damage.

Despite advances in medical management, acetaminophen-induced morbidity and mortality poses a serious clinical problem for which therapeutic intervention may be limited due to the rapid clinical deterioration of the patient (Bernal et al., 1998; Makin and Williams, 1997). Acetaminophen-induced lethality in the pediatric population reached 55% in one study (Heubi et al., 1998) and acetaminophen overdose is the most common cause of acute liver failure, accounting for 20% of all patients developing liver failure in the United States (Schiodt et al., 1999) and 50–75% in the United Kingdom (Mutimer et al., 1994). As the symptoms of acetaminophen overdose often mimic common illnesses, accurate diagnoses can be elusive. Severe acute liver injury due to acetaminophen overdose thus presents a major clinical dilemma often requiring liver transplantation for the survival of the patient (Bernal et al., 1998).

The primary clinical effect of acetaminophen poisoning is hepatotoxicity that results from toxic interactions between the acetaminophen metabolite, N-acetyl-p-benzoquinoneimine, and cellular macromolecules causing the activation of liver resident cells to release toxic mediators (Lores et al., 1995; Blazka et al., 1995). Hepatocellular damage due to acetaminophen is also markedly enhanced when hepatic glutathione stores are depleted due to fasting (Whitcombe and Block, 1994). The hepatocyte is the main target of acetaminophen, and these cells typically undergo rapid necrosis that, if severe enough, can lead to the loss of liver function. To avoid this, hepatocyte division and tissue repair following acetaminophen-induced liver injury must be quickly induced (Chanda et al., 1995).

Acetaminophen overdoses are typically treated with N-acetyl-cysteine (NAC), which can prevent hepatic failure, but only if timely administered (De Groote et al., 1995). Centrilobular hepatocytes have the important role of metabolizing many of the drugs introduced into the liver (Farrell, 1997). When exposed to acetaminophen, the hepatocyte uses glutathione to neutralize the toxic effects of the N-acetyl-p-benzoquinoneimine metabolite of acetaminophen.

The toxic effects of this metabolite can be reversed with the addition of NAC, but the efficacy of NAC declines precipitously as hepatocytes succumb to the toxic effects of N-acetyl-p-benzoquinoneimine. Therefore, NAC treatment that is delayed further than 8 h after acetaminophen overdose often fails to prevent acute liver failure because this therapy does not promote the degree of hepatocyte proliferation needed to restore the liver cell mass destroyed by the toxic acetaminophen metabolite (De Groote et al., 1995; Kay and Fausto, 1997). These limitations necessitate the development of novel treatments that are efficacious beyond this limited therapeutic window (Delanty et al., 1996).

The initiation of NAC therapy is often delayed beyond the time in which NAC effectively reduces liver injury due to the aforementioned difficulties in diagnosis (Casey and Tracey, 1997). After the therapeutic window of NAC is passed, liver transplantation is often the only clinical intervention that will ensure the survival of these patients. Unfortunately, liver transplantation is costly and transplant recipients require intensive management to avoid potential complications due to rejection of the hepatic transplant (Rosen et al., 1996).

The inventors extended their primary observations regarding ELR CXC chemokine therapy to develop a novel therapeutic strategy that reduces the need for liver transplantation following acetaminophen overdose. This process utilizes the inherent regenerative processes of the liver (Kay and Fausto, 1997) by administering exogenous ELR CXC chemokines or agents that upregulate their receptors. Despite the evidence that the liver possesses a tremendous capacity to regenerate following hepatic injury, prior to the present invention, few biological substances had been identified that had appropriate stimulatory properties. In particular, substances were not known that were able to promote rapid hepatocyte proliferative responses when delivered several hours after liver injury had occurred. The present identification of agents effective enough to counteract the profound hepatic necrosis that follows acetaminophen-induced toxicity thus represents a very significant advance.

Delayed NAC treatment for acetaminophen-induced hepatotoxicity fails, in part, because this drug fails to trigger the restoration of the critical mass of hepatocytes needed for liver function. This was confirmed in the present studies by the failure of delayed NAC treatment to prevent acetaminophen-induced liver damage observed in vivo, and the decreased liver cell proliferation observed in vitro following acetaminophen challenge. Consequently, at the latter stages of drug-induced hepatotoxicity, the proliferation of the normally quiescent hepatocyte is paramount to prevent fulminant hepatic failure (Kay and Fausto, 1997).

Unfortunately, many of the factors that promote the proliferation of cultured hepatocytes do not necessarily exhibit liver regenerative effects in vivo (Fausto et al., 1995). The in vitro data presented herein show that ELR-CXC chemokines, HGF and IP-10 effectively maintain hepatocyte proliferation in the presence of toxic levels of acetaminophen. The intravenous administration of ELR-CXC chemokines and NAC immediately after acetaminophen challenge in mice is also shown to significantly reduce the histological and biochemical markers of hepatic injury.

Importantly, in comparing the therapeutic efficacy of NAC and HGF (Fausto et al., 1995) with that of ELR-CXC chemokines in mice challenged with acetaminophen, superior therapeutic effects of MIP-2, IL-8 and ENA-78 were observed 10 hours after acetaminophen challenge. Thus, the ELR-CXC chemokines were able to significantly reduce hepatotoxicity and mortality upon delayed injection into animals with acetaminophen-induced injury, whereas NAC or HGF were unable to do so. Delayed NAC or HGF treatment did not attenuate liver injury after acetaminophen challenge. This invention therefore demonstrates consistently observed hepatic regenerative properties of ELR-CXC chemokines in vitro and in vivo, and shows that ELR-CXC chemokines can reverse acetaminophen-induced liver injury and exert prominent therapeutic effects even when NAC treatment is ineffective.

As with their initial observations, the present connection between ELR CXC chemokines and liver regeneration and repair in vivo, has allowed the inventors to better interpret earlier studies. For example, the elevated levels of ELR-CXC chemokines and CXCR2 found in damaged liver tissues (Sheron et al., 1993) are no longer believed to be connected only with inflammatory processes. The de novo synthesis of ELR-CXC chemokines by hepatocytes (Takada et al., 1995) and hepatic stellate cells (Sprenger et al., 1997) was always thought to be limited to inflammatory stimuli, but this is no longer the case. The present results also explain IL-8 serum levels in alcoholism (Huang et al., 1996) and chronic hepatitis C infection (Shimoda et al., 1998).

The data of Example 1 shows that liver injury precipitated by hepatectomy is associated with dramatic increases in MIP-2 and ENA-78, the absence of which following antibody-mediated immunoneutralization significantly impairs normal liver regeneration. The precise cellular mechanism(s) by which ELR-CXC chemokines facilitate hepatocyte proliferation in response to hepatectomy and/or acetaminophen challenge are of scientific interest. However, whatever the underlying mechanism(s), the present inventors have discovered the hepatocyte regenerative properties of ELR-CXC chemokines. The invention thus provides viable methods of therapeutic intervention to postpone or altogether avoid liver transplantation, particularly in connection with acetaminophen-induced liver damage.

The present identification of ELR-CXC chemokines as possessing the therapeutic ability to overcome acute liver damage following acetaminophen challenge is further surprising in that it expands the window of treatment beyond that available with NAC. The data shown herein indicate that ELR CXC chemokines promote rapid liver regeneration even after significant drug-induced injury has occurred. There is nothing in the literature to suggest that this would be possible. Therefore, ELR-CXC chemokines, such as human IL-8 and ENA-78, have tremendous clinical potential in reducing the need for liver transplantation and the mortality associated with acetaminophen-induced fulminant liver failure.

4. CXC Chemokines in Improved Adenoviral Gene Therapy

Recombinant adenoviruses have been tested extensively in gene delivery protocols because of their ability to infect many cell types with high efficiencies in vivo (Davem and Scharschmidt, 1998). After intravenous infusion, the majority of the adenoviral vector can ultimately be found in the liver, but delivery of recombinant adenovirus in this manner elicits a powerful systemic immune response that limits gene expression and the ability to re-administer the viral vector (Huard et al., 1995; Peeters et al., 1996; Vickers et al., 1996).

Manipulation of the host immune response with potent immune suppressants is one strategy employed to eliminate the toxic effects of adenoviral vectors during liver-directed gene transfer (Yang et al., 1996; Kay et al., 1997). However, although partially effective in limiting the hepatotoxic effects of viral vectors, such techniques have other disadvantages, including the predisposition of patients to opportunistic infections (Yang et al., 1996; Kay et al., 1997; Sullivan et al., 1997).

In addition, the potential for greatly enhanced liver injury exists when analgesics are concurrently administered during hepatic gene therapy. As described above, acetaminophen is a widely used nonprescription analgesic and antipyretic that causes severe centrilobular hepatic necrosis and eventual liver failure, even in the absence of known risk factors such as pre-existing liver disease, overdose, malnourishment, or excess alcohol consumption (Kwan et al., 1995). Prior to the present invention there was an urgent need for new therapeutic strategies to prevent the hepatotoxicity following hepatic viral gene delivery and analgesic consumption.

The inventors thus turned their attention to the ELR CXC chemokines, to develop their significant therapeutic potential into the gene therapy arena. These aspects of the present invention show that ELR CXC chemokines, such as MIP-2, have beneficial in vivo effects during hepatic challenge of mice with adenovirus and/or acetaminophen.

A human type 5 replication-defective adenovirus (Ad) vector containing a MIP-2 cDNA cassette insert was employed. AdMIP-2 has previously been shown to cause increased MIP-2 expression in many tissues after its introduction into rodents (Foley et al., 1996; Bell et al., 1996). Overall, the results from these aspects of the invention demonstrate that increasing MIP-2 levels through adenovirus-mediated gene therapy has a protective and regenerative effect in the liver during acute liver injury due to adenovirus infection and acetarninophen challenge.

In these aspects of the invention, the beneficial role of MIP-2 was confirmed during hepatic adenovirus infection and acetaminophen challenge. CD1 mice that received $1 \times 10^8$ PFU of a human replication-deficient adenovirus (Ad70-3) via a tail vein injection exhibited liver injury consistent with previous studies on adenoviral gene delivery (Davern and Scharschmidt, 1998). However, when $1 \times 10^8$ PFU of an adenovirus containing a MIP-2 cDNA cassette (AdMIP-2) were introduced into CD1 mice via the same route, hepatic injury was substantially reduced.

The protective effects of MIP-2 overexpression in the adenovirus-infected liver were dramatically illustrated at the histological level. Twenty-four hours after i.v. injection, little evidence of hepatic injury was apparent following AdMIP-2 treatment in contrast to the control adenovirus Ad70-3 treatment. It was not immediately apparent how MIP-2 gene delivery via an adenoviral vector attenuated the histological injury associated with adenovirus infection, since serum levels of AST and ALT, and liver levels of KC were similar between the two groups. Further, both adenovirus treatment groups exhibited a similar hepatic proliferative response as assessed by the incorporation of [$^3$H] thymidine in whole liver homogenates. To further explore the hepatoprotective effects of AdMIP-2, additional studies were initiated to determine the hepatic response to adenoviral infection and further acute hepatic injury precipitated by acetaminophen challenge.

In immunoneutralization studies, MIP-2 was observed to be protective in mice challenged i.p. with 400 mg/kg of acetaminophen. In addition, 75% of BALB/c mice lacking the MIP-2 receptor, CXCR2, through homologous recombination were susceptible to the lethal effects of the same dose of acetaminophen. Thus, immunoneutralization of MIP-2 or the lack of CXCR2 markedly increased susceptibility to the deleterious effects of acetaminophen. AdMIP-2 pretreatment in CD1 mice challenged with acetaminophen also promoted an earlier increase in hepatic [$^3$H]thymidine incorporation when compared to Ad70-3-pretreated mice.

The protective effects of AdMIP-2 treatment prior to acetaminophen challenge are dependent upon the expression of CXCR2, as evidenced by the profound sensitivity of CXCR2ko mice to the lethal effects of acetaminophen. CXCR2ko mice appear outwardly healthy, but previous studies have demonstrated that approximately 25% of these mice exhibited granulopoesis in the periportal regions of the liver (Cacalano et al., 1994). Although CXCR2ko mice do not normally exhibit hepatic damage (Cacalano et al., 1994), the increased presence of granulocytes in the liver may partly account for the increased susceptibility of these mice to the lethal effects of acetaminophen. It should be emphasized that approximately 75% of the CXCRko mice examined in the present study died as a result of acetaminophen challenge.

CXCR2 binds a number of CXC chemokines including MIP-2, KC, granulocyte chemotactic protein-2, and neutrophil activating protein-2, but MIP-2 has been shown to exhibit the greatest affinity amongst these ligands for murine CXCR2 and exhibits a ten-fold greater affinity for this receptor than KC (Lee et al., 1995). Recent studies have shown that CXCR2-mediated events promote the regeneration of structural cells such as keratinocytes (Kulke et al., 1998), but inhibits myeloid cell proliferation (Sanchez et al., 1998). Prior to the present invention, little was known about the role of CXCR2 in hepatocyte regeneration. The data presented herein suggest that a paucity of CXCR2 in the liver is associated with severe hepatocyte necrosis following acetaminophen challenge. The inventors thus propose that CXCR2 expression has an important, role in hepatocyte survival and replication following adenovirus and/or acetaminophen challenge.

The effect of AdMIP-2 pretreatment in the liver was further explored in adenovirus-infected mice challenged with acetaminophen. In Ad70-3-pretreated mice, the administration of acetaminophen resulted in the death of 50% of these mice by 24 h. A similar acetaminophen challenge in AdMIP-2-pretreated mice resulted in an overall mortality rate of only 10%. The survival of AdMIP-2-pretreated mice challenged with acetaminophen was also reflected in a CXCR2-dependent reduction in histological injury, serum levels of AST and ALT, and liver levels of KC.

The early augmentation of the proliferative response of liver cells in AdMIP-2 pretreated mice may explain why only 10% of these mice died, whereas 50% of Ad70-3-pretreated mice died following exposure to acetaminophen. Thus, MIP-2 appears to maintain hepatic integrity following acetaminophen challenge by facilitating the regeneration of hepatocytes.

In contrast to previous studies using AdMIP-2 to overexpress MIP-2 in the lung (Foley et al., 1996) and brain (Bell et al., 1996), AdMIP-2 delivery to the liver via an i.v. injection did not markedly augment neutrophil accumulation in hepatic tissue as determined by histology and MPO activity. The protective effects of MIP-2 during adenovirus infection and acetaminophen challenge are thus not mediated by increased neutrophil recruitment into the liver.

The seeming discrepancy between the present studies and previous observations pertaining to AdMIP-2 infection in lung (Foley et al., 1996) and brain (Bell et al., 1996), where neutrophil recruitment was markedly increased in both tissues for up to 7 days after virus injection, may relate to differences in the amount or the route of AdMIP-2 administration. However, it is interesting to note that constitutive levels of MIP-2 are present in liver homogenates from untreated mice, and neutrophils are present in the liver under normal conditions. Intravenous administration of AdMIP-2 may then disrupt the chemotactic gradient required in the liver to facilitate neutrophil infiltration.

Another putative explanation for the protective effect of AdMIP-2 may relate to the direct modulatory effects of MIP-2 on neutrophils or other inflammatory processes. Thus, increased MIP-2 may exert an anti-inflammatory effect in the acutely damaged liver, which reduces the need for infiltration of inflammatory cells prior to hepatic restoration or regeneration.

Irrespective of the underlying mechanism(s), the present data demonstrate that overexpression of ELR CXC chemokines, such as MIP-2, protects the liver from adenovirus infection and acetaminophen challenge, by facilitating rapid hepatic regeneration. The identification of regenerative roles for ELR CXC chemokines in the liver represents a breakthrough in both liver treatment and chemokine biology.

The invention thus provides the use of ELR-containing CXC chemokines, particularly human chemokines, in any hepatoprotective strategy, particularly those aimed at facilitating hepatic regeneration and survival following acute hepatic injury in the clinical setting. In addition, as the potential for hepatic complications and mortality is markedly enhanced during the combination of hepatic gene therapy and the intake of acetaminophen, the present invention is ideally suited for use in such instances. As this invention abrogates the combined toxic effects of both agents in the liver, it therefore greatly broadens the therapeutic potential of adenovirus-based hepatic gene therapy.

5. Mechanism of ELR CXC Chemokine-induced Hepatocyte Proliferation

The present invention shows that ELR CXC chemokines, such as MIP-2, have therapeutic effects against acetaminophen toxicity in vivo, even when NAC treatment is ineffective. The inventors further show that ELR CXC chemokines, such as MIP-2, and the CXCR2 receptor are integral for the accelerated progression of quiescent hepatocytes into the cell cycle following an acetaminophen challenge in mice.

In particular, Example IV shows that exogenous MIP-2 promotes a marked acceleration of hepatocyte proliferation in acetaminophen-challenged liver that is due to its effect on the nuclear translocation of liver-enriched transcription factors, such as C/EBP-$\beta$ and STAT-3, which are necessary for hepatocyte proliferation. Conversely, the immunoneutralization of endogenous MIP-2 or CXCR2 during acetaminophen challenge markedly aggravates hepatic injury, reduces hepatocyte proliferation and blocks the nuclear translocation of C/EBP-$\beta$ and STAT-3.

TNF-$\alpha$ and IL-6 are two cytokines that possess unique liver regenerative properties (Cressman et al., 1996). IL-6 initiates hepatocyte proliferation through the nuclear translocation of signal transducer and activator of transcription-3 (STAT-3), whereas TNF-$\alpha$ regulates nuclear levels of at least two families of transcription factors in proliferating hepatocytes (Akerman et al., 1992; Diehl et al., 1995). In addition to nuclear translocation of STAT-3, IL-6 also induces tyrosine phosphorylation of Janus kinases and (Zhong et al., 1994), an early event during liver regeneration (Cressman et al., 1995). While there are some transcription factors are dependent on the expression of IL-6, there are others that are normal in its absence. For example, IL-6 knockout animals have decreased expression of STAT-3, yet normal expression of C/EBP-$\beta$ (Cressman et al., 1996; Taub et al., 1999). Similar to STAT-3, C/EBP-$\beta$ is involved in regeneration pathways, yet the mechanism in which it is activated during liver regeneration is unknown.

While liver regeneration is impaired in C/EBP-$\beta$ knockout mice, the genes associated with regeneration that are affected are distinct from those regulated by IL-6 (Greenbaum et al., 1998). TNF-$\alpha$ may be involved since it is upregulated following PH and immunoneutralization inhibits liver regeneration (Yamada et al., 1997; Rai et al., 1997) possibly due to the decreased expression of the C/EBPs (Diehl et al., 1994; Diehl et al., 1995). Thus, TNF-α and IL-6 are involved in the initiation of regeneration pathways including the activation of liver-enriched-transcription factors such as STAT-3 and C/EBP-β. These two factors activate immediate early genes and cyclins causing progression of the cell cycle through the G1 phase and into the DNA synthetic phase (Taub et al., 1999).

Example IV shows that MIP-2 is actively involved in hepatocyte proliferation, which effects may be either downstream or independent of IL-6 or TNF-α. While there were dramatic elevations in nuclear expression of STAT3 in response to MIP-2 treatment, IL-6 was never significantly elevated in either the serum or the liver in response to MIP-2 treatment as compared to controls. Furthermore, MIP-2 is an effective therapeutic treatment in IL-6 knockout as revealed by its dramatic decrease of AST and ALT levels.

Other ELR-CXC chemokines have been shown to induce acute phase proteins (Wigmore et al., 1997) that are regulated by STAT-3 (Zhang et al., 1996), but not dependent on IL-6 production. While TNF-α plays a role in hepatocyte proliferation, TNF-α also induces a multitude of other mediators. For example, elevation of TNF-α in the liver promotes the production of ELR-containing CXC chemokines including ENA-78 and KC (Colletti et al., 1996). Likewise, in the present study, TNF-α was elevated in the liver of acetaminophen-challenged mice, but not the serum at 24 hrs. after MIP-2 treatment, but at no other time point examined. Yet, TNF-α appeared to act synergistically with MIP-2 because when TNF-α was immunoneutralized concomitantly with exogenous MIP-2 treatment the acetaminophen-challenge lethal.

The data presented in Example IV clearly show that MIP-2 treatment rapidly promoted the nuclear expression of C/EBP-β approximately 30 h prior to that of saline-treated animals and consistently upregulated nuclear expression of STAT-3 at all time points examined. Hepatocytes of MIP-2 treated animals began to enter the GI phase as seen by the increased Cyclin D1 expression at 24 h as compared to control animals and by 48 h, the hepatocytes entered the S-phase as seen by ten-fold increase in BrdU incorporation. Likewise, endogenous MIP-2 was necessary for baseline proliferation after acetaminophen toxicity.

When MIP-2 activity was diminished, either by immunoneutralization of the ligand or receptor, the nuclear expression of C/EBP-β, STAT-3, and cyclin D1 were dramatically reduced. Furthermore, there was a five-fold reduction in the baseline BrdU labeling. However, when MIP-2 was neutralized, other CXCR2 ligands could be having an effect. The present invention also shows that other CXCR2 ligands, such as IL-8 and ENA-78 have an effect on hepatocyte proliferation (Hogaboam et al., 1999a; Colletti et al., 1998). This explains the finding that the neutralization of CXCR2 had a more dramatic effect on the diminished levels of transcription factors and cyclin D1, ultimately compromising the survival of the animals due to the complete abolishment of all CXCR2 ligands.

Enforced overexpression of C/EBP-α has been shown to inhibit proliferation in several different hepatocyte cell lines (Hendricks-Taylor et al., 1995; Watkins et al., 1996; Diehl et al., 1996). Additionally, C/EBP-α has been shown to regulate the production of different isoforms of C/EBP-β and consequently C/EBP-α knockout animals predominantly expressing the 38- and 35-kd LAP isoforms (Burgess-Beusse et al., 1999). Eight hrs. after MIP-2 treatment, C/EBP-α was more dominantly expressed in this group of mice and by 24 h after treatment, C/EBP-α nuclear expression was diminished presumably due to the entrance into the cell cycle (i.e. increased cyclin D1 expression). In contrast, control mice exhibited low levels of C.EBP-α at 8 h after treatment and expression increased by 24 h. At the earlier time points, saline-treated animals did not be express C/EBP-α presumably due to the fact that their hepatocytes were damaged. By the time that hepatocytes in saline-treated mice had begun to express C/EBP-α again, the hepatocytes of MIP-2-treated animals appeared to have begun to decrease their C/EBP-α expression, in order to exit the quiescent stage of the cell cycle. Thus, these data suggest that MIP-2 supplies a unique mitogenic signal to the liver that permits the rapid recovery from acetaminophen toxicity.

In summary, these aspects of the present invention demonstrate the role of endogenous and exogenous ELR CXC chemokines, such as MIP-2, in hepatocyte proliferation in vivo in art-accepted murine models of acetaminophen toxicity. MIP-2 rapidly upregulates nuclear transcription factors, STAT3, C/EBP-β, and C/EBP-α, resulting in the regeneration of the acutely damaged liver. Thus, CXCR2-dependent CXC chemokines have tremendous therapeutic potential in acetaminophen-induced liver failure and fulminant hepatic failure.

6. Therapeutic Effect of IP-10, a Non-ELR CXC Chemokine, by Upregulating CXCR2

IP-10 (β-interferon-inducible protein-10) is a non-ELR-CXC chemokine, the role of which in liver injury is controversial. In fact, there is no consensus in the art as to the role of IP-10 in hepatic injury and recovery. Most studies have reported that IP-10 elevation is correlated to liver injury. Enhanced IP-10 levels have been detected during liver injury due to an adenoviral challenge in mice (Muruve et al., 1999). Other studies have reported that elevated IP-10 levels correlate with the histological findings in biliary atresia patients (Kobayashi et al., 1999). Additionally, lymphocytes infiltrating hepatitis C infected patients expressed CXCR3, the receptor for IP-10, and IP-10 was upregulated on sinsuoidal epithelium (Narumi et al., 1997).

In contrast, recent studies of certain of the present inventors have found that increased IP-10 levels correlate with less liver injury. When IP-10 was elevated in response to IFN-γ treatment, there was less injury in an ischemia-reperfusion model as shown by a decrease in ALT values (present invention and Colletti et al., 2000). Such studies indicate some hepato-beneficial effects attributable to IP-10, but contrast with the work reported earlier (Muruve et al., 1999; Kobayashi et al., 1999; Narumi et al., 1997).

Despite both the confusion in the art of liver injury and the classic demarcation between the effects of ELR and non-ELR CXC chemokines in other functional studies, the present inventors contemplated that IP-10 may have a positive role in acetaminophen-induced liver injury. The studies in Example V elucidate the role of IP-10 in acetaminophen-induced liver injury by examining the expression pattern of IP-10 and its receptor CXCR3 during an acetaminophen-challenge. It is shown that IP-10 is elevated during acetaminophen-challenge and that its elevation corresponds to the elevation in alanine amimotransferase (ALTs). These aspects of the invention further show that, surprisingly, maintaining elevated levels of the non-ELR chemokine IP-10 ten hours after an acetaminophen-challenge is beneficial. The benefits in reducing liver injury are exerted through promoting the expression of CXCR2, the receptor for ELR chemokines, such as MIP-2, on hepatocytes.

IP-10 has previously been shown to be related to various types of liver injury. In Example V, the inventors examined, for the first time, the role of IP-10 in acetaminophen-induced liver injury. IP-10 levels were elevated in the serum and its receptor, CXCR3, was elevated in the liver after acetaminophen-challenge. When exogenous IP-10 was given 10 h after acetaminophen challenge there was a marked improvement in liver enzymes and the histological appearance of the liver was dramatically improved.

Furthermore, IP-10 post-treatment elevated the expression of CXCR2 on hepatocytes, the receptor for the hepatoregenerative factor MIP-2, and the levels of MIP-2 in the serum, which the invention earlier shows to play a central role in recovery from acetaminophen-induced toxicity. Although the link between IP-10 and the CXCR2 receptor is compelling, irrespective of whether these observations form are only part of the mechanism of IP-10 actions, the beneficial effects of IP-10 post-treatment are clearly evident. The findings of Example V therefore extend the application of the present invention to the treatment of liver injury using non-ELR CXC chemokines.

7. Nucleic Acid Segments

Any operative CXC chermokine protein, nucleic acid or recombinant vector, preferably an ELR CXC chemokine or IP-10 protein, nucleic acid or recombinant vector, may be used in the present invention. Techniques for creating and using recombinant CXC chemokines and host cells that express such molecules, through the application of DNA technology, will be known to those of ordinary skill in the art in light of the present disclosure.

As used herein, the terms CXC chemokine "nucleic acid segment" and "DNA segment" refer to nucleic acid and DNA molecules that have been isolated free from total genomic nucleic acids or DNA of a particular species. Therefore, a DNA segment encoding a CXC chemokine refers to a DNA segment that contains wild-type, polymorphic, variant or mutant CXC chemokine coding sequences isolated away from, or purified free from, total genomic nucleic acids or DNA. Included within the terms "nucleic acid and DNA segment", are nucleic acids and DNA segments and smaller fragments of such segments, and also recombinant vectors, including, for example, plasmids, cosmids, phage, viruses, and the like.

A nucleic acid or DNA segment comprising an isolated or purified wild-type, polymorphic, variant or mutant CXC chemokine gene refers to a nucleic acid or DNA segment including coding sequences and, in certain aspects, regulatory sequences, isolated substantially away from other naturally occurring genes or protein encoding sequences. In this respect, the term "gene" is used for simplicity to refer to a functional CXC chemokine-encoding unit. As will be understood by those in the art, this functional term includes both genomic sequences, cDNA sequences and smaller engineered gene segments that express, or may be adapted to express, operative CXC chemokine proteins, polypeptides, domains, peptides, fusion proteins and mutants. Where "gene" is intended to encompass genomic regulatory or non-coding sequences this will be stated.

"Isolated substantially away from other coding sequences" means that the CXC chemokine nucleic acid or DNA segment forms the significant part of the coding region, and that the overall nucleic acid segment does not contain large portions of naturally-occurring nucleic acids or DNA, such as large chromosomal fragments or other functional genes or cDNA coding regions. Of course, this refers to the nucleic acid or DNA segment as originally isolated, and does not exclude genes, coding regions and/or regulatory elements later added to the segment by the hand of man.

ELR-containing CXC chemokines for use in the invention include MIP-2, ENA-78, IL-8, KC, GCP-2, NAP-2, CTAP-III, βTG, GRO-α, GRO-β and GRO-γ. As described above, ELR CXC chemokines for use in the invention are exemplified by those in Table A and in U.S. Pat. No. 5,871,723; application Ser. No. 09/213,383, all of which sequences are specifically incorporated herein by reference. The preferred non-ELR CXC chemokine is IP-10, which is also exemplified in Table A and in U.S. Pat. No. 5,871,723; application Ser. No. 09/213,383, all of which sequences are specifically incorporated herein by reference.

CXC chemokine nucleic acid and DNA segments and recombinant vectors incorporating such DNA sequences may encode CXC chemokines that include amino acid sequences essentially as set forth in any of the foregoing CXC chemokine sequences. Sequences "essentially as set forth in" mean that the sequences substantially correspond to an active portion of a CXC chemokine and have relatively few amino acids that are not identical to, or a biologically functional equivalent of, such sequences.

The term "biologically functional equivalent" is well understood in the art and is further defined in detail herein. Accordingly, sequences that have between about 70% and about 80%; or more preferably, between about 81% and about 89%; or more preferably, between about 90% and about 94%; or even more preferably, between about 95% and about 99%; of amino acids that are identical or functionally equivalent to the amino acid sequences of the CXC chemokines will be sequences that are "essentially as set forth in a CXC chemokine sequence". Sequences of about 90%, 91%, 92%, 93%, 94%, 95%, 96%, 97%, 98% or 99% sequence identity or functionally equivalency to the CXC chemokines will often be preferred.

The biological activity of a functionally equivalent protein should naturally be maintained. Such may be readily determined by any one of a number of functional assays, as known to those of ordinary skill in the art and exemplified by the detailed studies herein.

The DNA segments and recombinant vectors for use in the invention may include within their sequence a nucleic acid sequence essentially as set forth in a CXC chemokine sequence. The term "essentially as set forth in a CXC chemokine sequence" is used in the same sense as described above and means that the nucleic acid sequence substantially corresponds to a portion of a CXC chemokine nucleic acid sequence and have relatively few codons that are not identical, or functionally equivalent, to the codons of a CXC chemokine sequence. The term "functionally equivalent codon" is used herein to refer to codons that encode the same amino acid, such as the six codons for arginine or serine, and also refers to codons that encode biologically equivalent amino acids (see Table B).

TABLE B

| Amino Acids | | | DNA Codons | | | |
|---|---|---|---|---|---|---|
| | | | | Codons | | |
| Alanine | Ala | A | GCC | GCT | GCA | GCG |
| Cysteine | Cys | C | TGC | TGT | | |
| Aspartic acid | Asp | D | GAC | GAT | | |
| Glutamic acid | Glu | E | GAG | GAA | | |
| Phenylalanine | Phe | F | TTC | TTT | | |

TABLE B-continued

DNA Codons

| Amino Acids | | | Codons | | | | | |
|---|---|---|---|---|---|---|---|---|
| Glycine | Gly | G | GGC | GGG | GGA | GGT | | |
| Histidine | His | H | CAC | CAT | | | | |
| Isoleucine | Ile | I | ATC | ATT | ATA | | | |
| Lysine | Lys | K | AAG | AAA | | | | |
| Leucine | Leu | L | CTG | CTC | TTG | CTT | CTA | TTA |
| Methionine | Met | M | ATG | | | | | |
| Asparagine | Asn | N | AAC | AAT | | | | |
| Proline | Pro | P | CCC | CCT | CCA | CCG | | |
| Glutamine | Gln | Q | CAG | CAA | | | | |
| Arginine | Arg | R | CGC | AGG | CGG | AGA | CGA | CGT |
| Serine | Ser | S | AGC | TCC | TCT | AGT | TCA | TCG |
| Threonine | Thr | T | ACC | ACA | ACT | ACG | | |
| Valine | Val | V | GTG | GTC | GTT | GTA | | |
| Tryptophan | Trp | W | TGG | | | | | |
| Tyrosine | Tyr | Y | TAC | TAT | | | | |

It will also be understood that amino acid and nucleic acid sequences may include additional residues, such as additional N- or C-terminal amino acids or 5' or 3' sequences, and yet still be essentially as set forth in a CXC chemokine sequence, so long as the sequence meets the criteria set forth above, including the maintenance of functional biological activity. The addition of terminal sequences as applied to nucleic acid sequences includes, for example, the addition of various regulatory or other non-coding or coding sequences flanking either of the 5' or 3' portions of the coding region.

Excepting flanking regions, and allowing for the degeneracy of the genetic code, sequences that have between about 70% and about 79%; or more preferably, between about 80% and about 89%; or more preferably, between about 90% and about 94%; or even more preferably, between about 95% and about 99%; of nucleotides that are identical to the nucleotides of a CXC chemokine sequence will be sequences that are "essentially as set forth in a CXC chemokine sequence". Substantially full length coding sequences of about 90%, 91%, 92%, 93%, 94%, 95%, 96%, 97%, 98% or 99% sequence identity to such nucleotide sequences will often be preferred.

Sequences that are essentially the same as those set forth in a CXC chemokine sequence may also be functionally defined as sequences that are capable of hybridizing to a CXC chemokine nucleic acid segment under appropriately (relatively) stringent conditions. Suitable appropriately or relatively stringent hybridization conditions will be well known to those of skill in the art in light of the present disclosure.

The CXC chemokine nucleic acid segments for use in the present invention, regardless of the length of the coding sequence itself, may be combined with other nucleic acid and DNA sequences, such as promoters, polyadenylation signals, additional restriction enzyme sites, multiple cloning sites, other coding segments, and the like, such that their overall length may vary considerably. It is therefore contemplated that a nucleic acid segment of almost any length may be employed, with the total length preferably being limited by the ease of preparation and use in the intended recombinant protocol.

CXC chemokine sequences and recombinant vectors may also variously include coding regions bearing selected alterations or modifications in the basic coding region, or they may encode larger polypeptides that nevertheless include such coding regions or may encode biologically functional equivalent proteins or peptides that have variant amino acids sequences.

The nucleic acid and DNA segments for use in the present invention therefore encompass biologically functional equivalent CXC chemokines that arise as a consequence of codon redundancy and functional equivalency that are known to occur naturally within nucleic acid sequences and the proteins thus encoded. Equally, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques.

8. Biological Functional Equivalents

As modifications and changes may be made in the structure of CXC chemokine nucleic acids and proteins for use in the present invention, and still obtain molecules having like or otherwise desirable characteristics, such biologically functional equivalents are also encompassed within the present invention.

For example, certain amino acids may be substituted for other amino acids in a protein structure without appreciable loss of interactive binding capacity, for example, interaction with cell surface receptors. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. It is thus contemplated that various changes may be made in the sequence of CXC chemokines, or their underlying DNA, without appreciable loss of their biological utility or activity.

In terms of functional equivalents, it is well understood by the skilled artisan that, inherent in the definition of a "biologically functional equivalent protein or peptide or gene", is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted.

In particular, where shorter active polypeptides are concerned, it is contemplated that fewer amino acid substitutions should be made within the given polypeptide. Longer proteins and polypeptides may have an intermediate number of changes. The full length proteins will have the most tolerance for a larger number of changes. Of course, a plurality of distinct proteins/polypeptides with different substitutions may easily be made and used in accordance with the invention.

It is also well understood that where certain residues are shown to be particularly important to the biological or structural properties of a protein or peptide, such residues may not generally be exchanged. The ELR and CXC sequences of an ELR CXC chemokine clearly must be maintained. Maintenance of biological structure/function can always be easily tested, for example, using one or more of the in vitro and in vivo assays disclosed herein in detail, and by antibody binding. Tests of immunological cross-reactivity are a straightforward matter and can be readily determined using specific assays, i.e., based upon immuno-competition assays.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biological functional equivalent protein or peptide thereby created is intended for use in immunological embodiments, as in certain embodiments of the present invention. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. A table of amino acids and their codons is presented herein for use in such embodiments, as well as for other uses, such as in the design of probes and primers and the like.

9. Mutagenesis

Site-specific mutagenesis is a technique useful in the preparation of individual polypeptides, or biologically functional equivalent proteins or polypeptides, through specific mutagenesis of the underlying DNA. The technique further provides a ready ability to prepare and test sequence variants by introducing one or more nucleotide sequence changes into the DNA. U.S. Pat. No. 4,888,286 is specifically incorporated herein by reference to further exemplify such processes.

Site-specific mutagenesis allows the production of mutants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

Techniques of site-specific mutagenesis are well known in the art. Certain techniques typically employ a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector that includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as $E.$ $coli$ polymerase I Kienow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as $E.$ $coli$ cells, and clones are selected that include recombinant vectors bearing the mutated sequence arrangement.

The preparation of sequence variants of CXC chemokines using site-directed mutagenesis described above is provided as a means of producing potentially useful species and is not meant to be limiting, as there are other ways in which sequence variants of CXC chemokines may be obtained. For example, recombinant vectors encoding the desired gene may be treated with mutagenic agents, such as hydroxylamine, to obtain sequence variants.

Although the foregoing methods are suitable for use in mutagenesis, the use of PCR is generally now preferred. This technology offers a quick and efficient method for introducing desired mutations into a given DNA sequence. The following text particularly describes the use of PCR to introduce point mutations into a sequence, as may be used to change the amino acid encoded by the given sequence. Adaptations of this method are also suitable for introducing restriction enzyme sites into a DNA molecule.

In this method, synthetic oligonucleotides are designed to incorporate a point mutation at one end of an amplified segment. Following PCR, the amplified fragments are blunt-ended by treating with Klenow fragments, and the blunt-ended fragments are then ligated and subcloned into a vector to facilitate sequence analysis.

To prepare the template DNA that one desires to mutagenize, the DNA is subcloned into a high copy number vector, such as pUC19, using restriction sites flanking the area to be mutated. Template DNA is then prepared using a plasmid miniprep. Appropriate oligonucleotide primers that are based upon the parent sequence, but which contain the desired point mutation and which are flanked at the 5' end by a restriction enzyme site, are synthesized using an automated synthesizer. It is generally required that the primer be homologous to the template DNA for about 15 bases or so. Primers may be purified by denaturing polyacrylamide gel electrophoresis, although this is not absolutely necessary for use in PCR. The 5' end of the oligonucleotides should then be phosphorylated.

The template DNA should be amplified by PCR, using the oligonucleotide primers that contain the desired point mutations. The concentration of $MgCl_2$ in the amplification buffer will generally be about 15 mM. Generally about 20–25 cycles of PCR should be carried out as follows: denaturation, 35 sec. at 95° C.; hybridization, 2 min. at 50° C.; and extension, 2 min. at 72° C. The PCR will generally include a last cycle extension of about 10 min. at 72° C. After the final extension step, about 5 units of Kienow fragments should be added to the reaction mixture and incubated for a further 15 min. at about 30° C. The exonuclease activity of the Kienow fragments is required to make the ends flush and suitable for blunt-end cloning.

The resultant reaction mixture should generally be analyzed by nondenaturing agarose or acrylamide gel electrophoresis to verify that the amplification has yielded the predicted product. One would then process the reaction mixture by removing most of the mineral oils, extracting with chloroform to remove the remaining oil, extracting with buffered phenol and then concentrating by precipitation with 100% ethanol. Next, one should digest about half of the amplified fragments with a restriction enzyme that cuts at the flanking sequences used in the oligonucleotides. The digested fragments are purified on a low gelling/melting agarose gel.

To subclone the fragments and to check the point mutation, one would subclone the two amplified fragments into an appropriately digested vector by blunt-end ligation. This would be used to transform *E. coli*, from which plasmid DNA could subsequently be prepared using a miniprep. The amplified portion of the plasmid DNA would then be analyzed by DNA sequencing to confirm that the correct point mutation was generated. This is important as Taq DNA polymerase can introduce additional mutations into DNA fragments.

The introduction of a point mutation can also be effected using sequential PCR steps. In this procedure, the two fragments encompassing the mutation are annealed with each other and extended by mutually primed synthesis. This fragment is then amplified by a second PCR step, thereby avoiding the blunt-end ligation required in the above protocol. In this method, the preparation of the template DNA, the generation of the oligonucleotide primers and the first PCR amplification are performed as described above. In this process, however, the chosen oligonucleotides should be homologous to the template DNA for a stretch of between about 15 and about 20 bases and must also overlap with each other by about 10 bases or more.

In the second PCR amplification, one would use each amplified fragment and each flanking sequence primer and carry PCR for between about 20 and about 25 cycles, using the conditions as described above. One would again subclone the fragments and check that the point mutation was correct by using the steps outlined above.

In using either of the foregoing methods, it is generally preferred to introduce the mutation by amplifying as small a fragment as possible. Of course, parameters such as the melting temperature of the oligonucleotide, as will generally be influenced by the GC content and the length of the oligo, should also be carefully considered. The execution of these methods, and their optimization if necessary, will be known to those of skill in the art, and are further described in various publications, such as *Current Protocols in Molecular Biology*, 1995, incorporated herein by reference.

10. Recombinant Vectors, Host Cells and Expression

Recombinant vectors expressing CXC chemokines may also be used in the present invention. The terms "recombinant vector, expression vector or construct" mean any type of genetic construct containing a nucleic acid coding for an expressed product in which part or all of the nucleic acid encoding sequence is capable of being transcribed. In preferred embodiments, "expression" includes both transcription of a nucleic acid segment and translation of an mRNA into a gene product.

Particularly useful vectors are contemplated to be those vectors in which the coding portion of the nucleic acid or DNA segment, whether encoding a full length protein or smaller polypeptide, is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned", "under control" or "under transcriptional control" mean that the promoter is in the correct location and orientation in relation to the nucleic acid segment to control RNA polymerase initiation and expression of the nucleic acid segment.

The promoter may be in the form of the promoter that is naturally associated with a CXC chemokine, as may be obtained by isolating the 5' non-coding sequences located upstream of the coding segment, for example, using recombinant cloning and/or PCR technology, in connection with the compositions disclosed herein. PCR technology is disclosed in U.S. Pat. No. 4,683,202 and U.S. Pat. No. 4,682,195, each incorporated herein by reference.

In other embodiments, certain advantages will be gained by positioning the coding nucleic acid or DNA segment under the control of a recombinant, or heterologous, promoter. As used herein, a recombinant or heterologous promoter refers to a promoter that is not normally associated with a CXC chemokine in its natural environment. Such promoters may include promoters normally associated with other nucleic acids and genes, and/or promoters isolated from any other bacterial, viral, eukaryotic, or mammalian cell.

Naturally, it will be important to employ a promoter that effectively directs the expression of the nucleic acid or DNA segment in the cell type or organism chosen for expression. The use of promoter and cell type combinations for protein expression is generally known to those of skill in the art of molecular biology, for example, see Sambrook et al. (1989; incorporated herein by reference). The promoters employed may be constitutive, or inducible, and can be used under the appropriate conditions to direct high level expression of the introduced nucleic acid or DNA segment, such as is advantageous in the large-scale production of recombinant proteins or peptides.

At least one module in a promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid of the invention is not believed to be critical, so long as it is capable of expressing the nucleic acid in the targeted cell. Thus, where a mammalian or human cell is targeted, it is preferable to position the nucleic acid coding region adjacent to and under the control of a promoter that is capable of being expressed in a mammalian or human cell. Generally speaking, such a promoter might include either a mammalian, human or viral promoter. Exemplary promoters include those derived from HSV and tetracycline controlled promoters.

In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters that are well-known in the art to achieve expression of a transgene are contemplated as well, provided that the levels of expression are sufficient for a given purpose. Virtually any element/promoter may be employed in the context of the present invention to regulate the CXC chemokine expression.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a transgene of the invention. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Once suitable CXC chemokine clones have been obtained, one may proceed to prepare an expression system. The engineering of DNA segment(s) for expression in a prokaryotic or eukaryotic system may be performed by techniques known to those of skill in recombinant expression. It is believed that virtually any expression system may be employed in the expression of the proteins of the present invention.

In expression, one will typically include a polyadenylation signal to effect proper polyadenylation of the transcript. The nature of the polyadenylation signal is not believed to be crucial to the successful practice of the invention, and any such sequence may be employed. The SV40 polyadenylation signal is convenient and is known to function well in various target cells. Also contemplated as an element of the expression cassette is a terminator. These elements can serve to enhance message levels and to minimize read through from the cassette into other sequences.

A specific initiation signal also may be required for efficient translation of coding sequences. These signals include the ATG initiation codon and adjacent sequences. Exogenous translational control signals may be used. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

The CXC chemokines for use in the present invention may be co-expressed with any other protein or peptide, such as another hepatocyte growth factor. Co-expression may be achieved by co-transfecting the cell with two distinct recombinant vectors, each bearing a copy of either the respective DNA. Alternatively, a single recombinant vector may be constructed to include the coding regions for both of the proteins, which could then be expressed in cells transfected with the single vector. In either event, the term "co-expression" herein refers to the expression of a CXC chemokine with another protein or peptide in the same recombinant cell.

As used herein, the terms "engineered" and "recombinant" cells refer to a cell into which an exogenous nucleic acid or DNA segment has been introduced. Therefore, engineered cells are distinguishable from naturally occurring cells, which do not contain a recombinantly introduced exogenous nucleic acid or DNA segment. Engineered cells are thus cells having a nucleic acid or DNA segment introduced through the hand of man. Recombinant cells also include those having an introduced nucleic acid or DNA segment positioned adjacent to a promoter not naturally associated with the particular introduced nucleic acid or DNA segment.

To express a recombinant CXC chemokine in accordance with the invention one would prepare an expression vector that comprises a CXC chemokine-encoding nucleic acid under the control of one or more promoters. To bring a coding sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli, H. pylori* and *B. subtilis* transformed with recombinant bacteriophage DNA, plasmid DNA or cosmid DNA expression vectors.

Certain examples of prokaryotic hosts are *E. coli* strain RR1, *E. coli* LE392, *E. coli* B, *E. coli* X 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium, Serratia marcescens*, and various Pseudomonas species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector that can be used to transform host cells, such as *E. coli* LE392.

Further useful vectors include pIN vectors; and pGEX vectors, for use in generating glutathione S-transferase (GST) soluble fusion proteins for later purification and separation or cleavage. Other suitable fusion proteins are those with β-galactosidase, ubiquitin, and the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in Saccharomyces, the plasmid YRp7, for example, is commonly used. This plasmid already contains the trp1 gene, which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing CXC chemokine coding sequences.

In a useful insect system, *Autograph californica* nuclear polyhedrosis virus (AcNPV) is used as a vectorgto express foreign genes. The virus grows in *Spodoptera frugiperda* cells. The CXC chemokine coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051, incorporated herein by reference).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications and processing (e.g., cleavage) of protein products may be important for the function of the protein.

Different host cells have characteristic and specific mechanisms for the post-translational processing and modification of proteins. Appropriate cells lines or host systems can be chosen to ensure the correct modification and processing of the foreign protein expressed.

Expression vectors for use in mammalian such cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient. The promoters may be derived from the genome of mammalian cells (e.g., metallothionein promoter) or from mammalian viruses (e.g., the adenovirus late promoter; the vaccinia virus 7.5K promoter).

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment that also contains the SV40 viral origin of replication. Smaller or larger SV40 fragments may also be used, provided there is included the approximately 250 bp sequence extending from the HindIII site toward the BglI site located in the viral origin of replication.

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of recombinant CXC chemokines, stable expression may be used and cell lines that stably express CXC chemokines may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited, to the herpes simplex virus thymidine kinase, hypoxanthine-guanine phosphoribosyltransferase and adenine phosphoribosyltransferase genes, in tk-, hgprt- or aprt-cells, respectively. Also, antimetabolite resistance can be used as the basis of selection for dhfr, which confers resistance to methotrexate; gpt, which confers resistance to mycophenolic acid; neo, that confers resistance to the aminoglycoside G-418; and hygro, which confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth). Non-anchorage dependent or suspension cultures from continuous established cell lines are the most widely used means of large scale production of cells and cell products. However, suspension cultured cells have limitations, such as tumorigenic potential and lower protein production than adherent cells.

CXC chemokines for use in the invention may be "overexpressed", i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein or peptide in comparison to the level in natural cells is indicative of overexpression, as is a relative abundance of the specific protein in relation to the other proteins produced by the host cell and, e.g., visible on a gel.

11. Gene Therapy and Adenoviral Constructs

The CXC chemokine therapies of the present invention may be achieved using any form of gene therapy. Retroviruses have promise as gene delivery vectors due to their ability to integrate their genes into the host genome, transferring a large amount of foreign genetic material, infecting a broad spectrum of species and cell types and of being packaged in special cell-lines. Other viruses, such as herpes simplex viruses (HSV), cytomegalovirus (CMV), and adeno-associated virus (AAV), such as those described by U.S. Pat. No. 5,139,941, incorporated herein by reference, may also be engineered to serve as vectors for gene transfer.

In certain embodiments, an HSV gene therapy vector may be used. A factor that makes HSV an attractive vector is the size and organization of the genome. As HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations. HSV also is relatively easy to manipulate and can be grown to high titers. Thus, delivery is less of a problem, both in terms of volumes needed to attain sufficient MOI and in a lessened need for repeat dosings.

As discussed in detail herein, the present invention is particularly suitable for use with adenoviral gene therapy. Adenoviruses do not integrate their genetic material into the host genome and therefore do not require host replication for gene expression, making them ideally suited for rapid, efficient, heterologous gene expression. Adenoviral vectors expressing or co-expressing CXC chemokines may be employed to advantage using the present invention. Techniques for preparing replication-defective infective viruses are well known in the art.

Adenovirus vectors, and preferably replication defective vectors, are particularly useful in the context of the present invention. Replication defective vectors may be generated by deleting the viral early region 1 (E IA) region such that the virus is competent to replicate only in cells, such as human 293 cells, which express adenovirus early region 1 genes from their cellular genome. This is important because the virus will therefore not kill normal cells that do not express early gene products. Techniques for preparing replication defective adenoviruses are well known in the art as exemplified by Berkner et. al., 1983; Ghosh-Choudhury & Graham, 1987; McGrory et. al., 1988; Gluzman et. al., 1982; Rosenfeld et. al. (1991; 1992); and Stratford-Perricaudet et. al. (1990; 1992).

Other than the requirement that the adenovirus vector be replication defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the method of the present invention. This is because Adenovirus type 5 is a human adenovirus about which a great deal of biochemical and genetic information is known, and it has historically been used for most constructions employing adenovirus as a vector.

The promoter used to express the CXC chemokine, and optionally, another therapeutic gene, is not critical to the present invention. The human cytomegalovirus (CMV) immediate early gene promoter has been used (Thomsen et. al., 1984), which results in the constitutive, high-level expression of the foreign gene. However, the use of other viral or mammalian cellular promoters, which are well-known in the art, is also suitable to achieve expression of CXC chemokines, generally provided that the levels of expression are sufficient to achieve a physiological effect.

By employing a promoter with well-known properties, the level and pattern of expression of CXC chemokines following infection can be optimized. For example, selection of a promoter that is active specifically in hepatocytes will be advantageous for tissue-specific expression. Suitable promoters are the al-antitrypsin, apolipoprotein AI, liver fatty acid binding protein, LDL receptor and plasminogen activator inhibitor type 1 (PAI-1) gene promoters. Further, selection of a promoter that is regulated in response to specific physiologic signals can permit inducible expression of the ELR CXC chemokines. For example, with the ELR CXC chemokine gene being expressed from the human PAI-1 promoter, expression is inducible by tumor necrosis factor.

In that the vectors for use in the present invention are replication defective, they will typically not have an adenovirus E1 region. Thus, it will be most convenient to introduce the CXC chemokine-coding region at the position from which the E1 coding sequences have been removed. However, the position of insertion of the ELR CXC chemokine-coding region within the adenovirus sequences is not critical to the present invention. The CXC chemokine transcription unit may also be inserted in lieu of the deleted E3 region in E3 replacement vectors as described previously by Karlsson et. al. (1986).

Moreover, where a cDNA insert is employed one will typically desire to include a polyadenylation signal to effect proper polyadenylation of the CXC chemokine message. The nature of the polyadenylation signal is not believed to be crucial to the successfil practice of the invention, and any such sequence may be employed. The SV40 or protamine gene polyadenylation signal may be used as they are convenient and known to function well in the target cells employed.

In using an adenoviral, or any other viral delivery system, one will desire to purify the virion sufficiently to render it essentially free of undesirable contaminants, such as defective interfering viral particles or endotoxins and other pyrogens such that it will not cause any untoward reactions in the animal or individual receiving the treatment. Buoyant density gradients, such as cesium chloride gradient centrifugation, may be used for purification. The recombinant virus should then be dispersed in a pharmacologically acceptable solution or buffer. Preferred solutions include neutral saline solutions buffered with phosphate, lactate, Tris, and the like.

12. Pharmaceutical Compositions

CXC chemokine compositions or recombinant viruses expressing CXC chemokines will most often be formulated for parenteral administration, e.g., formulated for injection via the intravenous, intramuscular, subcutaneous, transdermal, or other such routes.

The preparation of suitable compositions that contain a CXC chemokine or CXC chemokine-expressing recombinant virus will be known to those of skill in the art in light of the present disclosure. Typically, such compositions can be prepared as injectables, either as liquid solutions or suspensions. Solid forms suitable for using to prepare solutions or suspensions upon the addition of a liquid prior to injection can also be prepared. The preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The CXC chemokine or CXC chemokine-expressing recombinant virus compositions can be formulated into a sterile aqueous composition in a neutral or salt form. Solutions as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate and gelatin.

Prior to or upon formulation, the CXC chemokine or recombinant virus component should be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Suitable pharmaceutical compositions in accordance with the invention will generally include an amount of the CXC chemokine or CXC chemokine-expressing recombinant virus admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards.

Upon formulation, an CXC chemokine or CXC chemokine-expressing recombinant virus solution will be administered in a manner compatible with the dosage formulation and in such amount as is therapeutically effective. The type of injectable solutions described above are generally preferred, but other pharmaceutically acceptable forms are also contemplated, e.g., tablets, pills, capsules or other solids for oral administration, suppositories, pessaries, nasal solutions or sprays, aerosols, inhalants, liposomal forms and the like. Pharmaceutical "slow release" capsules or compositions may also be used. Slow release formulations are generally designed to give a constant drug level over an extended period and may be used in accordance with the present invention.

13. Therapeutic Kits

This invention also provides therapeutic kits comprising CXC chemokines or CXC chemokine-expressing recombinant viruses for use in the present treatment methods. Such kits will generally contain, in suitable container means, a pharmaceutically acceptable formulation of at least one CXC chemokine or CXC chemokine-expressing recombinant virus. The kits may also contain other pharmaceutically acceptable formulations for combined therapy. For example, such kits may contain any one or more of a range of other conventional or developmental therapeutic drugs, including HGF and/or NAC.

The kits may have a single container (container means) that contains the CXC chemokine or CXC chemokine-expressing virus, with or without any additional components, or they may have distinct containers for each desired agent. Where combined therapeutics are provided, a single solution may be pre-mixed, either in a molar equivalent combination, or with one component in excess of the other. Alternatively, each of the CXC chemokine or CXC chemokine-expressing recombinant virus components and other agents, such as HGF and/or NAC, or other hepatoproliferative agents, may be maintained separately within distinct containers prior to administration to a patient.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

The containers of the kit will generally include at least one vial, test tube, flask, bottle, syringe or other container means, into which the CXC chemokine or CXC chemokine-expressing recombinant virus and any other desired agent, may be placed and, preferably, suitably aliquoted. Where separate components are included, the kit will also generally contain a second vial or other container into which these are placed, enabling the administration of separated designed doses. The kits may also comprise a second/third container means for containing a sterile, pharmaceutically acceptable buffer or other diluent.

The kits may also contain a means by which to administer the CXC chemokine or CXC chemokine-expressing recombinant virus to an animal or patient, e.g., one or more needles or syringes, or other such like apparatus, from which the formulation may be injected into the animal or otherwise applied to the body. The kits of the present invention will also typically include a means for containing the vials, or such like, and other component, in close confinement for commercial sale, such as, e.g., injection or blow-molded plastic containers into which the desired vials and other apparatus are placed and retained.

The following examples are included to demonstrate certain preferred embodiments of the invention. It will be appreciated by those of skill in the art that the compositions and techniques disclosed in the examples that follow represent compositions and techniques discovered by the inventor to function well in the practice of the invention, and thus can be considered to constitute certain preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE I

Proliferative Effects of ELR CXC Chemokines on Hepatocytes

A. Materials and Methods

1. Hepatocyte Isolation

Adult male pathogen-free Sprague Dawley rats (Charles River, Portage, Mich.) weighing 300–350 gms. were used for isolation of hepatocytes by collagenase perfusion (Berry and Friend, 1969; Alpini et al., 1994; each incorporated herein by reference). Perfusion was performed via the portal vein after anesthesia was induced with intramuscular ketamine (100 mg/kg) and maintained with inhalation of methoxyflurane. Midline laparotomy was performed and the animal heparinized (1000 units/kg) by direct administration into the inferior vena cava. The portal vein was then exposed and cannulated with a 16 gauge angiocatheter.

The liver was perfused with Hank's solution (calcium and magnesium free with 10 mM Hepes and $10^5$ U/L of penicillin/streptomycin, pH 7.4 [Biowhittaker, Walkersville, Md.]) at 37° C. at a rate of 10 ml/min to flush the liver of intravascular blood. The liver was next perfused with a collagenase solution (0.5 mg/ml collagenase B [Boehringer Mannheim, Indianapolis, Ind.] in Dulbecco's Modified Eagle's Media/F12 [DMEM/F12 {Biowhittaker, Walkersville, Md.}] with $10^5$ U/L penicillin/streptomycin) at 37° C. at a rate of 10 ml/min until there was evidence of tissue fracture beneath the liver capsule.

The liver was then gently removed from the animal, placed into a sterile petri dish containing additional collagenase solution, the liver capsule removed, and the tissue gently agitated to disperse the cells. This solution was then filtered through sterile gauze into 50 ml conical tubes and the total volume brought to 50 ml with DMEM/F12 with 10% fetal calf serum (FCS). This was then centrifuged at 360 RPM at 4° C. for 10 min, the pellet resuspended in 1% DNase solution (1% DNase [Boehringer Mannheim, Indianapolis, Ind.] in DMEM/F12); this process was then repeated two additional times. The final pellet was resuspended in plating media (Media 199, with 10% fetal calf serum, 10% horse serum, 10 mM Hepes, $10^5$ U/L penicillin/streptomycin, 1.6 U/L insulin, and $4\times10^{-7}$ M dexamethasone [Biowhittaker, Walkersville, Md.]), the cells plated on Primaria plates (Becton Dickinson Labware, Lincoln Park, N.J.), and incubated at 37° C. under 5% $CO_2$. Hepatocyte viability was generally 85–95% as determined by trypan blue exclusion. Hepatocyte purity was determined by staining for LDL, and typically demonstrated 90–95% purity.

2. Hepatocyte Stimulation

The isolated hepatocytes were allowed to adhere overnight. They were then washed with Hank's balances salt solution (HBSS) and reincubated for 24 or 72 h in serum-free DMEM/F12, with insulin, dexamethasone, and ENA-78, MIP-2, interleukin-8 (IL-8), IP-10, MIG, hepatocyte growth factor (HGF), or TNF at 100 ng/ml, 10 ng/ml, 1 ng/ml, 0.1 ng/ml, 0.01 ng/ml, 0.001 ng/ml, or in media alone. The chemokines used in these studies were obtained from R&D Systems, Minneapolis, Minn. or Pepro Tech, Inc., Rocky Hill, N.J. In studies where neutralization of ENA-78 or MIP-2 was performed, anti-ENA-78 ($1\times10^6$ titer) or anti-MIP-2 ($1\times10^6$ titer) antibodies were added to the plates concurrently with the chemokines in a volume of 200 µl/well. In the studies assessing the effects of the TVR and DLQ IL-8 mutants, the mutants were added in a concentration of 75 ng/ml. During studies attempted in the absence of insulin and dexamethasone, cell viability was severely compromised.

3. In Vitro Determination of Hepatocyte DNA Synthesis

Incorporation of $^3$H-thymidine was used to assess hepatocyte proliferation in vitro (Nakamura et al., 1983; incorporated herein by reference). Hepatocytes were distributed onto 96-well flat bottomed plates at a concentration of $1\times10^5$ cells/ml and stimulated with increasing concentrations of ENA-78, MIP-2, IL-8, HGF, MIG, or IP-10 (100 ng/ml, 10 ng/ml, 1 ng/ml, 0.1 ng/ml, 0.01 ng/ml, 0.001 ng/ml, or media alone). The chemokines used in these studies were obtained from R&D Systems, Minneapolis, Minn. or Pepro Tech, Inc., Rocky Hill, N.J. 18 h prior to harvest, 0.5 µCi of $^3$H-thymidine (6.7 Ci/mmol; Dupont-New England Nuclear, Boston, Mass.) was added to each well and the cells returned to the incubator. Cells were harvested onto glass-fiber filters with a semi-automatic harvester at 24 or 72 h of total incubation and $^3$H-thymidine incorporation into cellular DNA counted in 2 ml of scintillation solution in a standard liquid scintillation counter (Beckman, Fullerton, Calif.).

4. ELISA

Tissues or fluids were assayed for immunoreactive ENA-78 or MIP-2 by specific ELISAs using a modification of the double ligand method (Colletti et al., 1995; Colletti et al., 1996a; Strieter et al., 1992; each incorporated herein by reference). Liver tissue was processed in phosphate buffered saline (PBS) containing an anti-protease cocktail consisting of 2 mM phenyl methyl sulfonyl fluoride, and 1 µg/ml each of antipan, aprotinin, leupeptin, and pepstatin A (Sigma, St. Louis, Mo.).

Briefly, flat-bottomed 96 well microtiter plates were coated with 50 µl/well of purified polyclonal rabbit anti-ENA-78 or anti-MIP-2 (3.2 mg/ml in 0.6 M NaCl, 0.26 M $H_3BO_4$ and 0.08 N NaOH, pH 9.6) and incubated for 16 h at 4° C. and then washed with phosphate buffered saline (PBS, pH 7.5, 0.05% Tween-20 [wash-buffer]). Microtiter plate nonspecific binding sites were blocked with 2% bovine serum albumin (BSA) in PBS and incubated for 90 min at 37° C. Plates were then rinsed four times with wash buffer and diluted (neat, 1:10 and 1:100) samples consisting of cell supernatants or liver homogenates were added, followed by incubation for 1 h at 37° C. Plates were washed four times, followed by the addition of 50 µl/well of biotinylated rabbit anti-chemokine (anti-ENA-78 or anti-MIP-2) antibody (3.5 ng/ml in PBS, pH 7.5, 0.05% Tween-20, and 2% FCS) and plates incubated for 30 min at 37° C. Plates were washed four times, streptavidin-peroxidase conjugate added, and the plates incubated for 30 min at 37° C. Plates were again washed four times and chromogen substrate (0.67 mg/ml orthophenylenediamine in 25 mM citrate/phosphate pH 5.0, and 0.0002% v/v hydrogen peroxide) added.

The plates were then incubated at room temperature to the desired extinction, and the reaction terminated with 50 µl/well of 3M $H_2SO_4$ solution. Plates were read at 490 nm in an ELISA reader. Standard curves for each chemokine were run with each assay and used to calculate the concentration of antigen in the experimental samples. This ELISA method consistently detects chemokine concentrations above 10 pg/ml. The concentration of chemokine antigen in cell culture supernatants is reported in ng/ml. The ELISA values for liver tissue homogenates are standardized to the total protein content in each sample. Total protein was measured using the Pierce BCA Protein Assay Reagent (Pierce, Rockford, Ill.) according to the manufacturer's instructions.

5. TVR and DLQ Mutants

The ELR motif in wild-type IL-8 has been mutated to either TVR, which corresponds to the amino terminal sequence in IP-10, or DLQ, which corresponds to the amino terminal sequence in PF-4, by site-directed mutagenesis and expression in *Escherichia coli* (Strieter et al., 1995a; U.S. Pat. No. 5,871,723, each incorporated herein by reference).

6. Rat Model of 70% Hepatectomy

Adult male specific pathogen-free Sprague-Dawley rats (Charles River, Portage, Mich.) weighing 200–250 grams were used in all studies. All studies were performed in compliance with the standards for animal use and care set by the University of Michigan's Committee for the Use and Care of Animals. Animals were anesthetized with intramuscular ketamine hydrochloride (100 mg/kg) and inhalation of methoxyflurane. All animals received intravenous lactated Ringer's solution (40 ml/kg) to replace operative fluid and blood losses. Partial (70%) hepatectomy was performed as previously described (Higgins and Anderson, 1931). Briefly, 2–0 silk suture ligatures were secured around the base of the median and left lateral hepatic lobes and the lobes resected. Sham operated control animals were treated in an identical fashion with the omission of hepatectomy. Previous studies have demonstrated that rat liver will regenerate within 14–16 days of 70% hepatectomy (Higgins and Anderson, 1931).

7. Protocol for Tissue Procurement After 70% Hepatectomy

Following 70% hepatectomy or sham laparotomy, rats were sacrificed at 6, 12, and 24 h, and 2, 4, 6, 8, 12, and 14 days post-operatively. Each group at each time point consisted of 6 animals. At the time of sacrifice, animals were anesthetized with intramuscular ketamine hydrochloride (100 mg/kg) and inhalation of methoxyflurane. The animal was weighed, the chest and abdominal cavities opened, the animal exsanguinated, and the liver flushed of blood by infusion of 20 cc of sterile, 0.9 normal saline into the portal vein under constant low pressure. At this point, the entire liver was removed from the abdominal cavity and weighed. A 1 $cm^3$ section of liver was removed, weighed, snap frozen in liquid nitrogen, and stored for later ELISA and total protein determination.

8. Rat Neutrophil-Depletion and Liver Regeneration after Hepatectomy

In order to determine that the mitogenic effects of ENA-78 and MIP-2 were related to direct tissue effects and not due to the effects of neutrophils within the hepatic parenchyma, rats were neutrophil-depleted, subjected to 70% hepatectomy, and absolute neutrophil counts, hepatic myeloperoxidase (MPO) levels, and liver weights measured. Rats were neutrophil-depleted by intra-peritoneal administration of a rabbit anti-rat neutrophil antibody (Accurate Chemical and Scientific Corporation, Westbury, N.Y.). In the initial in vivo antibody half-life studies in rats, daily peripheral blood neutrophil counts were performed; they remained low (532±76) throughout the treatment period when the antibody was dosed appropriately for its half-life. The half-life of this antibody was determined to be 48 h.

In addition to the experimental group of neutrophil-depleted animals undergoing 70% hepatectomy, two control groups were included in these studies: 1) animals treated with control antibodies (normal neutrophil levels) and undergoing 70% hepatectomy and 2) animals subjected to sham laparotomy. Liver MPO levels were used to estimate hepatic neutrophil influx and were performed in order to confirm that peripheral blood neutrophil-depletion also decreased hepatic neutrophil influx post-hepatectomy. Previous studies have demonstrated that there is a significant hepatic neutrophil influx 12 h post-hepatectomy, which was therefore chosen as the time point to measure hepatic MPO levels (Colletti et al., 1996b; Colletti et al., 1996c; each incorporated herein by reference).

Animals were sacrificed 12 h post-hepatectomy and absolute neutrophil counts and hepatic MPO levels quantitated. Animals were also sacrificed on post-hepatectomy day 14 and absolute neutrophil counts, hepatic MPO, and hepatic weight, as a measure of hepatic regeneration, determined. Absolute neutrophil counts were performed on whole blood using standard clinical techniques by the University of Michigan Unit for Laboratory Animal Medicine.

9. Hepatic Myeloperoxidase Determination

Hepatic neutrophil infiltration was quantitated using a modification of the standard myeloperoxidase (MPO) assay (Duval, 1990; incorporated herein by reference). This modification utilizes 3-amino-1,2,4-triazole (AT; Sigma, St. Louis, Mo.) to neutralize hepatic catalase activity in order to accurately measure liver MPO activity. Previously frozen liver tissues were placed in a 50 mM potassium phosphate buffer solution (pH 6.0) with 5% hexadecyltrimethyl ammonium bromide (Sigma, St. Louis, Mo.). The tissues were homogenized, sonicated, and centrifuged at 12,000×g for 15 min at 4° C. Supernatants were then incubated with 200 mM AT with 0.1 mM $H_2O_2$ at 25° C. for 2 h in order to neutralize catalase activity. The supernatants were then assayed for MPO activity using a spectrophotometric reaction with O-dianisidine hydrochloride (Sigma, St. Louis, Mo.) at 460 nm. All values were normalized to tissue weight.

10. Treatment with Anti-ENA-78 or Anti-MIP-2 After Hepatectomy

Following 70% hepatectomy, animals were treated with anti-MIP-2 antibodies, anti-ENA-78 antibodies, or control antibodies, given by intraperitoneal injection, every 48 h for 14 days. Previous studies have demonstrated the half-life of these antibodies to be approximately 48 h. These antibodies were high titer, purified polyclonal rabbit anti-murine MIP-2 ($1\times10^5$ titer) or rabbit anti-human ENA-78 ($1\times10^6$ titer). Control antibodies consisted of polyclonal rabbit serum without ENA-78 or MIP-2 blocking properties. A dose of 1 cc per animal was used. At 14 days, the animals were weighed, sacrificed, and the livers removed and weighed. Rabbit anti-ENA-78 or anti-MIP-2 antibodies were generated as previously described (Strieter et al., 1992; U.S. Pat. No. 5,871,723, each incorporated herein by reference).

11. Statistical Analysis

The in vivo studies utilized 6 rats in each group at each time point, except for the antibody neutralization studies. In this case, 3 rats were used per group due to the necessity to use a large quantity of antibody for these studies. For the in vitro studies, all studies were performed in triplicate and each study was repeated a minimum of 3 times, except for the studies involving the TVR and DLQ IL-8 mutants. For these studies, each study was run in duplicate and the studies were performed twice. Groups of data were evaluated by analysis of variance by the methods of Student-Newman-Keul to indicate groups with significant differences (Glantz, 1987). Data that appear statistically significant were compared by Student's t-test for comparing the means of multiple groups, and were considered significant if p values were less than 0.05. Results are presented as means±SEM. Data was analyzed by Macintosh Centris 650 computer using the Statview II statistical software package (Abacus Concepts, Inc.).

B. Results

1. Hepatocyte Proliferation In Vitro in Response to MIP-2 and ENA-78

In initial studies, primary rat hepatocytes in vitro were stimulated with increasing concentrations of the ELR containing chemokines, MIP-2, ENA-78, and IL-8 or increasing concentrations of the non-ELR containing chemokines, IP-10 or MIG. HGF was used as a positive control. Media alone was used as a negative control. Hepatocyte proliferation, as measured by incorporation of $^3$H-thymidine, was performed at 24 and 72 h of incubation.

As demonstrated in FIG. 1, there is a significant increase in hepatocyte proliferation at 24 h of incubation in response to MIP-2, ENA-78, and IL-8, and this level of proliferation is at least as significant as that seen in response to HGF. There is no proliferative effect seen in response to IP-10 or MIG, the non-ELR-containing chemokines, when used alone in this isolated system. The positive effects of ELR CXC chemokines were also seen at 72 h of incubation, however, at this more delayed time point, the effects of HGF were more significant than those of the ELR containing CXC chemokines.

Cell counts were performed in parallel with the initial studies using $^3$H-thymidine in order to confirm that the CXC chemokines were acting on hepatocytes and not on other cell types, such as Kupffer cells, Ito cells, or endothelial cells. As described earlier, the primary hepatocyte preparations were 90–95% pure. These studies confirmed that hepatocytes were proliferating, as opposed to other cell types.

2. TNF as a Proximal Trigger for MIP-2 and ENA-78 In Vitro

Figure 2:
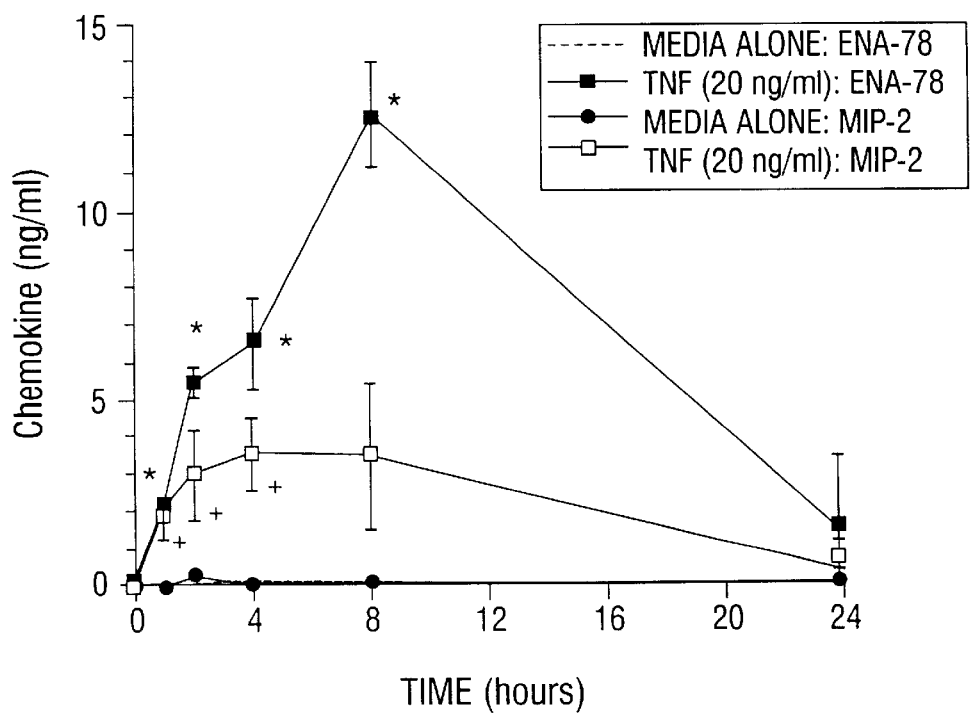
FIG. 2. Primary rat hepatocyte production of ENA-78 and MIP-2 in vitro following stimulation with 20 ng/ml TNF. Primary rat hepatocytes were stimulated with 20 ng/ml TNF or were incubated in media alone. Using an ELISA, cell supernatants were assayed for the presence of MIP-2 and ENA-78 at 0, 1, 2, 4, 8, and 24 h of incubation. Significant amounts of both ENA-78 and MIP-2 were detected within 1 h of TNF stimulation, with maximal levels being detected 4 to 8 h following TNF stimulation. *$p<0.01$ vs. media alone; +$p<0.05$ vs. media alone.

TNF is an important proximal trigger for the production of MIP-2 and ENA-78. It was next investigated whether TNF is also an important proximal trigger for the production of ENA-78 and MIP-2 by primary rat hepatocytes in vitro. As FIG. 2 demonstrates, hepatocytes produce significant amounts of ENA-78 and MIP-2 in response to stimulation with TNF.

3. Mitogenic Effects of TNF In Vitro

TNF is also known to be mitogenic for hepatocytes. Since the present studies demonstrate that TNF can induce hepatocyte production of ENA-78 and MIP-2 and that these molecules are mitogenic for primary rat hepatocytes in vitro, the inventors reasoned that some or all of the mitogenic effects of TNF in the liver may be due to upregulation of ENA-78 and MIP-2. In order to test this hypothesis, primary rat hepatocytes in vitro were stimulated with increasing concentrations of TNF, from 0.001 ng/ml to 100 ng/ml, with concurrent incubation with neutralizing antibodies to ENA-78 or MIP-2.

Figure 3:
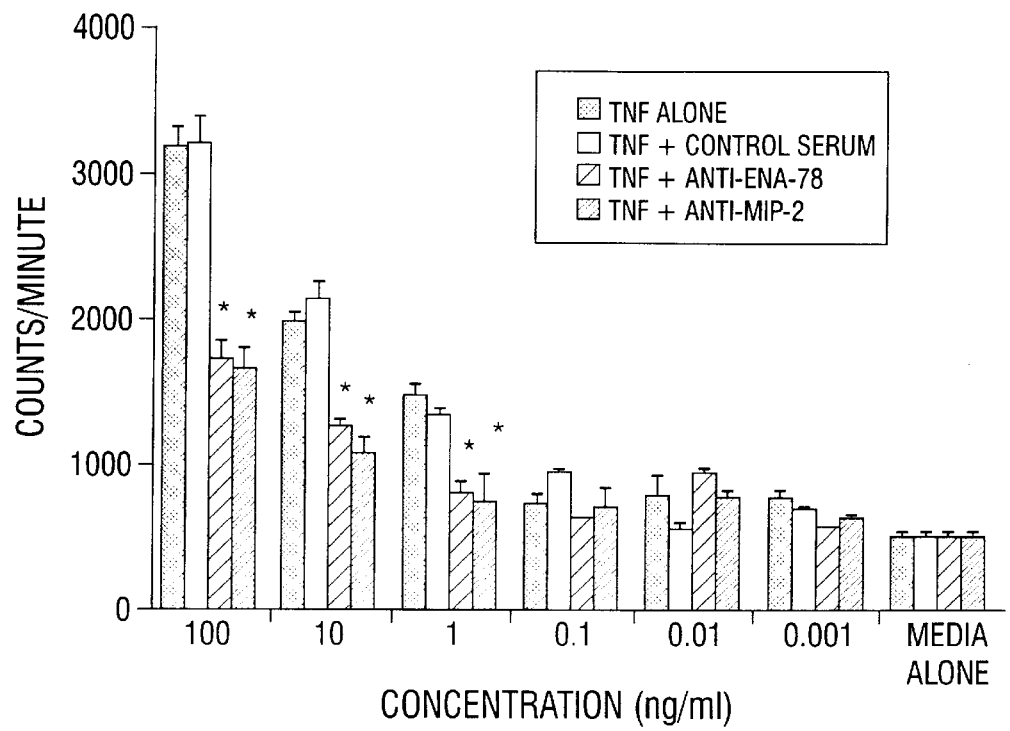
FIG. 3. Primary rat hepatocyte proliferation in vitro in response to TNF alone, TNF plus control serum, TNF plus anti-ENA-78 antiserum, or TNF plus anti-MIP-2 antiserum, as measured by incorporation of $^3$H-thymidine. Primary rat hepatocytes in vitro were stimulated with increasing concentrations of TNF from 0.001 ng/ml to 100 ng/ml, either alone, or in combination with anti-ENA-78 antiserum, anti-MIP-2 antiserum, or control serum without blocking properties against ENA-78 or MIP-2. Media alone was used as a negative control. Proliferation was measured by incorporation of $^3$H-thymidine at 72 h of incubation. A significant proliferative response to TNF alone or TNF plus control serum is seen at 72 h of incubation. The addition of anti-ENA-78 antiserum or anti-MIP-2 antiserum to cells stimulated with TNF, significantly, although incompletely, blocks the proliferative actions of TNF, suggesting that some of the proliferative response to TNF may be related to TNF-induced upregulation of MIP-2 and ENA-78. *$p<0.005$ vs. TNF alone or TNF plus control serum, +$p<0.05$ vs. TNF alone or TNF plus control serum.

These studies demonstrated some proliferative responses at 24 h of incubation. At 72 h of incubation, hepatocyte proliferation was evident and this was significantly inhibited by concurrent incubation with anti-ENA-78 antibodies or anti-MIP-2 antibodies, although the inhibition was not complete (FIG. 3). This suggests that the mitogenic effects of TNF may, in part, be related to up-regulation of hepatocyte MIP-2 and/or ENA-78.

4. Interplay of ELR-negative and ELR-positive CXC Chemokines

Figure 4A:
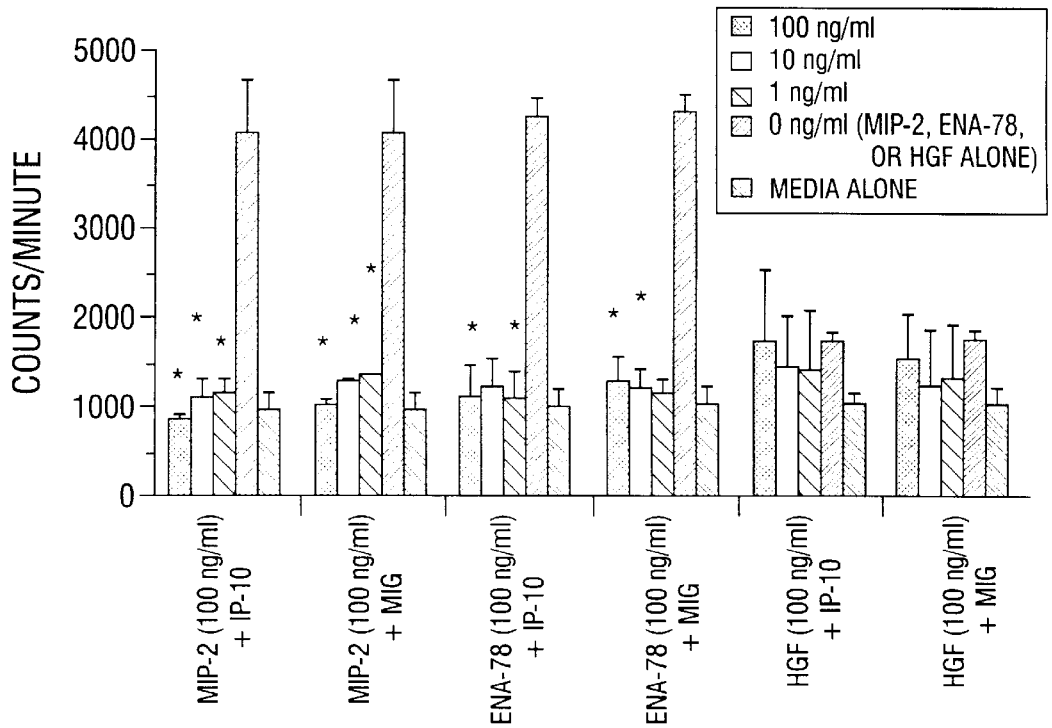
FIG. 4A and FIG. 4B. Primary rat hepatocyte proliferation in vitro in response to MIP-2, ENA-78, or HGF in combination with the ELR negative CXC chemokines, IP-10 or MIG, as measured by incorporation of $^3$H-thymidine. Primary rat hepatocytes were stimulated with 100 ng/ml of MIP-2, ENA-78, or HGF. These cells were then additionally stimulated with increasing concentrations of IP-10 or MIG, from 100 ng/ml to 0 ng/ml, and proliferation measured by the incorporation of $^3$H-thymidine at 24 (FIG. 4A) and 72 h of incubation (FIG. 4B). Media alone was used as a negative control. Stimulation with 0 ng/ml of IP-10 or MIG was used as a positive control. A significant inhibition of MIP-2- and ENA-78-induced hepatocyte proliferation is demonstrated at 24 and 72 h of incubation, with the addition of IP-10 or MIG. The combination of IP-10 or MIG with HGF also appears to decrease HGF-induced hepatocyte proliferation, however, this did not reach statistical significance. *p<0.05 vs. MIP-2 or ENA-78 alone.
Figure 4B:
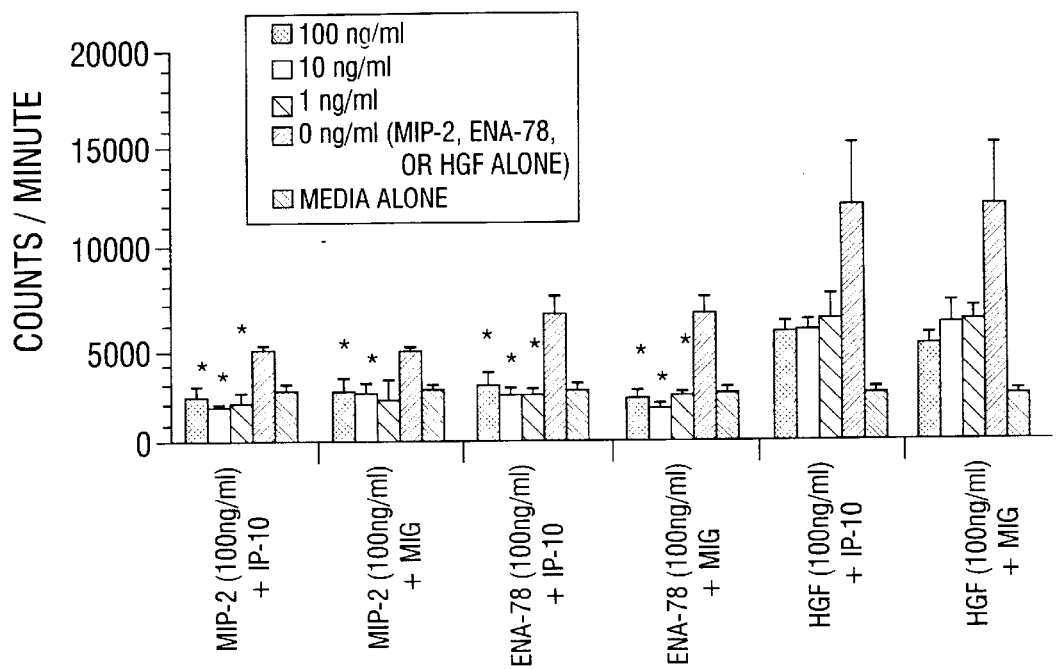

The ELR motif is important for the many of the biological effects of the CXC chemokines, specifically both the neutrophil chemotactic effects and the angiogenic effects of these molecules are dependent on the presence of this particular sequence of amino acids. In order to assess whether this motif was also important for the mitogenic effects on hepatocytes in vitro, cells were incubated with MIP-2, ENA-78, or HGF at 100 ng/ml and increasing concentrations of MIG or IP-10 (1 ng/ml, 10 ng/ml, or 100 ng/ml), and the effects on hepatocyte proliferation assessed at 24 and 72 h of incubation. These studies demonstrated that the ELR-negative CXC chemokines inhibited the mitogenic effects of the ELR-positive CXC chemokines (FIG. 4A and FIG. 4B).

In order to more specifically evaluate the role of the ELR motif in the mitogenic effects of the ELR-containing CXC chemokines, two specific ELR mutants were investigated. The ELR motif in wild-type IL-8 was mutated to either TVR, which corresponds to the amino terminal sequence in IP-10, or DLQ, which corresponds to the amino terminal sequence in platelet factor-4 (PF-4), by site-directed mutagenesis and expression in $E$ $coli$ (Strieter et al., 1995a; U.S. Pat. No. 5,871,723, each incorporated herein by reference).

Figure 5A:
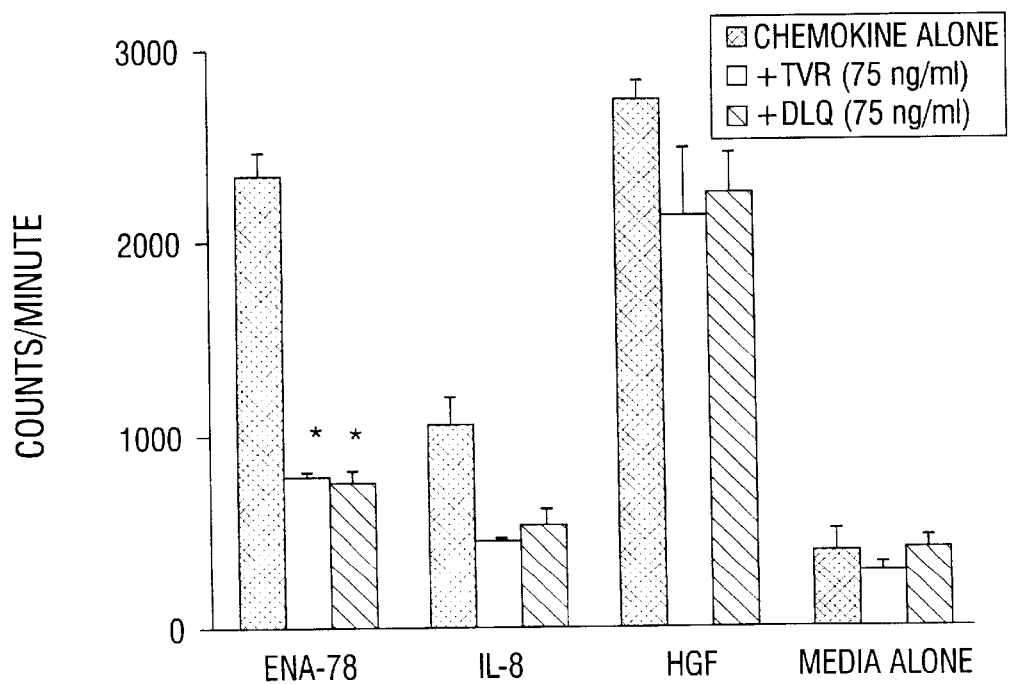
FIG. 5A and FIG. 5B. Primary rat hepatocyte proliferation in vitro in response to ENA-78, IL-8, or HGF alone or in combination with the TVR or DLQ mutant of IL-8. Primary rat hepatocytes were stimulated with 100 ng/ml of ENA-78, IL-8, or HGF, alone or in combination with 75 ng/ml of the TVR or DLQ mutant of IL-8. Media alone was used as a negative control. Hepatocyte proliferation was measured at 24 (FIG. 5A) and 72 h (FIG. 5B) of incubation by the incorporation of $^3$H-thymidine. The addition of either the TVR or DLQ mutant resulted in a significant inhibition of ENA-78-induced hepatocyte proliferation at both 24 and 72 h of incubation. This inhibition was only seen at 72 h of incubation for IL-8. A similar inhibition is not seen for HGF. *p<0.01 vs. ENA-78 or IL-8 alone.
Figure 5B:
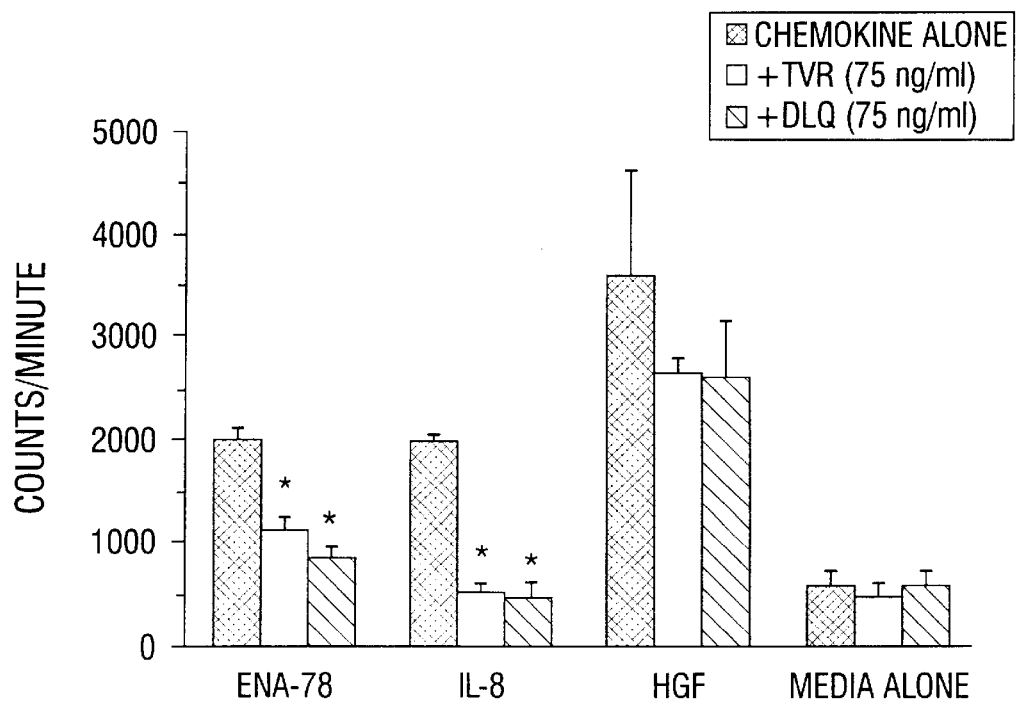

In these studies, hepatocytes were incubated with 75 ng/ml of the TVR or DLQ mutants in addition to 100 ng/ml or ENA-78, MIP-2, or HGF. As FIG. 5A and FIG. 5B demonstrate, both the TVR and DLQ mutants significantly inhibited hepatocyte proliferation in response to ENA-78 or MIP-2. A similar response was not seen with HGF.

5. Role of MIP-2 and ENA-78 Following 70% Hepatectomy In Vivo

Figure 6A:
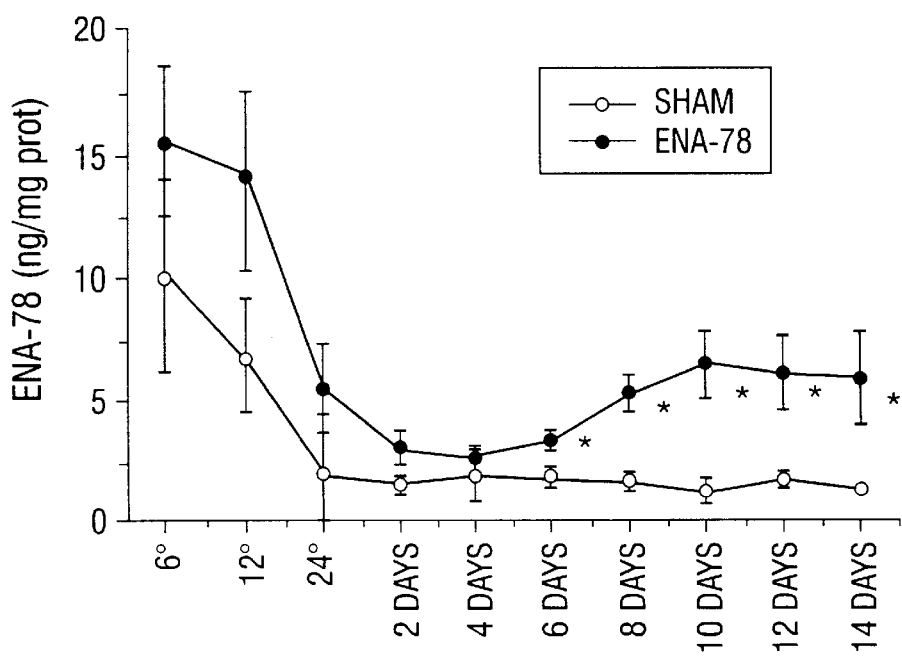
FIG. 6A and FIG. 6B. Hepatic tissue levels of ENA-78 and MIP-2 following 70% hepatectomy in the rat. Rats were subjected to 70% hepatectomy or sham laparotomy and sacrificed at 6, 12, and 24 h and 2, 4, 6, 8, 10, 12, and 14 days post-operatively. Rat hepatic tissue levels of ENA-78 (FIG. 6A) and MIP-2 (FIG. 6B) were then measured at each of these time points using an ELISA. Chemokine levels were normalized to tissue protein levels. Both ENA-78 and MIP-2 levels were significantly increased during hepatic regeneration following partial hepatectomy, as compared to sham operated control animals. For FIG. 6A, *p<0.05 vs. sham. For FIG. 6B, p<0.05 vs. sham at all time points.
Figure 6B:
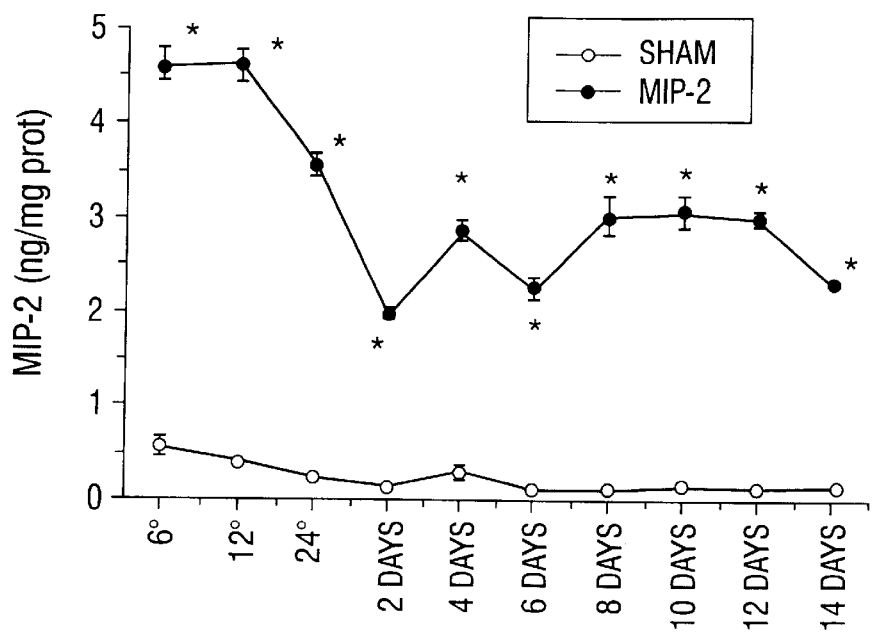

As the in vitro studies showed that ENA-78 and MIP-2 are mitogenic for hepatocytes, the role of these molecules in in vivo hepatic injury, repair and regeneration was next investigated. Hepatic levels of MIP-2 and ENA-78 were increased following 70% hepatectomy in rats (FIG. 6A and FIG. 6B). MIP-2 appeared to be more consistently elevated throughout the regenerative period (FIG. 6B).

In order to further investigate the role of these two molecules in hepatic regeneration and repair following 70% hepatectomy, rats were treated with anti-ENA-78 or anti-MIP-2 antibodies throughout the regenerative period. These studies also showed that neutralization of ENA-78 decreased the rate of hepatic regrowth following 70% hepatectomy. The absolute liver weights as well as the relative liver weights are significantly decreased in animals treated with anti-ENA-78 antibodies (Table 1). The results following treatment with anti-MIP-2 antibodies are less conclusive. While the relative liver weights in the anti-MIP-2 treated animals are significantly less than those in the control animals, a similar effect is not seen for the absolute liver weights (Table 1).

There are many potential reasons for the results observed with anti-MIP-2. First, this is a complex, in vivo system in which many hepatic mitogens are likely involved in the hepatic reparative process. Neutralization of one or more of these mitogens in vivo may therefore not have a readily measurable effect on the overall regenerative process. In addition, the ENA-78 antibodies that were available for these studies had a higher titer than those of the anti-MIP-2 antibodies. Since the in vitro studies suggest that MIP-2 may be the more potent mitogen, this may also account for the disparate results.

Since both MIP-2 and ENA-78 have significant neutrophil chemotactic effects, it was investigated whether the mitogenic effects of these molecules in vivo were related to the presence of neutrophils within the hepatic parenchyma. Rats were neutrophil-depleted prior to 70% hepatectomy and neutrophil depletion was maintained throughout the regenerative period. Two time points were investigated in these studies. In order to ensure that peripheral neutrophil depletion would also decrease hepatic neutrophil depletion, hepatic neutrophil influx was assessed at 12 h following hepatectomy, at which point it was confirmed that peripheral neutrophil depletion did result in hepatic neutrophil depletion. Neutrophil depletion was also maintained out to 14 days following hepatectomy, and at this time point, liver regeneration was assessed as measured by hepatic weight. These studies demonstrated that neutrophil depletion has no effects on hepatic regeneration and repair following 70% hepatectomy, suggesting that the effects of MIP-2 and ENA-78 are not due to their neutrophil chemotactic properties (Table 2).

TABLE 1

Liver weight 14 days following 70% hepatectomy in rats receiving anti-ENA-78; anti-MIP-2 or control antibody.

|  | TOTAL BODY WT (GRAMS) | LIVER WT (GRAMS) | LIVER WT AS % OF BODY WT |
|---|---|---|---|
| Group I |  |  |  |
| Control Antibody | 322.0 ± 4.0 | 11.1 ± 0.26 | 3.35 ± 0.03 |
| Anti-ENA-78 Antibody | 331.6 ± 5.5 | 9.5 ± 0.14† | 2.95 ± 0.06† |
| Group II |  |  |  |
| Control Antibody | 288.0 ± 5.5 | 11.74 ± 0.58 | 4.07 ± 0.15 |
| Anti-MIP-2 Antibody | 321.7 ± 9.0* | 10.99 ± 0.27 | 3.42 ± 0.87* |

*Liver weight and total body weight are wet weights
†p < 0.05 vs. control antibody

TABLE 2

Effects of neutrophil-depletion on
liver regeneration following 70% hepatectomy

| Group | PMN's-12 hrs | Hepatic MPO-12 hrs | PMN-14 days | Hepatic MPO-14 days | Liver weight-14 day |
|---|---|---|---|---|---|
| Anti-PMN | 312 ± 32* | 126 ± 26 | 896 ± 75* | 76 ± 11 | 13.3 ± 0.65 gm |
| Control Ab | 5398 ± 143 | 413 ± 48** | 4635 ± 937 | 68 ± 15 | 12.2 ± 0.37 gm |
| Sham | 6209 ± 273 | 102 ± 14 | 6145 ± 858 | 73 ± 10 | 14.6 ± 0.61 gm |

*$p < 0.005$ vs. Sham and Control Ab
**$p < 0.001$ vs. Anti-PMN and Sham
Anti-PMN = neutrophil depletion + 70% hepatectomy; Control Ab = control antibody (normal neutrophil counts) + 70% hepatectomy; Sham = sham laparotomy without neutrophil depletion; PMN's = absolute neutrophil count; MPO = myeloperoxidase in mOD/min/gm tissue

EXAMPLE II

Liver Regenerative Qualities of ELR CXC Chemokines

A. Materials and Methods

1. Acetaminophen-induced Hepatic Injury

Female CD1 mice (6–8 wk of age) were purchased from Charles River Laboratories (Portage, Mich.) and maintained under specific pathogen-free conditions with free access to water and food prior to each study. Fresh suspensions of acetaminophen (Sigma Chemical Company, St. Louis, Mo.) were made daily by dissolving the compound in phosphate buffered saline (PBS) warmed to 40° C. In all studies, mice were allowed free access to water alone prior to an i.p. injection of 400 mg/kg acetaminophen (Manatou et al., 1996; incorporated herein by reference).

Protocol 1: In the first set of studies, groups of fasted CD1 mice were retreated with pre-immune rabbit serum or polyclonal rabbit anti-mouse antibody directed against the ELR-CXC chemokine receptor CXCR2, and these mice were sacrificed at 6, 48 and 144 h after acetaminophen challenge for histological examination of liver tissue. All polyclonal rabbit antibodies were generated and screened to ensure specificity prior to use (Evanoff et al., 1992; incorporated herein by reference). The biological half-life of these immunoneutralizing antibodies was approximately 36 h (Colletti et al., 1996). The anti-CXCR2 antibody inhibited KC-induced neutrophil influx into the peritoneum of mice, and the MIP-2- and KC-induced angiogenesis in the rat cornea.

Additional groups of mice (n=5–8 mice/group) were pretreated with 0.5 ml of pre-immune rabbit serum or the same volume of polyclonal rabbit anti-mouse MIP-2 antibody 2 h prior to acetaminophen challenge. Mice were sacrificed at 144 h after acetaminophen challenge and livers were prepared for histological examination.

Protocol 2: In the second set of studies, mice were fasted for 12 h and received one of NAC, murine MIP-2, the human proteins ENA-78, IL-8, HGF or IP-10 either immediately or 10 h after acetaminophen challenge. Recombinant chemokines and HGF were obtained from R&D Systems (Minneapolis, Minn.) or Pepro Tech (Rockyhill, N.J.) and NAC was obtained from Sigma Chemical Co (St. Louis, Mo.). Mice were injected i.v. with 100 μg of NAC or 2 μg of recombinant protein (ENA-78, IL-8, HGF or IP-10) dissolved in 0.5 ml of normal saline. All mice were subsequently sacrificed 48 h after acetaminophen challenge and serum and liver samples were removed.

Protocol 3: In the next set of studies, mice were fasted for 24 h and received MIP-2 (2 μg) or NAC (100 μg) via an i.v. injection either immediately or 10 h after acetaminophen challenge, and liver and serum samples were removed from surviving mice 48 h after acetaminophen challenge. Liver and serum samples from the experimental groups and from mice challenged with an i.p. injection of PBS and treated i.v. with normal saline were processed as described below.

2. Chemokine ELISAs

Immunoreactive levels of CC and CXC chemokines were measured in liver homogenates using a modified double-ligand ELISA procedure (Evanoff et al., 1992; incorporated herein by reference). Prior to each ELISA, snap frozen liver samples were thawed on ice, weighed and homogenized in solution containing 2 mg of protease inhibitor (Complete™; Boehringer Mannheim, Indianapolis, Ind.) per ml of normal saline. Complete™ does not interfere with any of the chemokine ELISAs (Evanoff et al., 1992).

Cell-free supernatants from the liver homogenates were loaded in duplicate into 96-well microtiter plates coated with the appropriate capture antibody, and blocked with 2% bovine serum albumin in PBS. Each ELISA consistently detected concentrations of chemokines below 10 pg/ml, and the specificity of the polyclonal detection and capture antibodies was confirmed prior to its use in an ELISA. Chemokines levels in liver homogenates were normalized to the weight of the liver sample assayed.

3. Serum Aspartate Aminotransferase

Acute hepatocellular injury results in elevated levels of aspartate aminotransferase (AST). Serum levels of AST were determined 48 h after mice were challenged with acetaminophen by Clinical Pathology at the University of Michigan Medical School (Ann Arbor, Mich.) using standardized techniques.

4. Histology

For histological assessment of hepatic injury, liver tissues were fixed in 4% paraformaldehyde for 24 h prior to routine histological processing. A pathologist assessed hematoxylin and eosin stained slides from acetaminophen-challenged mice in a blinded manner. Separate scoring systems were devised to indicate the area of liver necrosis and hemorrhage, and the extent of hepatic inflammation. Detailed histological grading of hepatic injury including area of liver necrosis and hemorrhage was determined at 48 h after acetaminophen challenge. Hepatic inflammation was graded as absent, slight, moderate, or prominent.

5. Cultured Hepatocyte Proliferation

The effects of chemokines, NAC and HGF on hepatocyte proliferation after a 24 h acetaminophen challenge were examined using normal murine liver cells obtained from American Type Culture Collection (ATCC CRL-1638; NmuLi). Hepatocytes were plated at a density of $1.0 \times 10^5$ cells/well in 6-well tissue culture plates, and were deprived of fetal bovine serum supplementation for 36 h prior to an study. Fasted hepatocytes were subsequently exposed to 2.5 mg/ml of acetaminophen and were left untreated or treated with one of NAC, MIP-2, ENA-78, IL-8, IP-10 or HGF. NAC at 1 mM or individual cytokines at 1 ng/ml were added either immediately or 10 h after the addition of acetaminophen.

In additional in vitro studies, normal serum or anti-CXCR2 antibody was also included in cultures of treated or untreated hepatocytes exposed to PBS or acetaminophen. Ten $\mu$Ci of [$^3$H]thymidine was added to each well for the final 4 h of culture, and 24 h after the addition of acetaminophen suspensions of hepatocytes were prepared via cell lysis with 0.5% (v/v) Triton-X100. [$^3$H]thymidine incorporation was assessed by liquid scintillation counting on a Beckman counter (Beckman Instruments, Fullerton, Calif.).

6. Statistical Analysis

Results are expressed as means±standard error of the mean (SE) of 5–10 mice per group, and analysis of variance was used to detect significant differences between means. All statistical calculations were performed using GraphPad Prism 2.0 computer software (San Diego, Calif.), and a $P \leq 0.05$ was considered significant.

B. Results

1. MIP-2 is Elevated in Liver Injury

Endogenous hepatic levels of murine monocyte chemoattractant protein-1 (MCP-1), macrophage inflammatory protein-1$\alpha$ (MIP-1$\alpha$), MIP-2 and KC were determined by ELISA (Table 3). KC is a murine ELR-CXC chemokine with neutrophil chemotactic properties (Lentsch et al., 1998) that binds CXCR2 with approximately 10-fold less affinity than MIP-2 (Lee et al., 1995).

The murine CC chemokines MCP-1 and MIP-1$\alpha$ were unchanged in liver homogenates from mice challenged 48 h previously with 400 mg/kg of acetaminophen. In contrast, significant elevations in the murine ELR-CXC chemokines MIP-2 and KC were present in the same liver homogenates.

TABLE 3

Changes in hepatic levels of chemokines prior to and 48 h after acetaminophen challenge in mice

| CHEMOKINE | Prior to Acetaminophen[a] (ng/g tissue) | 48 h post Acetaminophen[b] (ng/g tissue) |
|---|---|---|
| MCP-1 | 1.0 ± 0.1 | 0.9 ± 0.3 |
| MIP-1$\alpha$ | 0.5 ± 0.1 | 0.1 ± 0.2 |
| MIP-2 | 0.4 ± 0.1 | 0.8 ± 0.1[‡] |
| KC | 0.4 ± 0.1 | 0.9 ± 0.2* |

[a]Mice were fasted for 12 h prior to liver removal. Tissue samples were homogenized and supernatants were analyzed using ELISA. Data are mean ± SE of four representative studies.
[b]Mice were fasted for 12 h prior to receiving an intraperitoneal injection of 400 mg/kg acetaminophen. Forty-eight h later, liver was removed and prepared for ELISA. Data are mean ± SE of four representative studies.
‡P = 0.047 compared to levels in liver removed prior to acetaminophen
*P = 0.033 compared to levels in liver removed prior to acetaminophen.

2. Anti-MIP-2 Antibodies Block Hepatic Regeneration

The role of increased MIP-2 levels in regenerating liver was further explored through the use of a polyclonal rabbit antibody directed against murine MIP-2, or pre-immune rabbit (control) serum, given to mice 2 h prior to acetaminophen challenge.

The histological appearances of the livers from mice pretreated with either anti-MIP-2 antibodies or control serum prior to acetaminophen challenge were analyzed. Mice were fasted for 12 h and received neutralizing or control antibodies 2 h prior to i.p. injection with 400 mg/kg of acetaminophen. Mice were allowed free access to food following these treatments and 6 days later the liver was removed from each mouse for routine histological processing.

Histological injury was absent in liver tissue removed from mice that received pre-immune rabbit serum. Mice that received anti-MIP-2 antibody exhibited centrilobular hepatic injury and inflammation, and major areas of necrosis and hemorrhage were also apparent. in the liver. In mice that did not receive acetaminophen, the presence of anti-MIP-2 antiserum or normal rabbit serum did not exert any discernable injurious effect on the liver, indicating that these treatments are not toxic per se.

These results show that endogenous MIP-2 is critical for normal liver regeneration in the mouse following acetaminophen challenge. In contrast to mice that received pre-immune serum, severe disruption of the hepatic architecture around central veins was readily apparent in mice that received anti-MIP-2 prior to acetaminophen challenge 6 days previously. Areas of necrosis encompassing>50% of the total liver area were apparent in mice pretreated with anti-MIP-2 antibody.

3. Anti-CXCR2 Antibodies Block Hepatic Regeneration

The role of endogenous CXCR2 in the hepatotoxic effects of acetaminophen was examined in fasted mice that received either neutralizing rabbit anti-mouse CXCR2 antibody or pre-immune rabbit (control) serum 2 h prior to acetaminophen challenge. CXCR2 is the only CXC chemokine receptor that binds ELR-CXC chemokines in the mouse (Cacalano et al., 1994; Lee et al., 1995).

The histological appearances of the livers from mice pretreated with either anti-CXCR2 or pre-immune serum prior to acetaminophen challenge were analyzed. Mice were fasted for 12 h, and received anti-CXCR2 or pre-immune serum 2 h prior to an i.p. challenge with 400 mg/kg of acetaminophen. Liver tissue was removed at 6 h and 48 h after acetaminophen challenge.

At both time points, profoundly greater hemorrhage and necrotic injury in the liver was observed in anti-CXCR2 antibody treated mice compared to that in mice that received pre-immune serum prior to acetaminophen challenge. Anti-CXCR2 antibody pretreatment thus markedly enhanced the degree of liver hemorrhage and necrosis after acetaminophen challenge. Again, mice that received anti-CXCR2 or control antisera alone did not show liver injury at any time point, indicating that the antibodies are not themselves toxic.

Certain mice were also pretreated with anti-CXCR2 antibody, exposed to acetaminophen challenge and allowed 6 days for potential recovery. In liver samples removed from these mice, significant liver necrosis was still apparent. This was in marked contrast to the restored liver histology at the same time in mice that received pre-immune serum prior to acetaminophen challenge. This shows that, at the acetaminophen dose chosen, the normal repair mechanisms can operate within 6 days, but that interfering with chemokine binding to the CXCR2 receptor prevents this process.

4. ELR-CXC Chemokines Function Outside the NAC Therapeutic Window

The therapeutic effects of ELR-CXC chemokines were compared to those of NAC and HGF therapy during acetaminophen hepatotoxicity. In untreated CD1 mice, the mean serum AST level was increased approximately 20-fold above the baseline value of 99±34 IU/L at 48 h after acetaminophen challenge (FIG. 7A and FIG. 7B).

Figure 7A:
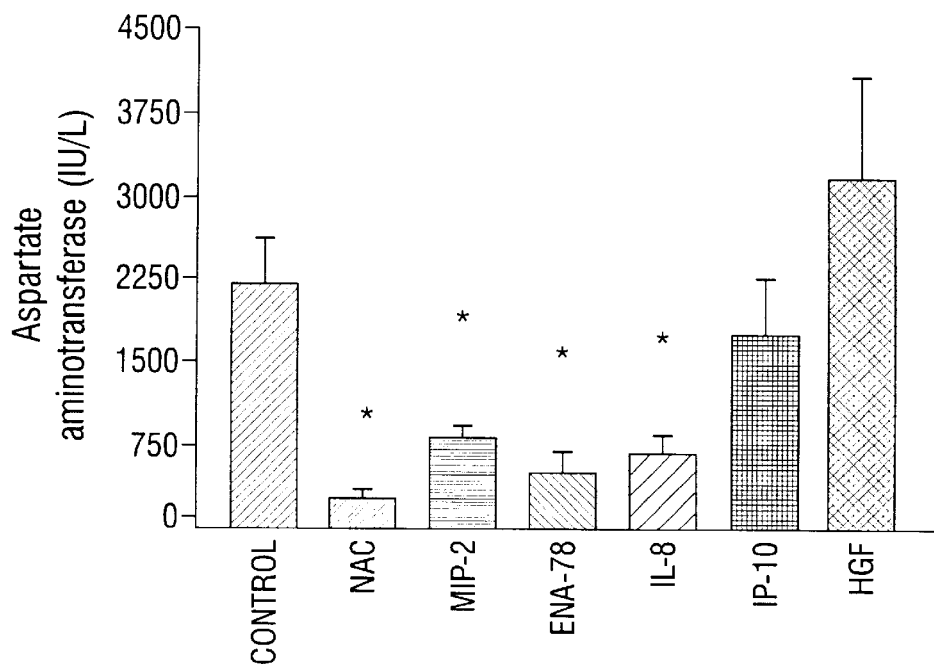
FIG. 7A and FIG. 7B. Serum aspartate aminotransferase (AST) activity in mice treated immediately after (FIG. 7A) or 10 h post (FIG. 7B) acetaminophen challenge. Mice were fasted for 12 h prior to i.p. injection with 400 mg/kg of acetaminophen, and then allowed free access to food. Forty-eight h later, blood was removed from each mouse for AST determination. When administered immediately following acetaminophen challenge, NAC was most effective at reducing AST levels compared to the other treatments. In addition, AST levels were significantly reduced in mice that received MIP-2, ENA-78, or IL-8, but not IP-10 or HGF (FIG. 7A). In contrast, when therapeutic intervention was delayed 10 h after acetaminophen challenge, only MIP-2, ENA-78 and IL-8 significantly reduced serum AST levels (FIG. 7B). Data are means±SE of four separate studies (n=5 mice/group) and * indicates that P≦0.05 compared to control.

Among the treatments used immediately after acetaminophen challenge, NAC treatment reduced AST levels by approximately 90% (FIG. 7A). In addition, all three ELR-CXC chemokines, MIP-2, ENA-78 and IL-8 (one mouse and two human), significantly reduced serum AST levels by approximately 50%.

Figure 7B:
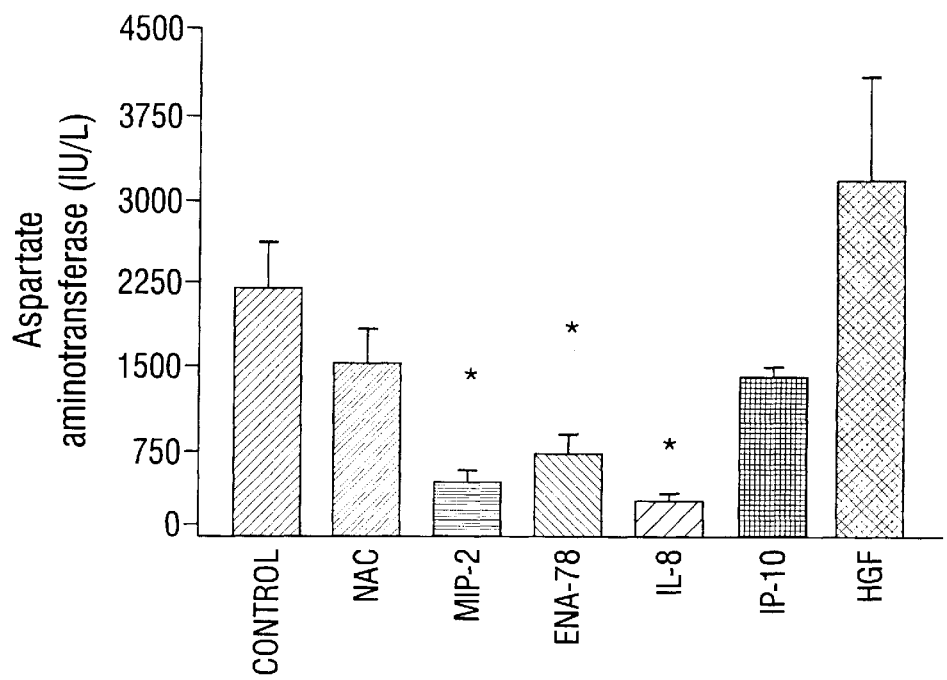

Importantly, when treatment was delayed 10 h after acetaminophen challenge, MIP-2, ENA-78 and IL-8 were still able to significantly reduced serum AST levels (FIG. 7B). This is in marked contrast to NAC, which was no longer able to significantly reduced serum AST levels (FIG. 7B).

The histological appearances of the livers from normal mice and mice that were challenged with acetaminophen and received saline or 2 μg of murine MIP-2, human ENA-78, human IL-8, human IP-10, human HGF or 100 μg of NAC were also analyzed. Mice were fasted for 12 h prior to i.p. injection with 400 mg/kg of acetaminophen, and then allowed free access to food. In these studies, saline, chemokines or NAC were given by i.v. injection 10 h after acetaminophen challenge, and liver was removed from each mouse for histological examination at the 48 h time point after acetaminophen.

The hepatic injury observed at 10 h and 48 h after acetaminophen challenge was characterized by intense necrosis and hemorrhage localized around central veins in the liver. In untreated mice, greater than 50% of the total liver mass was necrotic and exhibited hemorrhage.

In these 10 h delayed treatments, marked attenuation of liver injury was observed only in mice that received 2 μg of MIP-2, ENA-78 or IL-8. Neither HGF nor 100 μg of NAC were effective 10 h after acetaminophen challenge. MIP-2, ENA-78 and IL-8 produced major histological improvements, particularly in the centrilobular regions most sensitive to the hepatotoxic effects of acetaminophen. The beneficial effects of delayed MIP-2, ENA-78 and IL-8 therapy were therefore marked around hepatic central veins, where healthy hepatocytes were readily apparent. The histological appearance of liver sections in these treatment groups was even similar to that observed in normal mice. In addition, necrotic injury in acetaminophen-challenged mice treated with ELR-CXC chemokines was either absent or comprised less than 10% of the liver area.

5. ELR-CXC Chemokines Protect From Lethal Effects of Acetaminophen

The lethal effects of a 400 mg/kg dose of acetaminophen were evident when mice were fasted for a longer duration. In these studies, only 25% of mice fasted for 24 h prior to acetaminophen challenge survived until day 2 (Table 4). NAC treatment of mice immediately after acetaminophen challenge increased mouse survival to 90%, whereas MIP-2 given at the same time spared approximately 50% of mice. When NAC treatment was delayed by 10 h after acetaminophen challenge, the survival rate in this group of mice was significantly reduced to 25%. In contrast, 60% of mice that received a similarly delayed treatment of MIP-2 were protected from the lethal effects of acetaminophen (Table 4).

TABLE 4

Percent survival in CD1 mice fasted for 24 h and challenged with 400 mg/kg of acetaminophen

| TREATMENT | Immediately After Acetaminophen[a] | 10 h post Acetaminophen[b] |
|---|---|---|
| Saline | 25 | 25 |
| NAC | 90* | 20 |
| MIP-2 | 50* | 60* |

[a]Groups of n = 12 (saline), 13 (NAC) and 15 (MIP-2) mice were fasted for 24 h, challenged i.p. with 400 mg/kg acetaminophen, and immediately thereafter received 0.5 ml of saline, NAC or MIP-2 through i.v. injection. Survival was monitored over the subsequent 48 h.
[b]Groups of n = 12 (saline), 13 (NAC) and 10 (MIP-2) mice were fasted for 24 h, challenged i.p. with 400 mg/kg acetaminophen, and 10 h thereafter received 0.5 ml of saline, NAC or MIP-2 through i.v. injection. Forty-eight h later, liver was removed and prepared for ELISA.
*$P \leq 0.05$ compared with saline control.

Figure 8:
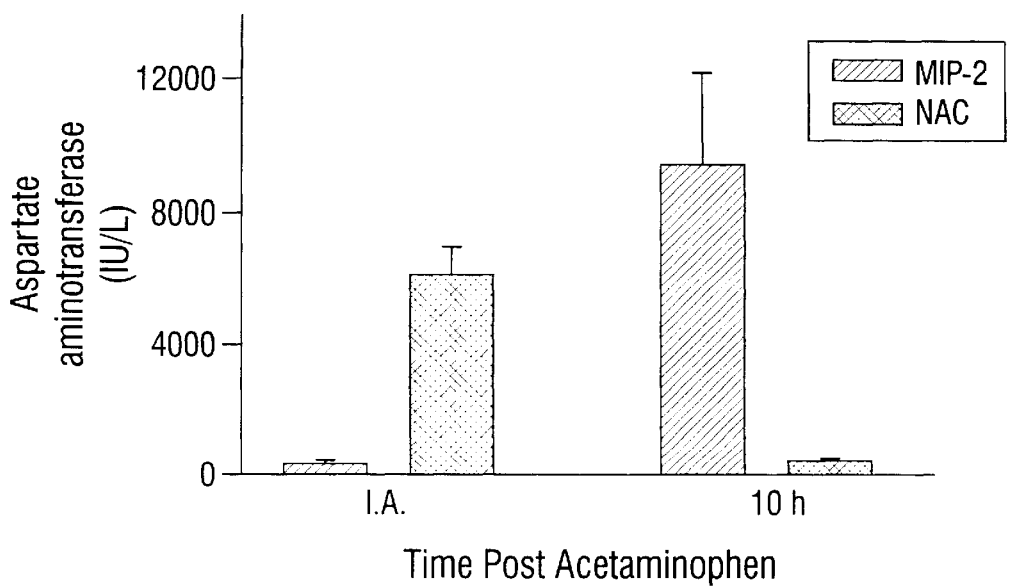
FIG. 8. Serum AST activity in mice fasted for 24 h prior to MIP-2 or NAC treatment immediately after or 10 h after a 400 mg/kg acetaminophen challenge. Blood was removed from each mouse 48 h after acetaminophen challenge for AST determination. When administered immediately following acetaminophen challenge, NAC was more effective than MIP-2 at reducing AST levels. However, when the intervention was delayed 10 h, MIP-2 treatment was more effective than NAC treatment in the reduction of acetaminophen induced elevations in serum AST. Data are means±SE of groups of 5 mice, and * indicates that P≦0.05 compared to control.

Mice that received NAC immediately after acetaminophen challenge had significantly lower levels of serum AST levels than did mice that received MIP-2 at this time (FIG. 8). The converse was observed when the NAC and MIP-2 treatments were delayed for 10 h after acetaminophen challenge. Accordingly, mice in the delayed MIP-2 treatment group had significantly lower levels of serum AST compared to mice that received the delayed NAC treatment.

The histological appearances of the livers from mice that were challenged with acetaminophen and received 100 μg of NAC or 2 μg of murine MIP-2 by i.v. injection, either immediately after or 10 h later, were also analyzed. Mice were fasted for 24 h prior to i.p. injection with 400 mg/kg of acetaminophen, and then allowed free access to food. Forty-eight h later, the liver was removed from each mouse for histological examination.

The histological appearance of liver tissue removed from these groups of mice corroborated the changes in serum AST. When given immediately after acetaminophen, NAC treatment was effective. However, the delayed administration of NAC did not attenuate hepatic injury in acetaminophen-challenged mice. Only mice that received MIP-2 at this time showed improvements, with major restoration occurring in the centrilobular regions most sensitive to acetaminophen.

Taken together, these findings show that delayed MIP-2 therapy is clearly more beneficial than delayed NAC therapy, as evidenced by reduced mouse mortality, serum AST and liver injury in the delayed ELR-CXC chemokine therapy group.

6. ELR-CXC Chemokines Maintain Hepatocyte Proliferation

The liver regenerative properties of ELR-CXC chemokines were confirmed in vitro using a normal hepatocyte cell line. Untreated liver cells were susceptible to the toxic effects of acetaminophen, as evidenced by significantly decreased cell proliferation (monitored by [$^3$H]thymidine incorporation) following exposure to acetaminophen for 24 h (FIG. 9A and FIG. 9B).

Figure 9A:
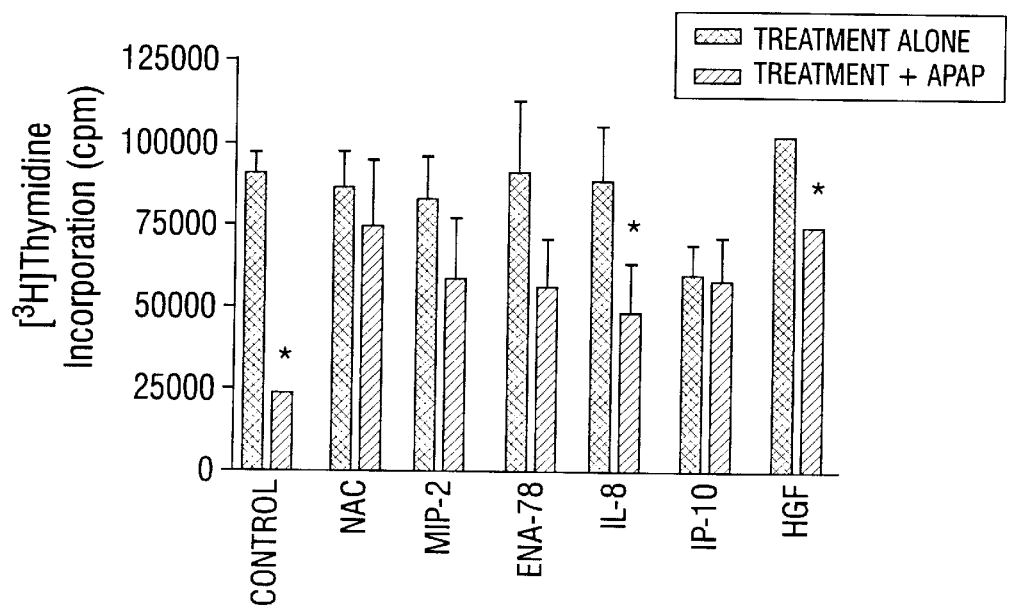
FIG. 9A and FIG. 9B. Proliferation of cultured liver cells exposed to saline (control), NAC, MIP-2, ENA-78, IL-8, IP-10 or HGF in the presence or absence of acetaminophen. Liver cells were treated with NAC (1 mM), cytokines or chemokines (all at 1 ng/ml) either immediately after (FIG. 9A) or 10 h after (FIG. 9B) the addition of PBS or acetaminophen (2.5 mg/ml). Four h prior to the conclusion of a 24 h exposure of the liver cells to PBS or acetaminophen, cultures were pulsed with 10 $\mu$Ci of [$^3$H]thymidine/well, and [$^3$H]thymidine incorporation was determined by liquid scintillation counting. Acetaminophen is abbreviated to APAP in the figure legend. Data are mean +SE of three separate studies. *P≦0.05 compared to respective cultures of hepatocytes that received NAC or cytokine treatment alone.

Although NAC did not alter the proliferation of liver cells exposed to PBS, the addition of NAC to liver cell cultures immediately after acetaminophen maintained the proliferation of these cells at levels approaching those measured in cell cultures challenged with PBS (FIG. 9A). Likewise, MIP-2, ENA-78, IL-8 and HGF did not change the proliferation of liver cells exposed to PBS, but MIP-2 and ENA-78 prevented the drop in liver cell proliferation following exposure to acetaminophen for 24h. Note that the beneficial effects in FIG. 9A are those that prevent a statistically significant reduction in proliferation, and hence are those not marked with *.

Interestingly, the non-ELR CXC chemokine IP-10, which binds CXCR3, when used alone in this in vitro system, lowered the proliferation rate of liver cells exposed to PBS by 40% compared to control cultures with PBS, but the proliferative response of liver cells was not further reduced by the exposure to these cells to acetaminophen.

Figure 9B:
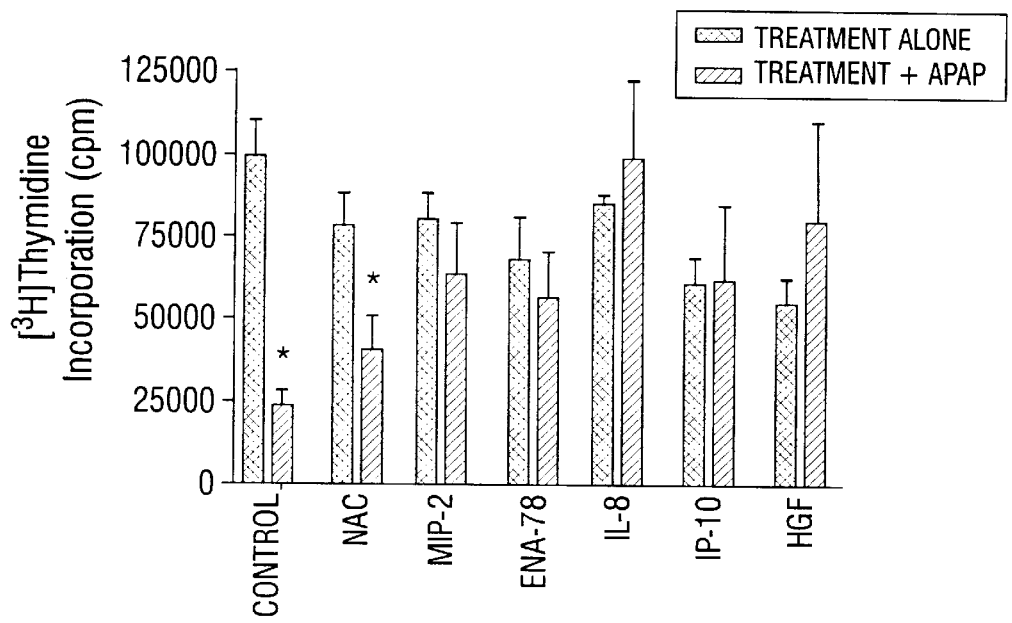

A 10 h delay in the treatment of the liver cells following acetaminophen challenge significantly reduced liver cell proliferation in cultures treated with NAC compared to the respective PBS control cultures (FIG. 9B). In contrast, all other cultures of liver cells exposed to acetaminophen that received delayed cytokine or chemokine treatment showed [$^3$H]thymidine incorporation comparable to cytokine or chemokine treated cultures exposed to PBS. Again, the beneficial effects in FIG. 9B are those without *, and the statistically significant value of delayed NAC treatment is that it is unable to prevent loss of proliferation.

7. ELR-CXC Chemokines Maintain Hepatocyte Proliferation Via CXCR2

Figure 10:
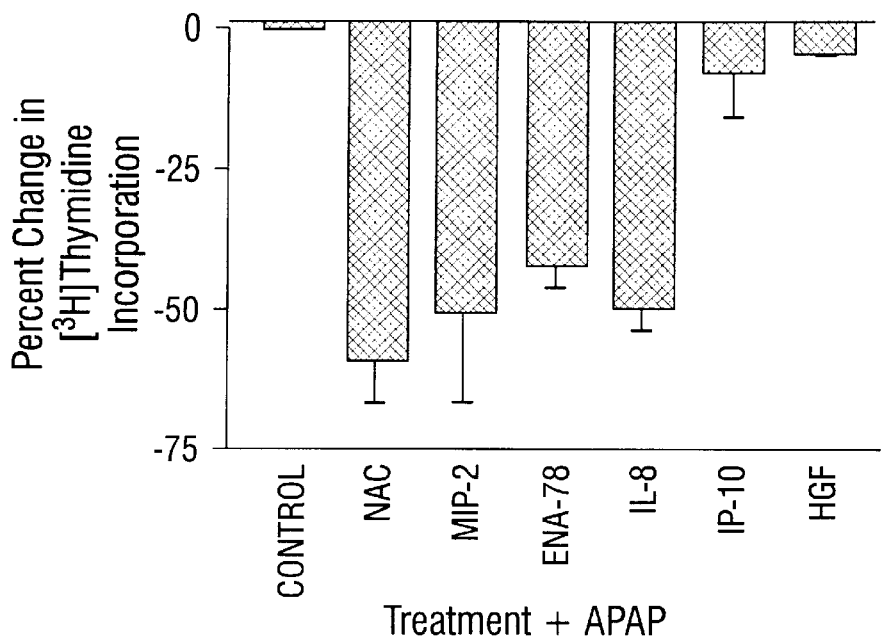
FIG. 10. Role of CXCR2 in the mitogenic effects of saline (control), NAC, MIP-2, ENA-78, IL-8, IP-10 or HGF in cultures of acetaminophen-challenged liver cells. Liver cells were deprived of serum for 36 h prior to exposure to acetaminophen (2.5 mg/ml); and NAC (1 mM), cytokine or chemokine (all at 1 ng/ml) were added 10 h later. Rabbit pre-immune serum or rabbit anti-mouse CXCR2 antibody was added concomitantly with the NAC, cytokine or chemokine treatment. Four h prior to the conclusion of a 24 h exposure of the liver cells to PBS or acetaminophen, cultures were pulsed with 10 $\mu$Ci of [$^3$ H]thymidine/well, and [$^3$H]thymidine incorporation was determined by liquid scintillation counting. Acetaminophen is abbreviated to APAP. Data are mean±SE of three separate studies.

The mitogenic properties of the ELR-CXC chemokines on liver cells are dependent upon their ability to bind to CXCR2. This is shown by the ability of rabbit anti-mouse CXCR2 antibodies to significantly reduce the mitogenic effects of MIP-2, ENA-78 and IL-8 on acetaminophen challenged liver cells (FIG. 10). Interestingly, the presence of anti-CXCR2 antibody also significantly reduced [$^3$H] thymidine incorporation by NAC-treated liver cells exposed to acetaminophen for 24 h.

Overall, these in vitro data suggest that CXC chemokines possess hepatoprotective effects following acetaminophen challenge due partly to their CXCR2-dependent mitogenic effects on liver resident cells.

EXAMPLE III

ELR CXC Chemokine Gene Therapy Attenuate Hepatic Injury

A. Materials and Methods

1. Materials

A replication-defective human type 5 adenoviral construct expressing a functional rat MIP-2 protein was made as described Foley et al. (1996; incorporated herein by reference). This construct, designated as AdMIP-2, has been used to promote MIP-2 protein over-expression in the lung (Foley et al., 1996) and the brain (Bell et al., 1996; incorporated herein by reference). To control for the effects mediated by the adenovirus infection alone, a similar replication-defective human type 5 vector that lacked the MIP-2 gene insert (Ad70-3) was also employed in each study.

Fresh suspensions of acetaminophen (Sigma Chemical Company, St. Louis, Mo.) were made daily by dissolving the drug in phosphate buffered saline (PBS) warmed to 41° C. For immunoneutralization studies and ELISAs, polyclonal antibodies were prepared by multiple-site immunizations of New Zealand White rabbits (Evanoff et al., 1992; incorporated herein by reference). A myeloperoxidase (MPO) ELISA kit was purchased from Calbiochem-Novabiochem Corporation (San Diego, Calif.). All other reagents, unless otherwise specified, were obtained from Sigma Chemical Company (St. Louis, Mo.).

2. Adenovirus Infection and Acetaminophen Challenge

Female CD1, BALB/c, and BALB/c–Cmkar2 tm1Mwm mice 4–8 wk of age were purchased from Jackson Laboratories (Bar Harbor, Me.) and maintained under specific pathogen-free conditions with free access to water and food. BALB/c and BALB/c–Cmkar2 tm1Mwm are referred to throughout this manuscript as CXCR2 wildtype (wt) and CXCR2 knockout (ko), respectively. CXCR2 is the murine CXC chemokine receptor that binds MIP-2 (Lee et al., 1995).

Protocol 1: In the first series of studies, mice received either $1.0 \times 10^8$, plaque forming units (PFU) of Ad70-3 or AdMIP-2 by intravenous (i.v.) injection. Studies by Huard et al. (1995) demonstrated that the liver shows the highest transduction of adenovirus after an i.v. injection. CD1 mice (n=4 mice/group) were sacrificed 24 h after Ad70-3 or AdMIP-2 infection, and serum and liver were removed for histological analysis and MIP-2 measurement by specific ELISA.

Protocol 2: In the second series of studies, CD1, CXCR2ko and CXCR2wt mice were allowed free access to water for 12 h prior to an i.p. injection of 400 mg/kg acetaminophen. All acetaminophen challenged mice were fasted in this manner because previous studies have shown that fasting promotes hepatic susceptibility to acetaminophen toxicity by decreasing the inactivation of chemically reactive metabolites of glutathione, allowing these metabolites to bind hepatocyte proteins and cause cell damage (Whitcomb and Block, 1994; Pessayre et al., 1979; each incorporated herein by reference). CD1 and BALB/c mice have been shown to be sensitive to acetaminophen-induced hepatotoxicity following a 12 h fast (Manautou et al., 1996), but a dose of 400 mg/kg is normally sub-lethal in both strains of mice (Casley et al., 1997). Two hours prior to acetaminophen challenge, CD1 mice (n=1 0/group) were injected with 0.5 ml of normal rabbit serum or anti-mouse MIP-2 antiserum, and mouse survival was monitored for the subsequent 4 days. CXCR2ko and CXCR2wt mice (n=5/group) were injected i.p. with the same dose of acetaminophen, and mouse survival was monitored for 4 days.

Protocol 3: In the next series of studies, CD1, CXCR2wt and CXCR2ko mice were pretreated with either Ad70-3 or AdMIP-2 by i.v. infection 24 h prior to intraperitoneal (i.p.) challenge with acetaminophen. After adenovirus pretreatment and fasting, Ad70-3 and AdMIP-2 pretreated mice (n=4–8 mice/group) were given an i.p. injection of 400 mg/kg acetaminophen, allowed to resume food intake, and mouse survival was monitored over the next 4 days. CD1 mice in both adenovirus pretreatment groups (n=8–10 mice/group) were sacrificed immediately prior to (T=0 h) and 24, 48, or 96 h intervals after an i.p. challenge with 400 mg/kg acetaminophen. CXCR2wt and CXCR2ko mice (n=3/group) were treated in the same way and were sacrificed at 48 h post acetaminophen challenge.

Hepatic tissue and blood were subsequently removed from each mouse for the determination of the parameters described below. Similar samples were also removed from uninfected and PBS challenged mice for determination of baseline values. All liver samples (200–300 mg) were snap frozen in liquid nitrogen and stored at −20° C. prior to ELISA so that samples from each time point could be analyzed in the same assay.

3. Histological Grading of Hepatic Injury

For histological grading of hepatic injury, liver tissues were fixed in 4% paraformaldehyde for 24 h prior to routine histological processing. Hematoxylin and eosin stained slides from adenovirus-pretreated and acetaminophen-challenged mice were assessed by a pathologist in a blinded manner. Separate scoring systems were devised to reflect the area of liver necrosis and hemorrhage, and the extent of hepatic inflammation. Liver necrosis and hemorrhage were determined morphometrically and scored as no liver damage, 0–5%, 6–25%, 26–50%, or >50% of liver area involved. Hepatic inflammation was graded as absent, slight, moderate, or prominent. Detailed histological grading of hepatic injury was determined at 24 h after adenovirus infection and 24, 48 and 96 h after acetaminophen challenge of adenovirus-pretreated mice.

4. Serum Aspartate Aminotransferase and Alanine Aminotransferase.

Acute hepatocellular injury results in elevated levels of aspartate aminotransferase (AST) and alanine aminotransferase (ALT) (Farrell, 1997). In the present study, changes in AST and ALT were monitored in serum removed from adenovirus-pretreated mice at T=0, 24, 48 and 96 h after a 400 mg/kg i.p. acetaminophen challenge. Serum levels of AST and ALT were also determined in CXCR2wt and CXCR2ko mice pretreated with AdMIP-2 and challenged with acetaminophen for 48h. AST and ALT levels were determined by Clinical Pathology at the University of Michigan Medical School (Ann Arbor, Mich.) using standardized techniques.

5. Murine MIP-2 and KC ELISAs

Immunoreactive levels of murine MIP-2 and KC were measured in liver homogenates and serum levels at 24 h after adenovirus infection in CD1 mice using a modified double-ligand ELISA procedure (Evanoff et al., 1992; incorporated herein by reference). Levels of MIP-2 and KC were also measured in liver homogenates prepared from CXCR2wt and CXCR2ko mice pretreated with AdMIP-2 and challenged with acetaminophen for 48 h.

Immediately prior to an ELISA, snap frozen liver samples were thawed on ice, weighed and homogenized in solution containing 2 mg of protease inhibitor (Complete™ Boehringer Mannheim, Indianapolis, Ind.) per ml of normal saline. Complete™ does not interfere with any of the chemokine and cytokine ELISAs (Colletti et al., 1995; incorporated herein by reference). Cell-free supernatants from the liver homogenates were loaded in duplicate into 96-well microtiter plates coated with the appropriate capture antibody, and blocked with 2% bovine serum albumin in PBS. Each ELISA consistently detected concentrations of cytokines and chemokines below 10 $\mu$g/ml, and the specificity of each polyclonal detection and capture antibody was confirmed prior to its use in an ELISA. Cytokine and chemokines levels measured in liver homogenates were normalized to the weight of the liver sample assayed.

6. Measurement of Myeloperoxidase

Studies have shown that MIP-2 is a potent neutrophil chemoattractant both in vitro and in vivo (Frevert et al., 1995; Greenberger et al., 1996). Due to this attribute of MIP-2, liver homogenates were screened for the presence of myeloperoxidase (MPO). MPO is an enzyme found predominately in azurophilic granules of neutrophils, which catalyzes the formation of hypochlorous acid. MPO is commonly used as an index of the activation state or presence of neutrophils in a variety of tissues (Hogaboam et al., 1997; incorporated herein by reference). A commercially-available MPO-specific ELISA was used to determine immunoreactive levels of MPO in liver homogenates. All MPO concentrations were normalized to 1 g of total protein, which was determined using a Bradford assay (BIO-RAD, Hercules, Calif.).

7. In Vivo Tritiated Thymidine Incorporation

Changes in [$^3$H]thymidine incorporation in whole liver were examined in adenovirus-pretreated and acetaminophen-challenged CD1 mice in separate studies. This method has been previously used to monitor hepatic regeneration following acute liver damage (Chanda et al., 1995; incorporated herein by reference). Mice (n=3–5 mice/group) were pretreated with Ad70-3 or AdMIP-2 as described above, and subsequently injected intravenously with 140 $\mu$Ci of [$^3$H]thymidine 4 h prior to the T=0, 24, 48, and 96 h time points after an i.p. challenge with 400 mg/kg of acetaminophen. [3 H]thymidine incorporation was assessed in cell-free supernatants from whole liver homogenates by liquid scintillation counting on a Beckman counter (Beckman Instruments, Fullerton, Calif.).

8. Statistical Analysis

Results are expressed as means±standard error of the mean (SE) of 8–15 mice per group. Survival curves were analyzed by a log-rank test, and a Student's T-test was used to detect significant differences between the Ad70-3- and AdMIP-2-treated groups prior to and following acetaminophen challenge for all other parameters. Statistical calculations were performed using GraphPad Prism 2.0 computer software (San Diego, Calif.), and a P±0.05 was considered statistically significant.

B. Results

1. Adenoviral Liver Injury is Abrogated by Hepatic MIP-2 Overexpression

Hepatocellular injury is a significant side-effect of adenovirus-mediated gene transfer (Nielsen et al., 1998). This injury is the result of direct toxic effects of the adenovirus on the hepatocyte, as well as the hepatic inflammatory response to the adenovirus (Yang et al., 1996). Both responses lead to profound hepatocyte necrosis (Bao et al., 1996; Davern and Scharschmidt, 1998).

The first series of studies addressed the role of MIP-2 in the hepatotoxic response to adenovirus infection in the liver. Twenty-four hours after an i.v. challenge with $1.0 \times 10^8$ PFU of either AdMIP-2 or Ad70-3 in CD1 mice, liver samples were removed for histological analysis. Distinct differences in the histological appearance of the liver were apparent between the Ad70-3 and AdMIP-2 infected mice.

Damaged and vaculated hepatocytes were prominent in Ad70-3-infected mice, and mononuclear and polymorphonuclear cell aggregates, particularly around portal tracts and central veins, were present in many liver sections. However, the hepatic injury due to an i.v. challenge with $1.0 \times 10^8$ PFU of Ad70-3 was relatively short-lived, as liver tissues appeared normal in these mice at 48 and 96 h after adenovirus infection.

In contrast, the liver architecture in AdMIP-2 treated mice was intact with little evidence of hepatocyte injury after 24 h. The histological appearance of liver removed from AdMIP-2-treated mice was similar to that typically seen in uninfected or normal mouse liver. No hepatic injury was noted in AdMIP-2 treated mice at the 48 and 96 h time-points.

Figure 11A:
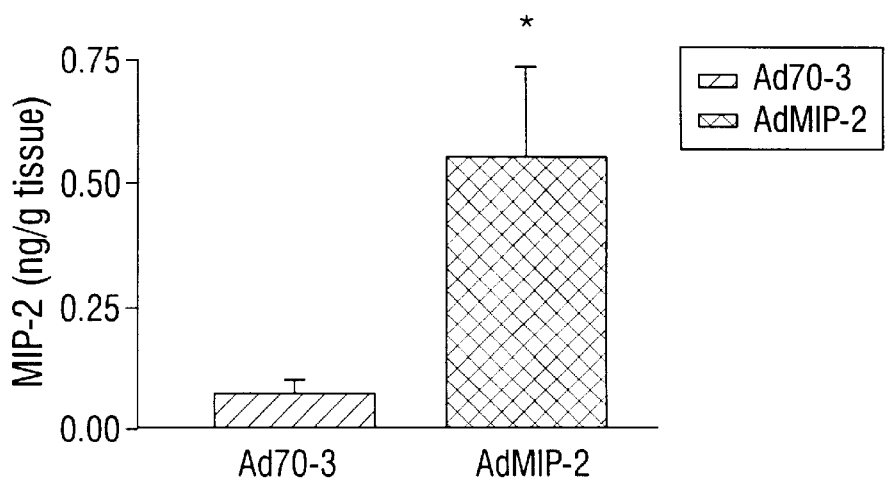
FIG. 11A and FIG. 11B. Macrophage inflammatory protein-2 (MIP-2) (FIG. 11A) and KC (FIG. 11B) levels in liver homogenates from CDI mice injected 24 h previously with 1×10$^8$ PFU of either Ad70-3 or AdMIP-2. Snap frozen livers from both adenovirus groups were thawed, homogenized in buffer containing protease inhibitors and assayed using a specific MIP-2 or KC ELISA. Baseline levels of MIP-2 and KC from untreated mice were 0.04±0.05 ng/g tissue and 0.4±0.15 ng/g tissue, respectively. Data are mean±SE from 8 mice/group. * indicates P±0.05 compared with mice that received Ad70-3.
Figure 11B:
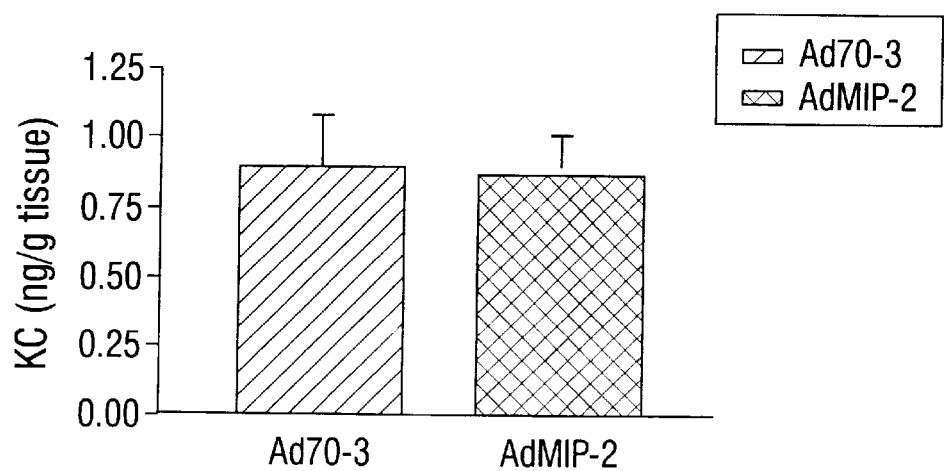

ELISA analysis of liver homogenates from separate mice confirmed that AdMIP-2 infection resulted in a 5-fold increase in levels of immunoreactive MIP-2 above those levels measured in Ad70-3-pretreated mice (FIG. 11A). Immunoreactive levels of KC in the same liver homogenates were not different between the two adenovirus treatment groups (FIG. 11B). Immunoreactive levels of MIP-2 and KC were not detected in serum from either adenovirus treatment group.

2. MIP-2 and CXCR2 Protect Against Acetaminophen Damage

The role of MIP-2 in the hepatic response to acetaminophen challenge was next examined. CD1, CXCR2wt and CXCR2ko mice were fasted for 12 h prior to a 400 mg/kg acetaminophen challenge. In pilot studies, it was observed that after CD1 and BALB/c mice were fasted for 12 h, an i.p. challenge with 400 mg/kg of acetaminophen caused profound hepatic injury but this dose of acetaminophen was lethal to approximately 10% of the mice.

In the present study, 2 h prior to acetaminophen challenge, CD1 mice received 0.5 ml of neutralizing polyclonal anti-MIP-2 immune serum or normal rabbit (control) serum.

Figure 12A:
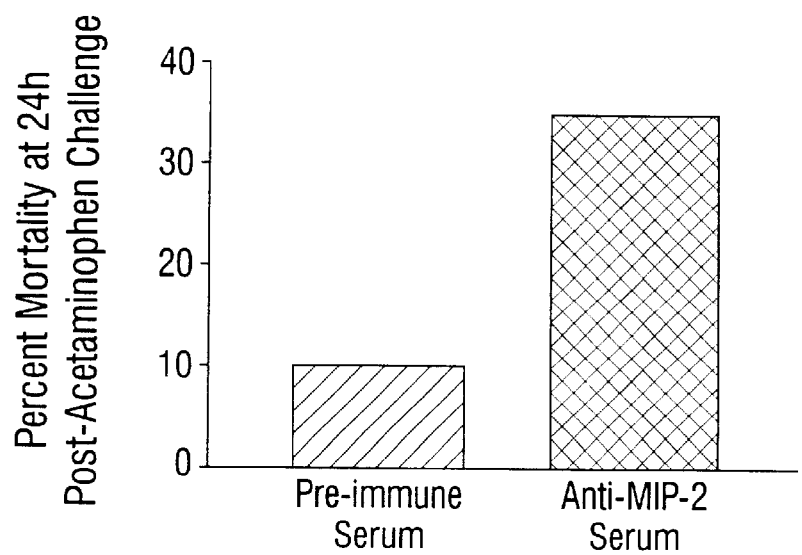
FIG. 12A and FIG. 12B. Survival rates in CD1 (FIG. 12A), and BALB/c CXCR2wt and CXCR2ko (FIG. 12B) mice following an i.p. challenge with 400 mg/kg of acetaminophen. CD1 mice were injected 2 h prior to acetaminophen challenge with 0.5 ml of non-immune rabbit serum or the same volume of rabbit polyclonal anti-MIP-2 immune serum, and all mice were fasted 12 h prior to acetaminophen challenge. Mice that received anti-MIP-2 immune serum were significantly (P≦0.05) more susceptible to the lethal effects of acetaminophen compared to pre-immune serum treated mice. According to a log-rank test, CXCR2ko mice were significantly more susceptible to the lethal effects of acetaminophen compared to CXCR2wt mice. Each treatment group contained a minimum of 4 mice.

CD1 mice that received rabbit anti-mouse MIP-2 antiserum were significantly more susceptible to the lethal effects of acetaminophen challenge (FIG. 12A). Whereas 10% of mice that were pretreated with non-immune rabbit serum died within 24 h of an i.p. challenge with 400 mg/kg of acetaminophen, approximately 35% of the mice pretreated with polyclonal anti-MIP-2 antiserum died within the same time period after acetaminophen challenge (FIG. 12A).

Figure 12B:
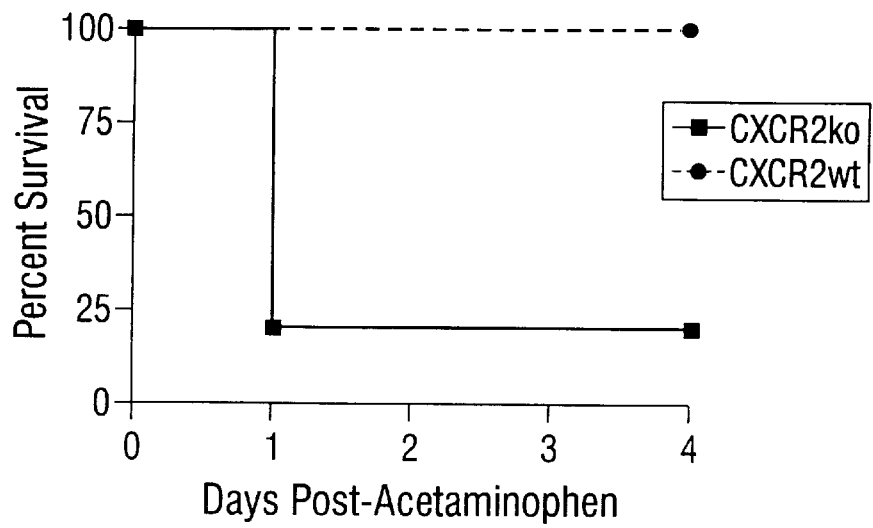

A more pronounced lethal effect of acetaminophen was observed in CXCR2ko mice compared with CXCR2wt mice (FIG. 12B). No deaths were observed in CXCR2wt mice challenged i.p. with 400 mg/kg acetaminophen, but 75% of the CXCR2ko mice were dead at 24 h after acetaminophen challenge (FIG. 12B). These findings suggested that endogenous MIP-2 was protective and CXCR2 expression was necessary for mouse survival following an i.p. acetaminophen challenge.

3. Acetaminophen Lethality is Abrogated by Hepatic MIP-2 Overexpression

Considering that the hepatic injury following AdMIP-2 infection was markedly reduced compared to the injury observed in Ad70-3 infected mice, the next study addressed the effect of an acetaminophen challenge on the survival rates in both adenovirus treatment groups. CD1 mice were pretreated with $1.0 \times 10^8$ PFU of Ad70-3 or AdMIP-2 for 24 h and fasted for 12 h prior to an i.p. challenge with 400 mg/kg of acetaminophen.

Figure 13:
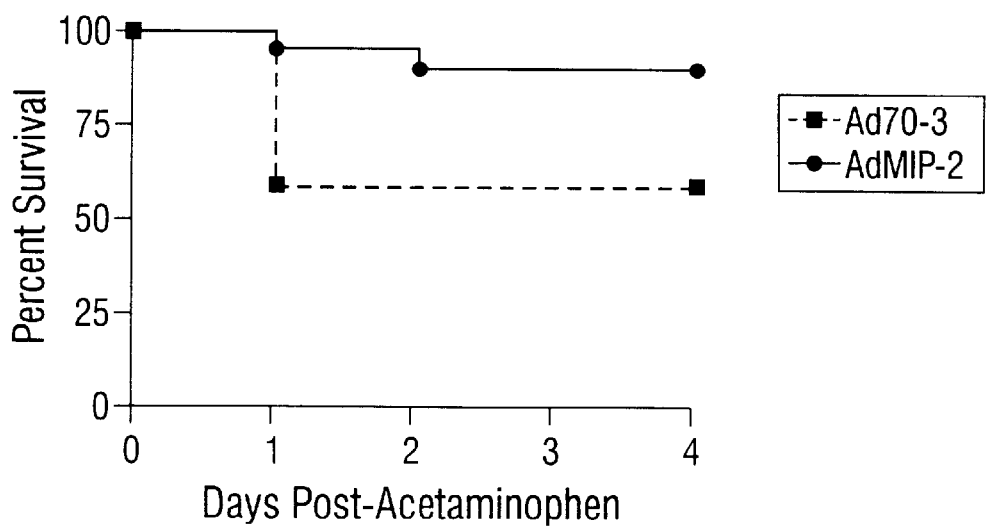
FIG. 13. Survival rates in CDI mice following an i.p. challenge with 400 mg/kg of acetaminophen. The CD1 mice were injected 24 h prior to acetaminophen challenge with 1×10$^8$ PFU of either Ad70-3 or AdMIP-2, and all mice were fasted 12 h prior to acetaminophen. According to a log-rank test, significantly fewer Ad70-3 pretreated mice than AdMIP-2 pretreated mice survived the acetaminophen challenge. Each group contained 8–10 mice.

FIG. 13 shows the effect of acetaminophen challenge on CD1 mouse survival following adenovirus pretreatment. Fifty percent (i.e. 5 out of 10 mice) Ad70-3-pretreated mice were dead at 24 h after acetaminophen challenge, whereas only one mouse in the AdMIP-2 treatment group was dead at this time point. No further deaths were observed Ad70-3 treatment group, but another mouse that received AdMIP-2 was dead at 48 h (FIG. 13). According to a log-rank statistical test AdMIP-2-pretreated mice were significantly less susceptible to the combination of adenovirus infection and acetaminophen challenge than the Ad70-3-pretreated group.

4. Acetaminophen-induced Hepatic Injury is Abrogated by AdMIP-2 Pretreatment

The protective effects of AdMIP-2 pretreatment in acetaminophen challenged CD1 mice were also examined histologically. Hepatic tissues were removed from Ad70-3 and AdMIP-2 pretreated mice at T=24, 48 and 96 h post acetaminophen challenge. The hepatic injury associated with acute acetaminophen challenge is well characterized and includes severe necrosis and hemorrhage in areas surrounding the central veins (Farrell, 1997).

Adenovirus and acetaminophen challenge resulted in moderate to severe centrilobular necrosis in control adenovirus-pretreated mice, with the necrotic area accounting for 40–60% of the total liver area in these mice at 24 h post acetaminophen. Inflammatory infiltrates were prominent in the AD70-3 adenovirus pretreatment group for 48 h after acetaminophen challenge. By 96 h after acetaminophen challenge, the surviving Ad70-3-pretreated mice exhibited relatively normal liver histology. AdMIP-2-pretreated mice exhibited only mild zonal hepatocyte injury with the area of injury accounting for approximately 1–6% of the total liver area, and hepatocyte damage was only apparent at the 24 h time point. At 48 and 96 h after acetaminophen challenge, the liver histology in AdMIP-2 pretreated mice appeared normal.

To confirm that the protective effects of MIP-2 overexpression were mediated through CXCR2, CXCR2wt and CXCR2ko mice were pretreated with AdMIP-2 or Ad70-3 for 24 h prior to acetaminophen challenge. ELISA analysis of liver homogenates from AdMIP-2 pretreated CXCR2wt and CXCR2ko mice confirmed that hepatic MIP-2 levels were similar in these mice: CXCR2wt=1.8±0.3 ng/g tissue vs. CXCR2ko=2.1±0.5 ng/g tissue. Liver histology was examined in these mice at 48 h post acetaminophen. AdMIP-2 pretreatment of CXCR2wt mice prevented the acetaminophen-induced liver injury observed in CXCR2wt mice pretreated with Ad70-3. No similar protection was afforded by AdMIP-2 infection in CXCR2ko mice since histological liver injury in these mice was similar to that observed in CXCR2ko mice that received Ad70-3 prior to acetaminophen challenge.

5. AdMIP-2 Pretreatment Abolishes AST and ALT Increases

AST and ALT levels are commonly used as indirect markers of hepatic function following suspected acetaminophen toxicity (Farrell, 1997). Temporal changes in AST and ALT levels prior to (T=0) and after acetaminophen challenge in adenovirus-pretreated CD1 mice are summarized in FIG. 14A and FIG. 14B, respectively.

Interestingly, AST and ALT levels were not increased above control levels (i.e. AST=125±41 IU/L and ALT=23±4 IU/L) in mice injected with Ad70-3 or AdMIP-2 prior to acetaminophen challenge. Additionally, no increases in AST or ALT were observed at 48 or 96 h after infection with either adenovirus.

Figure 14A:
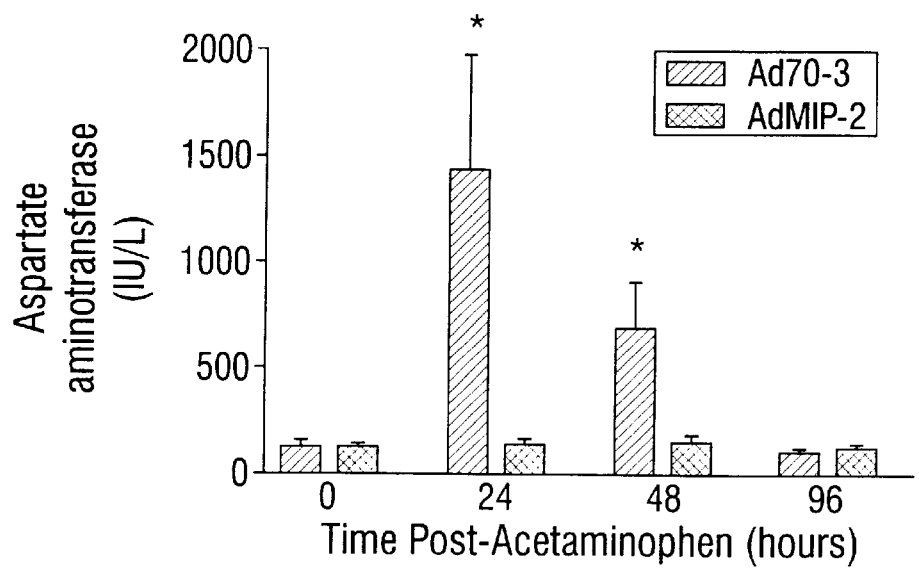
FIG. 14A and FIG. 14B. Temporal changes in aspartate aminotransferase (AST) (FIG. 14A) and alanine aminotransferase (ALT) (FIG. 14B) levels in serum samples from CD1 mice pretreated with $1\times10^8$ PFU of either Ad70-3 or AdMIP-2, and challenged i.p. with 400 mg/kg of acetaminophen. All mice were fasted for 12 h prior to acetaminophen challenge. Baseline levels of AST and ALT from untreated CD1 mice were 125±41 IU/L and 23±4 IU/L, respectively. Data are mean±SE from 8 mice/group. * indicates P±0.05 compared with mice that received AdMIP-2.

However, at 24 h after acetaminophen challenge in both groups clear differences in AST and ALT levels were apparent. Specifically, AST levels were elevated approximately 10-fold above baseline levels in Ad70-3-pretreated mice, but AST levels were unchanged in AdMIP-2-pretreated mice at 24 h post acetaminophen challenge (FIG. 14A). At 48 h, Ad70-3-pretreated mice exhibited AST levels that were approximately 5-fold above baseline levels, but no evidence of significantly elevated AST levels were apparent in AdMIP-2-pretreated mice. At 96 h, levels of AST in both groups of adenovirus pretreated mice were similar to baseline values.

Figure 14B:
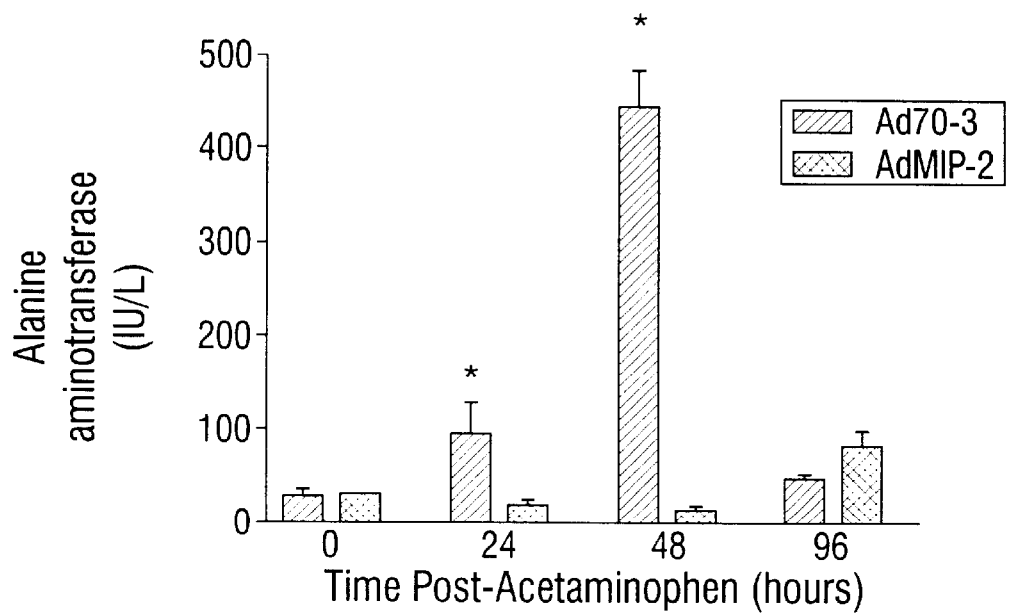

Changes in ALT levels followed a similar pattern in Ad70-3-pretreated mice and ALT were significantly elevated at 24 and 48 h post acetaminophen challenge (FIG. 14B), and maximal ALT levels were observed at 48 h in this control adenovirus group. ALT levels were not significantly elevated above baseline at any time point after acetaminophen challenge in AdMIP-2-pretreated mice (FIG. 14B).

Figure 15:
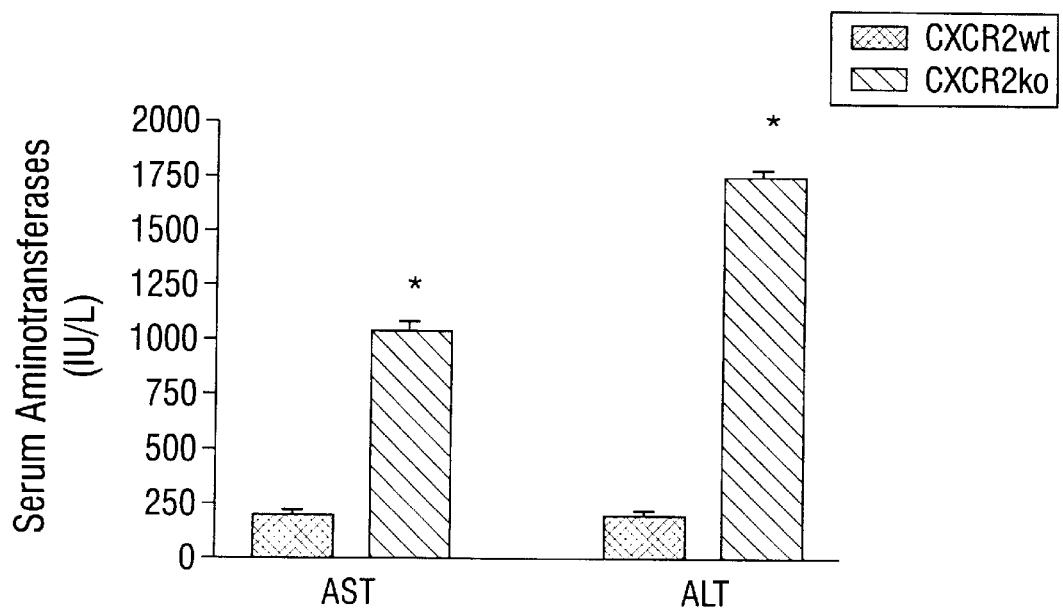
FIG. 15. Aspartate aminotransferase (AST) and alanine aminotransferase (ALT) levels in serum samples from CXCR2wt and CXCR2ko mice pretreated with $1\times10^8$ PFU of AdMIP-2, and challenged i.p. with 400 mg/kg of acetaminophen. All mice were fasted for 12 h prior to acetaminophen challenge. Serum was removed from both groups of mice at 48 h post acetaminophen challenge. Baseline levels of AST and ALT from untreated CXCR2wt mice were 178±50 IU/L and 72±8 IU/L, respectively. Data are mean±SE from 3 mice/group. * indicates P±0.05 compared with CXCR2wt mice.

CXCR2 expression appeared to be required for the protective effect of MIP-2 overexpression since pretreatment of CXCR2ko mice with AdMIP-2 did not prevent the profound elevations in AST and ALT levels 48 h after acetaminophen challenge, as was observed in AdMIP-2 pretreatment in CXCR2wt mice did (FIG. 15).

Figure 16:
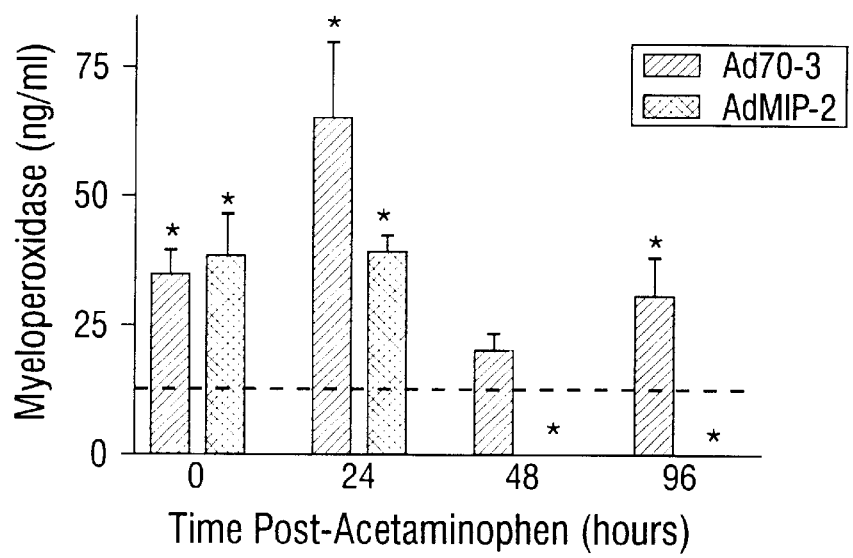
FIG. 16. Temporal changes in myeloperoxidase levels in liver samples removed from CD1 mice pretreated with $1\times10^8$ PFU of either Ad70-3 or AdMIP-2, and challenged i.p. with 400 mg/kg of acetaminophen. All mice were fasted for 12 h prior to acetaminophen challenge. The dashed line denotes the mean baseline MPO levels in untreated CD1 mice (13±1 ng/ml). Data are mean±SE from 8 mice/group. * indicates P±0.05 compared with mice that received AdMIP-2.

6. AdMIP-2 Protection is Not Mediated by Increased Hepatic Neutrophil Infiltration Previous studies have demonstrated that endogenously generated MIP-2 and KC within the acutely injury liver are responsible for neutrophil recruitment (Lentsch et al., 1998). In the present study, changes in neutrophil recruitment to the liver following adenovirus infection and acetaminophen challenge were examined indirectly using a specific ELISA for MPO (FIG. 16).

Baseline levels of MPO in hepatic homogenates from normal CD1 mice were 13±1 ng/ml. Hepatic MPO levels were increased approximately 3-fold above baseline to 38±11 ng/g tissue in AdMIP-2-pretreated mice and 35±7 ng/ml in Ad70-3-pretreated mice 24 h after adenovirus injection (P=0.053 and 0.014, respectively). Whereas MPO levels were not further increased in AdMIP-2-pretreated mice at 24 h post acetaminophen challenge, MPO levels in Ad70-3 were increased 5-fold above baseline to 65±22 ng/ml (P=0.046). At the 48 and 96 h time point following acetaminophen challenge, MPO was absent in the AdMIP-2 pretreated mice, but MPO values remained significantly (P=0.019) elevated above the baseline in Ad70-3 pretreated mice at 96 h after acetaminophen (FIG. 16).

These data suggested that the hepatoprotective effects of MIP-2 overexpression in the liver were not mediated by increased neutrophil recruitment to the acutely injured liver. Instead, increased MIP-2 levels in the liver appeared to modulate the hepatic inflammatory response typically elicited by the adenovirus and acetaminophen challenge.

7. AdMIP-2 Promotes Rapid Hepatoproliferation Following Acetaminophen Challenge

Figure 17:
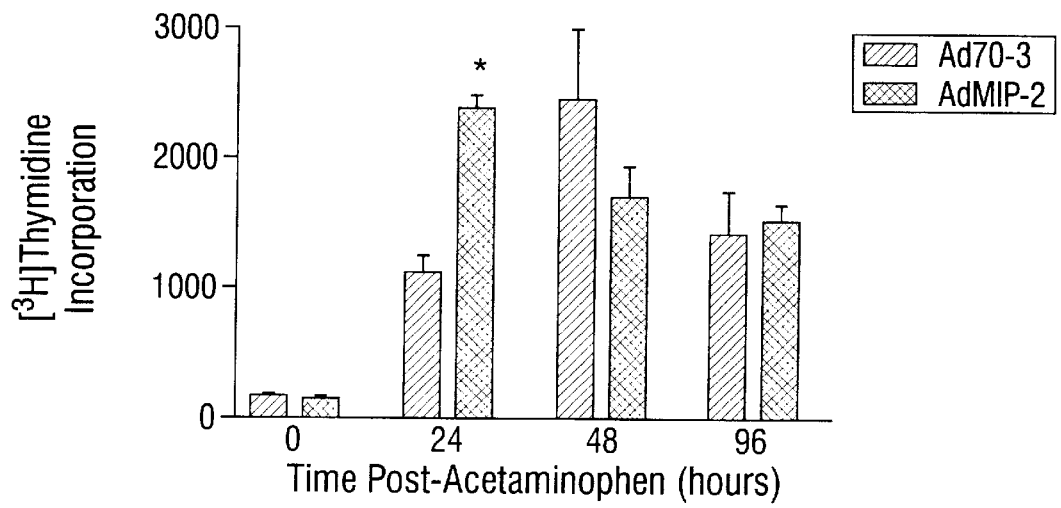
FIG. 17. Temporal changes in [$^3$H]thymidine incorporation by whole livers removed from CD1 mice pretreated with $1\times10^8$ PFU of either Ad70-3 or AdMIP-2, and challenged i.p. with 400 mg/kg of acetaminophen. All mice were fasted for 12 h prior to acetaminophen challenge. [$^3$H] thymidine was given by i. v. injection 4 h prior to each time point examined post-acetaminophen. Time 0 represents the time point 24 h after adenovirus treatment and immediately prior to acetaminophen challenge. [$^3$H]thymidine incorporation in whole livers from mice that did not receive adenovirus or acetaminophen was approximately 1000 cpm. (i.e. the normal baseline for [$^3$H]thymidine incorporation). Data are mean±SE from 4 mice/group. * indicates P±0.05 compared with mice that received Ad70-3.

FIG. 17 illustrates the temporal change in [$^3$H]thymidine incorporation in whole liver preparations from Ad70-3 and AdMIP-2 pretreated CD1 mice after acetaminophen challenge. In uninfected or normal CD1 mice, hepatic [$^3$H] thymidine incorporation was less than 1000 cpm. No differences in hepatic incorporation of [$^3$H]thymidine were apparent immediately prior to acetaminophen challenge and 24 h after either adenovirus treatment, but hepatic [$^3$H]thymidine incorporation was increased approximately 7-fold from a normal baseline of 1000±200 cpm./liver to 7434±246 cpm./liver in both adenovirus groups.

Hepatic [$^3$H]thymidine incorporation in AdMIP-2 pretreated mice was increased another 4-fold to 23991±956 cpm./liver at 24 h after acetaminophen. In Ad70-3 pretreated mice, hepatic [$^3$H]thymidine incorporation was increased less than 2-fold after 24 h of acetaminophen challenge. The difference in hepatic [$^3$H]thymidine incorporation between the two adenovirus treatment groups was found to be statistically significant at the 24 h time point following acetaminophen challenge.

These findings show that hepatic MIP-2 overexpression promotes a rapid proliferative response by liver cells following acetaminophen challenge.

At 48 h post acetaminophen, the hepatic [$^3$H]thymidine incorporation was increased in the Ad70-3 pretreated group as well as the AdMIP-2 pretreated mice. At 96 h post-acetaminophen, hepatic [H]thymidine remained elevated above baseline levels of hepatic [$^3$H]thymidine incorporation in both adenovirus pretreatment groups (FIG. 17).

EXAMPLE IV

Mechanism of MIP-2-induced Hepatocyte Proliferation In Vivo

A. Materials and Methods

1. Acetaminophen-induced Hepatic Injury

Female CD-1 (6–8 wk of age) were purchased from Charles River Laboratories (Portage, Mich.) and maintained under specific pathogen-free conditions with free access to water and food prior to each study. Fresh suspensions of acetaminophen (APAP, Sigma Chemical Company, St. Louis, Mo.) were made daily by dissolving the compound in phosphate-buffered saline (PBS) warmed to 50° C. In all studies, mice were deprived of food but not water for 18 h prior to an acetaminophen challenge. Acetaminophen was given to each mouse by intraperitoneal (i.p.) injection at a dose of 400 mg/kg as described previously in detail (Examples 1–111; Hogaboam et al., 1999a).

2. Protocols

Fasted mice received either PBS (0.5 ml) as control or 1 μg MIP-2 (Peprotech) dissolved in 0.5 ml of PBS via an intravenous (i.v.) injection at 10 h after the acetaminophen challenge. Liver and serum samples were removed from each mouse at 4, 8, 26, 34, 40, and 48 h after PBS or MIP-2 administration. In a separate study, mice received either 0.8 mg of IgG, anti-MIP-2 antibody or anti-CXCR2 antibody via an i.v. injection at 10 h after an acetaminophen challenge.

Both polyclonal antibodies were generated in rabbits, affinity column purified, and screened to ensure specificity prior to use in this study as previously described (Evanhoff et al., 1992). The biological half-life of both immunoneutralizing antibodies was approximately 36 hrs. (Colletti et al., 1996). These mice were killed at 24 and 48 h after Ig or antibody treatment, and liver and serum samples were processed as described below. In both studies, in vivo labeling of proliferating hepatocyte was facilitated by the i.p. administration of 30 μg/g of BrdU (Sigma) at 2 h intervals for at total of 6 h prior to sacrifice.

3. Histology and Immunohistochemistry

A portion of resected liver from each mouse was immediately fixed in 4% paraformaldehyde for a minimum of 12 h. Fixed liver samples were subsequently processed, embedded in paraffin, thin-sectioned, and placed on L-lysine-coated slides. Hematoxylin and eosin (H&E) staining was used to reveal morphometric differences between each group of mice.

Additional slides containing unstained liver sections were used for immunohistochemical analysis. These slides were first deparaffinized by sequential treatment with xylene, 100% EtOH, 90% EtOH, 70% EtOH, 50% EtOH, distilled water, and PBS. To reveal BrdU labeling, these slides were then incubated in 1 N HCl at 37° C. for 1 h, washed three times in PBS, and incubated for 20 min in 1% $H_2O_2$ in methanol and washed. All slides were then blocked using a 1:2 dilution of normal rabbit serum for 1 h.

Tissue sections were treated with monoclonal anti-BrdU antibody (Chemicon, Temecula, Calif.) at 1:100 with PBS containing blocking solution for 2 h at 37° C. in a humidified chamber. After incubation, each slide was washed three times with PBS. A 1:300 dilution of horseradish peroxidase-labeled goat anti-mouse antibody (Pierce, Rockford, Ill.) was placed on the slides for 2 h at 37° C. in a humidified chamber. Slides were again washed twice in PBS. Slides were developed using a DAB kit (Vector, Burlington, Calif.) and counterstained with Mayer's hematoxylin (0.1%; Sigma). BrdU-positive hepatocytes with uniformly round staining nuclei were counted in ten of the least necrotic fields of view (200×).

To reveal the presence of CXCR2 in liver sections, other slides were deparaffinized, microwaved for approximately 20 min in 10 mM citric acid buffer, and then allowed to cool to room temperature. Slide-mounted liver sections were blocked using normal goat serum (blocking solution) for 1 h. Tissue sections were treated with purified polyclonal anti-mouse CXCR2 antibody or rabbit IgG for control. All were diluted at 1:25 with TBS containing blocking solution (1:100) and incubated overnight at 4° C. After incubation, slides were washed twice for 5 min in TBS. A 1:35 dilution of biotinylated goat anti-rabbit antibody (BioGenex, San Ramon, Calif.) was placed on the slides for 2 h at 37° C. in a humidified chamber.

Slides were again washed twice in TBS, and incubated with a 1:35 dilution of streptavidin conjugated to horseradish peroxidase (BioGenex) for 45 min. Following two washes in TBS with 50 mM levamisole, fast red chromogen (BioGenex) was placed on each slide, and staining was visualized at low power until color development was complete. The staining reaction was terminated in sterile water, and each slide was counterstained with Mayer's hematoxylin (0.1%; Sigma).

4. Nuclear Extraction and Direct Lysis of Nuclei

Preparation of nuclear extracts from liver was conducted as follows. Briefly, liver samples were rapidly homogenized in PBS containing Complete$^{TB}$ protease inhibitor (10 mg/ml; Boehringer Mannheim) on ice and washed with fresh PBS. Homogenates were then suspended in Buffer A (10 mM Hepes, 10 mM KCl, 0.5mM DTT, 1% NP-40) for 10 min and centrifuged for 10 min at 14,000×g and the supernatant containing cytoplasmic components was removed. The cell nuclei (found in the pellet) were suspended in Buffer C (20 mM Hepes, 20% glycerol, 500 mM KCl, 0.2 mM EDTA, 0.5mM PMSF, 0.5mM DTT, 1.5 mM MgCl$_2$) for 15 min and centrifuged at 7,000×g for 10 min. The supernatant containing the nuclear proteins was removed for Western Blot analysis.

5. Western Blot Analysis

After nuclear protein levels were determined using a Bradford assay (Bio-Rad), 50 μg of liver nuclear extracts were electrophoresed on a 12% polyacrylamide gel and then transferred to a PVDF membrane (Bio-Rad). Equal protein loading was confirmed by Coomassie blue staining of the gel after transfer. PVDF membranes were blocked for 1 h at room temperature in 5% dry milk. STAT-3, C/EBP-β, C/EBP-α and cyclin D1 antibodies (Santa Cruz Biotechnology, Inc.) were diluted to 1:1,000 (C/EBP-β was diluted 1:500) and incubated with PVDF membranes overnight at 4° C. Horseradish peroxidase-linked secondary antibody (Pierce) were then added at a 1:3,000 dilution for 2 h at room temperature, and protein bands were visualized by chemiluminescence (Bio-Rad).

6. Statistical Analysis

Results are expressed as means±standard error of the mean (SEM) of 5–10 mice per group at each time point after treatment. All statistical calculations were performed using GraphPad Prism 2.0 computer software (San Diego, Calif.); $P \leq 0.05$ was considered statistically significant.

B. Results

1. Exogenous MIP-2 Promotes Rapid Recovery From Liver Injury

The delayed exogenous administration of recombinant MIP-2, working through CXCR2, is therapeutic in a murine model of acetaminophen toxicity (Examples I–III; Hogaboam et al., 1999a). It appeared that this therapeutic effect was mediated through a direct effect of MIP-2 on the proliferation of hepatocytes (Examples 1–111; Hogaboam et al., 1999a). The aim of the present example is to explore in more detail the role of MIP-2 and CXCR2 in the cellular events leading to hepatocyte proliferation during in vivo acetaminophen toxicity.

An i.p. challenge of mice with 400 mg/kg of acetaminophen caused hepatic necrosis and hemorrhage exclusively in the centrilobular region of the liver, and this injury was prominent in histological sections 2 days after the acetaminophen challenge. These mice also received 0.5 ml of PBS by i.v. injection at 10 h after the acetaminophen challenge. In contrast, mice that received 1 μg of MIP-2 by i.v. injection at 10 h after the acetaminophen challenge exhibited little evidence of liver injury at 2 days after MIP-2 injection, and the area around the central vein contained newly regenerated hepatocytes with evidence of a mitotic figure. It should be noted that both groups of mice exhibited the same degree of liver injury at 10 h after acetaminophen challenge immediately prior to the i.v. injection. Thus, these data confirm that MIP-2 has dramatic therapeutic potential related to hepatocyte regeneration, particularly following acetaminophen toxicity.

2. MIP-2 and CXCR2 are Required for the Maintenance of Liver Integrity

Even at 6 days after a sub-lethal dose of acetaminophen, the hepatic integrity of mice that received anti-MIP-2 antiserum remained severely compromised, whereas mice that received preimmune serum exhibited completely restored livers at this time (Examples I–III; Hogaboam et al., 1 999a). The present example confirms the endogenous role of MIP-2 and CXCR2 during acetaminophen toxicity using purified polyclonal antibodies.

Mice received either 0.8 mg of IgG, anti-MIP-2 or anti-CXCR2 at 10 h after the acetaminophen challenge. In mice that received IgG, there was marked evidence of necrosis of the hepatocytes particularly around the central vein at 2 days after receiving IgG treatment. In mice that received anti-MIP-2 antibody, the hepatic architecture was completely destroyed. More dramatically, the neutralization of CXCR2 in acetaminophen--20 challenged mice proved lethal as none of these mice were alive at 2 days after receiving anti-CXCR2 antibody. Autopsy of these mice revealed profound liver hemorrhage. Thus, these data show that the presence of endogenous MIP-2 and CXCR2 are required for the liver to recover from a sub-lethal dose of acetaminophen.

3. Hepatocytes Express CXCR2

To show that hepatocytes constitutively express CXCR2, and the impact of acetarninophen on CXCR2 levels in the liver, immunohistochemical analyses of whole liver sections were performed. These revealed that CXCR2 expression was present on hepatocytes situated around the central veins, and CXCR2 expression by these cells was markedly increased after an acetaminophen challenge. A major increase in CXCR2 expression was observed on hepatocytes around central veins at 48 h after the acetaminophen challenge. Negative controls for each group validate this study.

To further investigate the temporal change in CXCR2 expression prior to and after acetaminophen challenge, CXCR2 protein levels were quantified using Western blot analysis. Prior to acetaminophen challenge, cytoplasmic preparations from liver homogenates contained relatively small amounts of CXCR2 protein (42-kDa band). Four hrs. after the acetaminophen challenge, CXCR2 expression was not present, but by 8 h after acetaminophen, CXCR2 protein expression was detectable again (84-kDa band). However, the greatest hepatic levels of CXCR2 were observed at 24 and 48 h after the acetaminophen challenge in untreated mice. At 120 h after the acetaminophen challenge, CXCR2 protein was not detected using Western blot analysis. The presence of a band at 84-kDa reflects the fact that CXCR2 could exist as a dimer as has been seen with other chemokine receptors (Hogaboam et al., 1999b).

4. MIP-2 Therapy Directly Affects Hepatocyte Proliferation During Challenge

MIP-2 can influence the proliferation of cultured hepatocytes (Examples I–III; Hogaboam et al., 1999a). To show that hepatocyte proliferation is a major mechanism through which MIP-2 promotes liver protection from acetaminophen toxicity in vivo, the inventors examined hepatocyte proliferation at various times after an acetaminophen challenge by BrdU, which reveals cells that are in the S-phase of the mitotic cycle.

Figure 18:
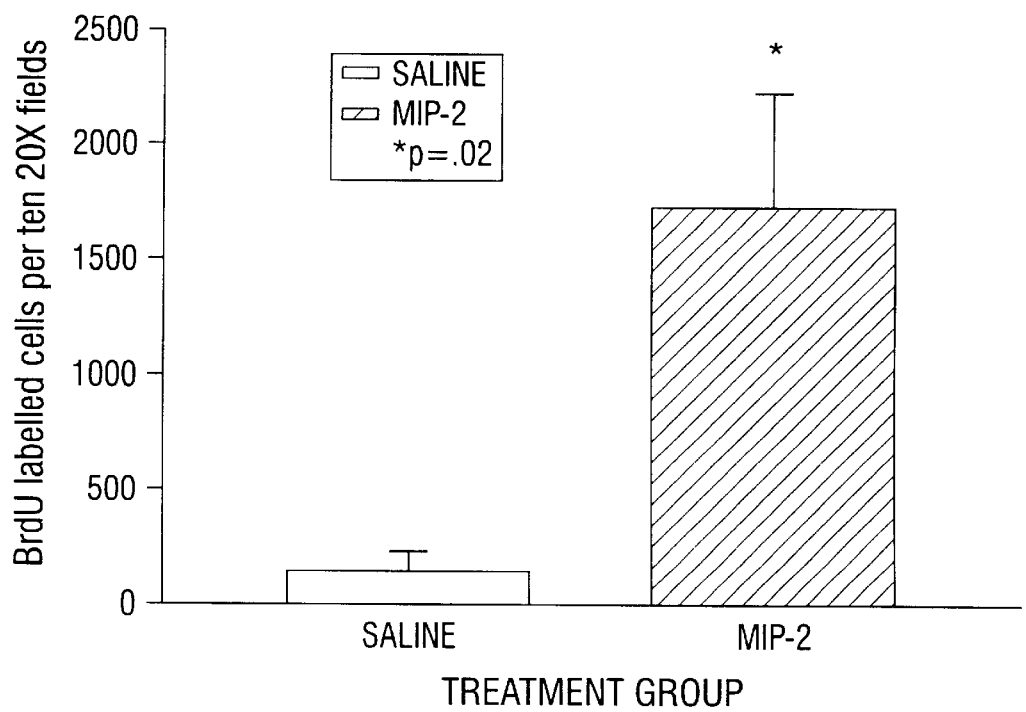
FIG. 18. Significantly greater hepatocyte proliferation was detected in liver from acetaminophen-challenged mice that received MIP-2 therapy. At 48 h after receiving PBS, BrdU-labeled hepatocytes were predominantly located around the central veins of acetaminophen-challenged mice. In contrast, at the same time after receiving MIP-2 therapy, there were dramatically more BrdU-positive hepatocytes scattered throughout the livers of acetaminophen-challenged mice. Quantitative analysis of BrdU-labeled hepatocyte nuclei in both groups revealed that acetaminophen-challenged mice that received MIP-2 had significantly (P=0.02) greater BrdU labeled hepatocyte nuclei per ten 200×fields. When administered to mice prior to acetaminophen challenge, less than five BrdU-labeled cells were detected in ten 200×fields. Data are means±SE, n=4 to 5 mice/group.

All mice were given three injections of 30 μg/g of BrdU (i.p.) over 6 h prior to sacrifice. In mice that received PBS after the acetaminophen challenge, few BrdU-positive hepatocytes were observed around the central veins at 48 h after PBS injection. Conversely, exogenous MIP-2 injection at 10 h after acetaminophen challenge markedly increased the number of BrdU-positive hepatocytes detected at 48 h after the treatment. BrdU-positive hepatocyte nuclei were detected around the central vein, and throughout the entire hepatic lobule. Quantitative analysis in both groups at this time revealed that the MIP-2 treatment enhanced hepatocyte incorporation by 10-fold (p=0.02) above that observed in the control group (FIG. 18). Conversely, livers not exposed to acetaminophen contained less than 5 BrdU-labeled cells in ten 200×microscope fields.

Cyclin D1 is another marker for the cell cycle progression and it is induced when cells enter the cell cycle from quiescence (Sherr, 1996). Cyclin D1 protein expression was examined using Western blot analysis of nuclear extracts from both treatment groups to further confirm the proliferative effect of MIP-2 during acetaminophen challenge. There were markedly greater nuclear levels of cyclin D1 protein (34-kDa band) in mice that received MIP-2 compared with control mice at 24 h after treatment. Cyclin D1 levels were not detected in nuclear extracts from mice prior to the acetaminophen challenge. Thus, these findings demonstrated that MIP-2 therapy after a sub-lethal acetaminophen challenge was associated with a marked increase in cellular events consistent with hepatocyte proliferation.

5. MIP-2 Therapy Promotes The Nuclear Translocation Of Transcription Factors

The effects of exogenous MIP-2 therapy on the nuclear translocation of transcription factors that are necessary for hepatocyte proliferation, such as C/EBP-β, C/EBP-α and STAT-3, were examined in acetaminophen challenged mice. C/EBPβ is a liver-enriched transcription factor (Descombes et al., 1990) and mRNA and protein levels of this transcription factor are increased during liver regeneration after partial hepatectomy (Trautwein et al., 1996a). Furthermore, C/EBP-β-knockout (ko) mice exhibit a dramatic decrease in hepatocyte DNA synthesis after hepatectomy (Greenbaum et al., 1998). In contrast, C/EBP-α is most abundant in differentiated liver cells (Nagy et al., 1994) and mRNA and protein decline transiently after partial hepatectomy (Greenbaum et al., 1998). In C/EBP-α-ko mice, there is an increase in DNA synthesis and an increase in the frequency of hepatocyte immortalization (Soriano et al., 1998). Similar to C/EBP-β, nuclear translocation of STAT3 is a critical early event during liver regeneration (Cressman et al., 1995; Trautwein et al., 1996b) that is impaired in IL-6-ko mice, which lack hepatocyte proliferation and liver regeneration (Cressman et al., 1996).

MIP-2 therapy stimulated a rapid increase in both liver activating protein (LAP) isoforms of C/EBP-β in nuclear extracts from liver homogenates. It should be noted that nuclear protein expression of C/EBP-β is regulated at the transcriptional and post-translational level (Trautwein et al., 1993), and levels of C/EBP-β are elevated in the nucleus before the hepatocyte enters the S-phase of the cell cycle.

In mice that received PBS after the acetaminophen challenge, there were no detectable levels of C/EBP-β until 10 h after PBS was administered. Conversely, in mice given MIP-2 therapy, nuclear expression of the 38- and 35-kDa LAP of C/EBP-β was evident at 4 h after MIP-2 treatment. By 30 h after the MIP-2 therapy, the LAP isoforms of C/EBP-β had already begun to diminish, yet maximal expression of the LAP isoforms of C/EBP-β was not observed until 34 h after PBS administration to similarly acetaminophen-challenged mice. The difference in the level of expression of C/EBP-β between the two groups of mice is highlighted by studies of nuclear C/EBP-β protein levels at 8 h in three separate mice from both groups. These data demonstrate that MIP-2 therapy accelerates the proliferation of hepatocytes in acetaminophen-challenged mice through a C/EBP-β-dependent mechanism.

C/EBP-α is the principal C/EBP isoform that is constitutively expressed by adult hepatocytes in the healthy liver (Diehl, 1998). At 8 h after receiving PBS, acetaminophen-challenged mice expressed little C/EBP-α, probably reflecting the fact that the liver was in a necrotic state. However, at 8 h after receiving MIP-2 therapy, acetaminophen-challenged mice exhibited nuclear expression of the 48- and 42-kDa isoforms of C/EBP-α, suggesting that viable hepatocytes were present in these mice at this time. At 24 h after PBS or MIP-2 therapy, there was greater nuclear expression of C/EBP-α in liver from control mice than in similar samples from the other group of mice, suggesting that viable hepatocytes were present in both groups at this time. These data show that MIP-2 therapy rapidly accelerates the in vivo hepatic regeneration events in the acetaminophen-challenged liver.

Since STAT-3 is a critical transcription factor for liver regeneration and hepatocyte proliferation, the temporal changes in nuclear levels of STAT-3 were examined in both groups. STAT-3 (92-kDa band) was strongly expressed at all times examined after MIP-2 therapy compared with acetaminophen-challenged mice that received PBS, in which there were much lower levels of nuclear expression of STAT-3 at all times examined. To further illustrate the enhancing effect of MIP-2 therapy on the nuclear expression of STAT-3, three mice from both groups were examined at 8 h and 24 h after PBS or MIP-2 therapy. At both time points, mice that received MIP-2 therapy showed greater nuclear expression of STAT-3 protein compared with the control group.

6. Neutralization of MIP-2 and CXCR2 Reduces Hepatocyte Proliferation

Figure 19:
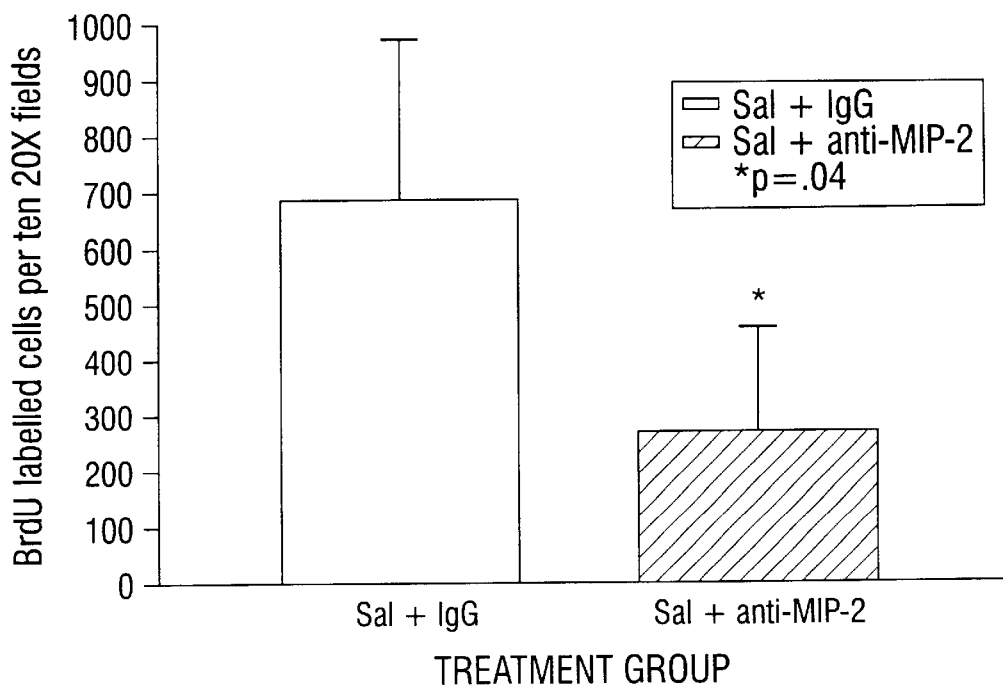
FIG. 19. Neutralization of MIP-2 dramatically decreased hepatocyte proliferation 48 hrs. after treatment. Forty-eight hrs. after control IgG treatment, there are a small number of BrdU-labeled hepatocytes present. After neutralization of MIP-2, there were strikingly fewer BrdU-labeled hepatocyte nuclei in the liver. While the IgG treated group had a low level of BrdU-labeled hepatocyte nuclei per ten 20×fields (similar to the saline-treated group), the anti-MIP-2 treated group had a five-fold fewer (*p=.04). Data are means±SE, n=0.4to 5.

BrdU-labeling of hepatocytes was examined in acetaminophen-challenged mice that received either 0.8 mg of IgG or anti-MIP-2 antibody. In mice that received IgG alone, BrdU-labeled nuclei were evident in the liver at 48 h after the immunoglobulin administration. In contrast, MIP-2 immunoneutralization significantly reduced the quantity of BrdU-labeled hepatocytes by approximately five-fold (p=0.04) at 48 h after anti-MIP-2 antibody administration (FIG. 19).

Cyclin D1 levels were also determined using Western blot analysis of nuclear extracts from acetaminophen-challenged mice that received either 0.8 mg of IgG, anti-MIP-2 antibody or anti-CXCR2 antibody. All three groups were examined at 24 h after IgG or antibody treatment in order to ensure that sufficient numbers of mice were alive in the anti-CXCR2 antibody group. The intensity of the 34-kDa band denoting cyclin D1 protein expression was dramatically reduced in both antibody treatment groups compared with the IgG control group.

Since hepatocyte proliferation was impaired in acetaminophen-challenged mice that received either anti-MIP-2 antibody or anti-CXCR2 antibody, nuclear levels of transcription factors necessary for hepatocyte proliferation were examined. Liver samples from acetaminophen-challenged mice that received IgG alone, exhibited strong nuclear expression of both LAP isoforms of C/EBP-β, whereas liver samples from the other two groups of mice exhibited dramatically less expression of both the 38- and 35-kd LAP isoforms of C/EBP-β. Similarly, hepatic STAT3 expression was markedly lower in nuclear extracts from acetaminophen-challenged mice that received anti-MIP-2 or anti-CXCR2 antibody treatment. STAT3 protein levels in the IgG-treated group were greater than the STAT-3 levels in either of the two antibody treatment groups. Thus, these data show that the lack of endogenous MIP-2 or CXCR2 severely compromise the liver regenerative process that follows hepatic exposure to acetaminophen.

EXAMPLE V

Therapeutic Effects of IP-10 In Vivo

A. Materials and Methods
1. Acetaminophen-Induced Hepatic Injury

Acetaminophen challenge was performed as described above in Example IV.

2. Protocols

Fasted mice received either PBS (0.5 ml) as control or 1 µg IP-10 (Peprotech) dissolved in 0.5 ml of PBS via an intravenous (i.v.) injection at 10 h after the acetaminophen challenge. It is important to note that the exogenous IP-10 in this study is administered at the level of 1 µg, in contrast to the 2 µg of IP-10 used in Example II. Liver and serum samples were removed from each mouse at 4, 8, 26, 34, 40, and 48 h after PBS or IP-10 administration.

3. Protein Detection

Murine IP-10 and MIP-2 was quantified using a double ligand method. Briefly, flat-bottomed 96-well microtiter plates (Nunc Immuno-Plate I 96-F, Denmark) were coated with 50 µl/well of anti-mouse cytokine antibody (1 µg/ml in 0.6 M NaCl, 0.26 M $H_3BO_4$, and 0.08 M NaOH, pH 9.6) for 16 hrs at 4° C. and then washed with wash buffer (PBS, pH 7.5, 0.05% Tween-20). Nonspecific binding sites in each plate were blocked with 2% BSA in PBS and incubated for 90 min at 37° C. Plates were rinsed four times with wash buffer and diluted (neat and 1:10) serum (50 µl) in duplicate were added to each plate, and incubated for 1 hr at 37° C.

Plates were washed four times, followed by the addition of 50 µl/well biotinylated rabbit antibodies against the specific cytokines (3.5 µg/ml in PBS, pH 7.5, 0.05% Tween-20, and 2% FCS), and plates incubated for 30 min at 37° C. After washing, streptavidin-peroxidase conjugate (Bio-Rad Laboratories, Richmond, Calif.) was added, and the plates incubated for 30 min at 37° C. After washing again, chromogen substrate (Bio-Rad Laboratories, Richmond, Calif.) was added. The plates were incubated at room temperature to the desired extinction, and the reaction terminated with 50 µl/well of 3M $H_2SO_4$ solution. Plates were read at 490 nm in an ELISA reader. Standards were one-half log dilutions of LPS-free recombinant murine cytokines (R&D Systems or Preprotech) from 1 pg/ml to 100 ng/ml. This ELISA method consistently detected murine cytokine concentrations above 25 pg/ml, and ELISA specificity was confirmed for each cytokine and chemokine measured.

Serum levels of Alanine Aminotransferase (ALT) were determined at 8 h after mice were treated with IP-10 by Clinical Pathology at the University of Michigan Medical School (Ann Arbor, Mich.) using standardized techniques.

4. Reverse Transcription Polymerase Chain Reaction mRNA expression in the liver of acetaminophen challenged mice was examined using reverse transcription polymerase chain reaction (RT-PCR™). Briefly, total RNA was isolated from liver homogenates and 5 µg of total RNA was reverse transcribed to yield cDNA using techniques previously described in detail (Hogaboam et al., 1998). PCR™ samples were initially incubated for 94° C. for 5 min and then cycled 30 times through denaturation at 95° C. for 30 seconds, annealing at 55° C. for 45 seconds, and extension at 72° C. for 75 seconds. PCR™ products were then separated on 2% agarose gels containing 0.3% ethidium bromide, and the bands corresponding to the intended products were photographed under ultraviolet illumination.

5. Histology and Immunohistochemistry

A portion of resected liver from each mouse was immediately fixed in 4% paraformaldehyde for a minimum of 12 h. Fixed liver samples were subsequently processed, embedded in paraffin, thin-sectioned, and placed on L-lysine-coated slides. Hematoxylin and eosin (H&E) staining was used to reveal morphometric differences between each group of mice. Additional slides containing unstained liver sections were used for immunohistochemical analysis.

To reveal the presence of CXCR2 in liver sections, other slides were deparaffinized, microwaved for approximately 20 min in 10 mM citric acid buffer, and then allowed to cool to room temperature. Slide-mounted liver sections were blocked using normal goat serum (blocking solution) for 1 h. Tissue sections were treated with purified polyclonal anti-mouse CXCR2 antibody or rabbit IgG for control. All were diluted at 1:25 with TBS containing blocking solution (1:100) and incubated overnight at 4° C. After incubation, slides were washed twice for 5 min in TBS. A 1:35 dilution of biotinylated goat anti-rabbit antibody (BioGenex, San Ramon, Calif.) was placed on the slides for 2 h at 37° C. in a humidified chamber. Slides were again washed twice in TBS, and incubated with a 1:35 dilution of streptavidin conjugated to horseradish peroxidase (BioGenex) for 45 min. Following two washes in TBS with 50 mM levamisole, fast red chromogen (BioGenex) was placed on each slide, and staining was visualized at low power until color development was complete. The staining reaction was terminated in sterile water, and each slide was counterstained with Mayer's hematoxylin (0.1%; Sigma).

6. Cytoplasmic Extractions

Preparation of cytoplasmic extracts from liver was conducted by rapidly homogenizing liver samples in PBS containing Complete$^{TB}$ protease inhibitor (10 mg/ml; Boehringer Mannheim) on ice and washed with fresh PBS. Homogenates were then suspended in Buffer A (10 mM Hepes, 10 mM KCl, 0.5 mM DTT, 1% NP-40) for 10 min and centrifuged for 10 min at 14,000×g and the supernatant containing cytoplasmic components was removed.

7. Western Blot Analysis

After cytoplasmic protein levels were determined using a Bradford assay (Bio-Rad), 50 µg of liver cytoplasmic extracts were electrophoresed on a 12% polyacrylamide gel and then transferred to a PVDF membrane (Bio-Rad). Equal protein loading was confirmed by Coomassie blue staining of the gel after transfer. PVDF membranes were blocked for 1 h at room temperature in 5% dry milk. CXCR2 antibodies were diluted to 1:500 and incubated with PVDF membranes overnight at 4° C. Horseradish peroxidase-linked secondary antibody (Pierce) were then added at a 1:3,000 dilution for 2 h at room temperature, and protein bands were visualized by chemiluminescence (Bio-Rad).

8. Statistical Analysis

Results are expressed as means±standard error of the mean (SEM) of 5–10 mice per group at each time point after treatment. All statistical calculations were performed using GraphPad Prism 2.0 computer software (San Diego, Calif.); $P \leq 0.05$ was considered statistically significant.

B. Results

1. IP-10 is Elevated During Acetaminophen-induced Liver Toxicity

Figure 20:
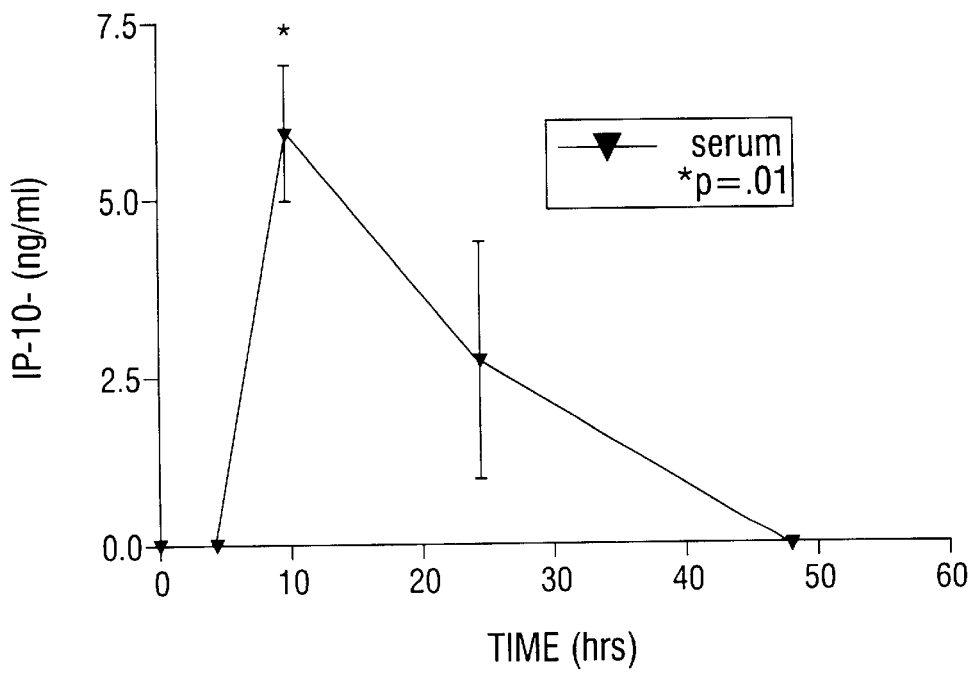
FIG. 20. IP-10 levels are dramatically elevated 8 hours after acetaminophen challenge in fasted mice. Prior to acetaminophen challenge (time 0) and 4 h after a sub-lethal acetaminophen dose (400 mg/kg), there are no detectable levels of IP-10 in the serum. In contrast, by 8 h after acetaminophen, IP-10 levels are dramatically elevated. These elevated levels are not sustained throughout recovery from acetaminophen and IP-10 levels begin to fall by 24 h after challenge. Data shown are mean±SEM of 5–8 mice per group at each time point before (time 0) and after acetaminophen challenge. * indicates P≦0.05 compared with time 0.

To understand the role of the non-ELR-CXC chemokines, IP-10 levels were examined in the serum of acetaminophen-challenged mice prior to challenge, and at 4, 8, 24, and 48 hours after challenge. As shown in FIG. 20, immediately prior (i.e. 0 h) to an i.p. challenge of 400 mg/kg acetaminophen and 4 h after this challenge there were no detectable levels of IP-10 in the serum. In contrast, 8 h after acetaminophen-challenge, levels of IP-10 were dramatically increased (p=0.01). By 24 h, the levels of IP-10 were lower so that by 48 h IP-10 was not detectable in the serum.

Figure 21:
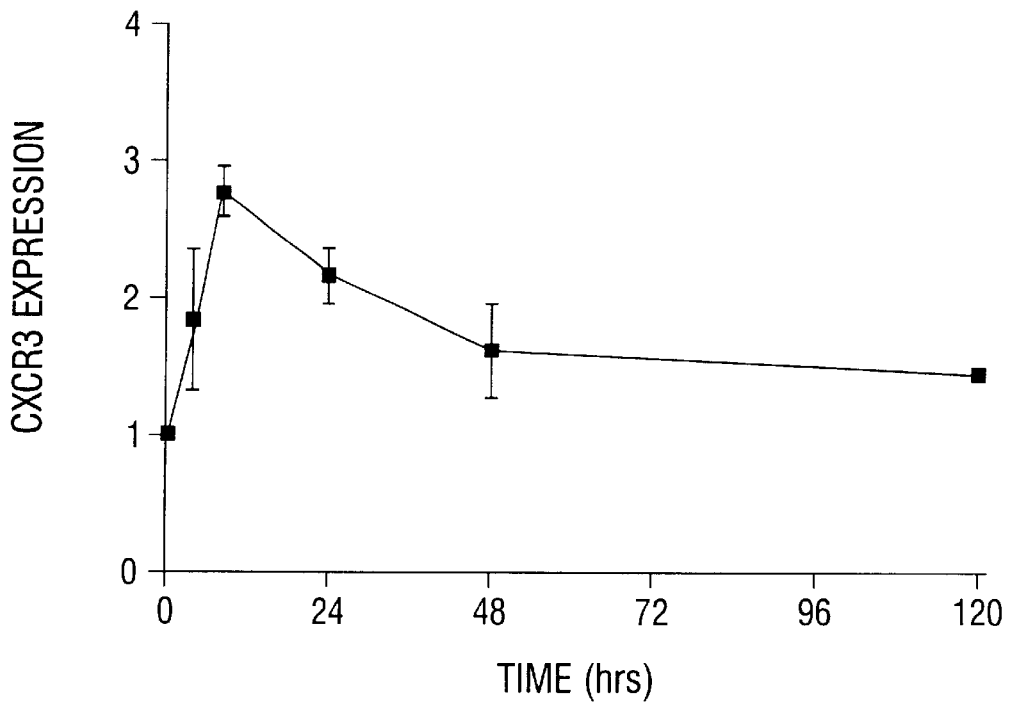
FIG. 21. CXCR3 expression in liver homogenates after acetaminophen-challenge (400 mg/kg) in fasted CD-1 mice. RT-PCR™ analysis was used to show CXCR3 and cyclophilin (housekeeping gene) mRNA expression in liver homogenates prior to and after acetaminophen-challenge. Bands were examined by densitometric analysis and the ratio of CXCR3 to cyclophilin after acetaminophen was compared to the baseline levels (time 0).

Since the levels of IP-10 were regulated following acetaminophen-induced liver injury, changes in CXCR3, the receptor for IP-10, was next examined. RT-PCRTM analysis revealed that CXCR3 mRNA was expressed in liver homogenates prior to acetaminophen-challenge and increased following the challenge. Not only was the receptor present after acetaminophen challenge, CXCR3 expression was dramatically upregulated (FIG. 21). For instance, 4 h following acetaminophen-challenge, there was almost twice as much CXCR3 mRNA expressed compared to prior to acetaminophen as determined by densitometry; and at 8 h following the challenge, there was almost three times more mRNA expressed. Thus, IP-10 and CXCR3 were both upregulated following a sub-lethal acetaminophen-challenge in vivo, which correlates to the time when the ASTs and ALTs, markers of liver damage, are at their peak levels.

2. IP-10 Dramatically Decreases Liver Injury After Acetaminophen-challenge

A 10 h delayed treatment with ELR-CXC chemokines has a dramatic therapeutic effect at a time when the standard of care, N-acetyl-cysteine, is no longer effective (contrast present invention with De Groote and Steenbergen, 1995). The inventors postulated that a delayed treatment with IP-10 would have a beneficial effect on liver injury after an acetaminophen-challenge.

When animals were treated with 1 µg IP-10 or control (PBS) 10 h after a 400 mg/kg dose of acetaminophen, IP-10 dramatically decreased hepatic injury 2 days after challenge (contrast to the 2 µg of IP-10 used in Example II). When control animals were treated with PBS, there is dramatic centrilobular hepatocyte necrosis and hemorrhagic injury. In contrast, when animals were treated with an effective amount of IP-10, there is little evidence of hepatocyte injury. It will be understood that IP-10 should not be administered at too high a level, when the therapeutic benefits can be masked.

Figure 22:
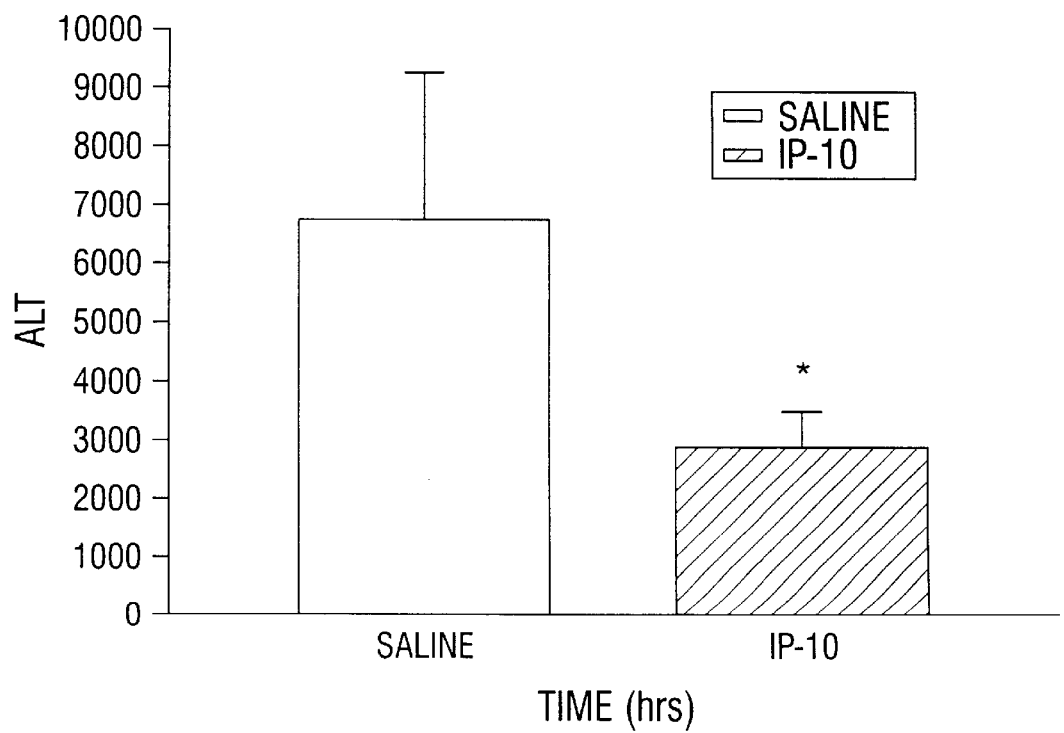
FIG. 22. Serum alanine aminotransferase (ALT) activity in fasted mice fasted following a 10 h post-treatment of IP-10 or saline in mice that had been challenged with a dose of 400 mg/kg acetaminophen. Blood was removed from each mouse 8 h after treatment for ALT determination. IP-10 post-treatment dramatically decreased the levels of detectable ALT in the serum. Data shown are mean±SEM of 5–6 mice per group. * indicates P≦0.05 compared with saline.

Acute hepatocellular injury results in elevated levels of ALTs. As shown in FIG. 22, IP-10 significantly decreased liver injury at 8 hours after administration by approximately three-fold ($p=0.0078$). Taken together these data demonstrate that IP-10 has a dramatic therapeutic effect 10 h after an acetaminophen challenge. Subsequent studies were designed to address the mechanisms for this therapeutic application.

3. MIP-2 and CXCR2 are Upregulated Following IP-10 Treatment

Figure 23:
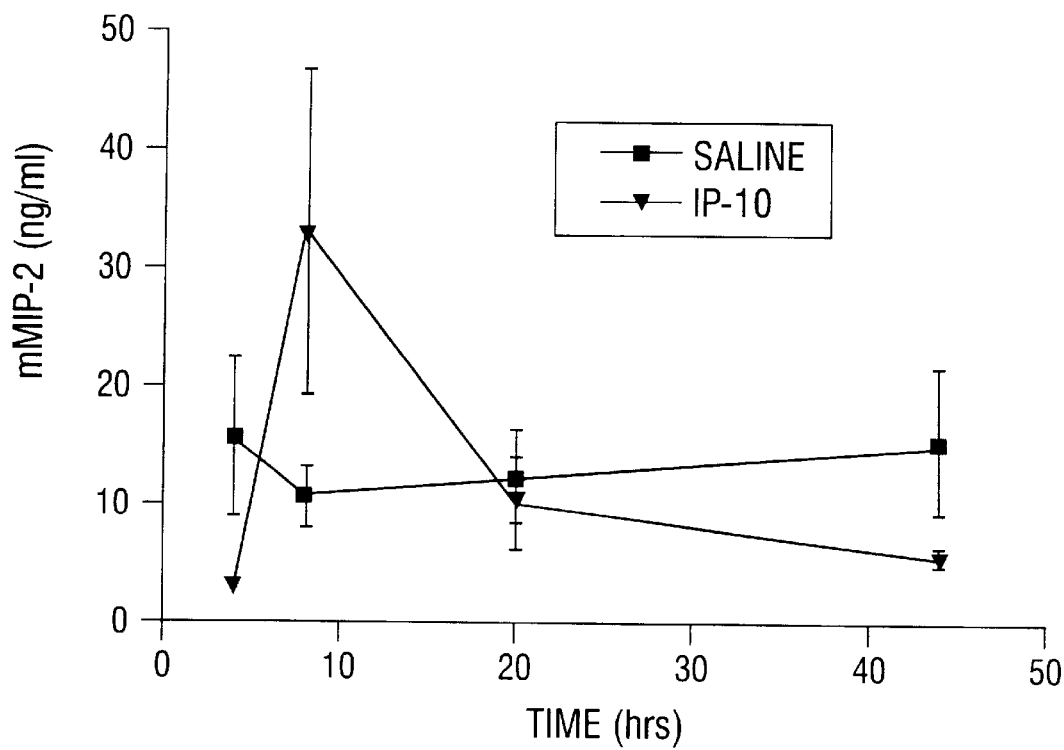
FIG. 23. Immunoreactive levels of MIP-2 levels were significantly elevated by 8 h after IP-10 post-treatment. Animals were post-treated with IP-10 10 h following a sub-lethal dose of acetaminophen (400 mg/kg). By 8 h after IP-10 treatment, MIP-2 levels are dramatically elevated as compared to saline-treated animals. Data shown are mean±SEM of 5–8 mice per group at each time point. * indicates P≦0.05 compared with saline.

The previous studies show that MIP-2 and its receptor CXCR2 have a tremendous therapeutic effect in acute liver injury due to their effect on liver regeneration (Example V). To assess whether IP-10 exerts its therapeutic effect via MIP-2 and/or the CXCR2 receptor, the expression of MIP-2 and CXCR2 was examined. At 8 h post IP-10 treatment, MIP-2 levels are significantly elevated ($p=0.02$) to almost three times the levels seen in control animals (FIG. 23), and then subsequently decline to control levels.

Not only are there changes in MIP-2 expression, but CXCR2 is dramatically upregulated on hepatocytes within the acetaminophen-challenged liver. IP-10 post-treatment dramatically increased the expression of CXCR2 protein, as detected by immunohistochemistry. Low CXCR2 expression on hepatocytes was observed after an i.p. challenge with 400 mg/kg of acetaminophen. These control mice received 0.5 ml of PBS by i.v. injection at 10 h after acetaminophen challenge. In contrast, mice that received 1 µg of IP-10, had quite strong expression of CXCR2 protein on hepatocytes within the liver 24 h after treatment. Negative controls validate these results.

To understand if this elevated expression of CXCR2 on hepatocytes was a temporal phenomenon, mice were examined for CXCR2 protein expression by Western blot analysis 4, 26, 34, 40, and 48 h after IP-10 or saline treatment in acetaminophen-challenged mice. Although there was similar expression in both groups of mice at 4 h after treatment, by 26 h there was a dramatic divergence in CXCR2 expression. Mice post-treated with IP-10 expressed a high level of CXCR2 protein as indicated by the 42 and 84-kDal bands at all subsequent time points examined. In contrast, mice post-treated with saline had no detectable levels of CXCR2 protein expressed in liver homogenates. Thus, IP-10 treatment increased the level of MIP-2 systemically and CXCR2 in the liver, which is believed to be the mechanism for the restoration of liver integrity that IP-10 imparts.

EXAMPLE VI

Stem Cell Factor (SCF) Attenuates Liver Damage and Promotes Regeneration

A. Introduction

Liver damage can be induced by infectious, pharmacological, environmental, or inflammatory/immune responses. Possibly one of the most common insults to the liver is accidental or purposeful acetaminophen poisoning, which appears to have a direct toxicity to the hepatocytes (Williams; Prescott, 1983). The subsequent reaction is characterized by a massive damage of the liver, followed by intense inflammation and finally regeneration of the damaged tissue (Prescott and Critchley, 1983). This rapid progression of events takes only days to come to culmination and the health of the patient depends upon efficient regeneration of the damaged hepatic tissue (Chanda and Mehendale, 1996; Bisgaard and Thorgeirsson, 1996).

Several factors and cytokines may participate in the regeneration of the liver tissue, including HGF, bFGF, as well as several other growth factors which appear to directly influence the neo-proliferation and differentiation of hepatocytes (Jiang and Hiscox, 1997; Kay and Fausto, 1997). In addition, the liver also appears to constitutively contain other factors, such as IL-10, which may attenuate damage induced by inflammatory responses.

Nonetheless, further mediators of repair are always welcome in expanding the therapeutic options available to a clinician. These aspects of the present invention are based upon the discovery that stem cell factor (SCF) has an important role in liver regeneration after injury.

Stem cell factor (SCF) is predominantly a hematopoietic factor that induces leukocyte maturation and differentiation (Galli et al., 1994). However, recent evidence would suggest that its production during disease may serve other important roles in structural tissue repair and protection (Wershil et al., 1992; Costa et al., 1996). Not only is SCF a growth factor for melanocytes found in the skin, it appears to be associated with other cell populations, in particular hepatocytes (Fujio et al., 1994). In addition, SCF and its receptor, c-kit, have been shown to be expressed on numerous types of tumor cells, including neuroblastomas, small cell lung adenocarcinoma, and hepatomas (Ricotti et al., 1998; Papadimitriou et al., 1995; Beck et al., 1997; Bar-Eli, 1997; Turner et al., 1992). Finally, SCF has been shown to attenuate radiation-induced injury in several cell populations, indicating that it may have an overall protective effect for cells (Zsebo et al., 1992; Leigh et al., 1995; Liebmann et al., 1994).

Previous studies have indicated the presence of SCF within the liver, which is localized around the ductal epithelial cells (Omori et al., 1997), a probable focal point of hepatic regeneration (Alison et al., 1996). Altogether, the previous studies indicate that SCF has diverse roles depending upon the cell population that is producing it.

In the present invention, a role for SCF in liver regeneration is defined utilizing a murine model of acetaminophen-induced liver toxicity. The data indicates that a significant amount of SCF can be found constitutively in the livers of normal mice and subsequently is significantly decreased during the injury, corresponding to hepatocyte damage. As the liver begins to recover and regenerate, SCF levels rise and correlate to the regeneration event. Neutralization of SCF during the acetaminophen response significantly attenuates the regeneration, leaving more liver damage. Likewise, when exogenous SCF was given to the acetaminophen treated animals lethality was abrogated. Overall, these studies indicate a significant role for SCF in liver function and protection from injury.

B. Materials and Methods

1. Animals

Six wk old female CBA/J mice (Jackson Laboratory, Bar Harbor, Me.) were fasted, but with free access to water, for 8 h prior to intraperitoneal (I.P.) injection of acetaminophen (Sigma) at 200 or 300 mg/kg, dissolved in normal saline. After injection, the animals were allowed free access to food. Mice were euthanized and liver was taken from the mice at various time points after acetaminophen injection into the mice.

2. Production of Anti-SCF Antibodies

Rabbit anti-murine SCF antibodies were prepared by multiple-site immunization of New Zealand White rabbits with recombinant murine SCF (Genzyme) in CFA. Polyclonal antibodies were titered by direct ELISA and specifically verified by the failure to crossreact to mIL-3, mIL-1α, mTNF, mMIP-1α, IL-6, mJE, mMIP-1β, hMCP-1, hIL-8, hRANTES, hMIP-1α, hTNF, and hMIP-1β. The IgG portion of the serum was purified over a protein A column and used in a sandwich ELISA and for immunohistochemical staining.

3. SCF ELISA

SCF was quantitated by ELISA using a modification of a double ligand method (Lukacs et al., 1996; incorporated herein by reference). Briefly, flat-bottomed 96 well microtiter plates (Nunc Immuno-Plate I 96-F, Denmark, Netherlands) were coated with 50 µl/well of rat anti-SCF monoclonal antibody (1 ng/µl in 0.6 M NaCl, 0.26 M H3BO$_4$, and 0.08 N NaOH, pH 9.6) for 16 h at 4° C. and then washed with phosphate buffered saline (PBS), pH 7.5, 0.05% Tween-20 (wash buffer). Nonspecific binding sites were blocked with 2% BSA in PBS and incubated for 90 min at 37° C. Plates were rinsed four times with wash buffer and diluted (1:2 and 1:10) cell-free supernatants in duplicate were added, followed by incubation for 1 h at 37° C.

Plates were washed four times, followed by the addition of 50 µl/well biotinylated rabbit anti-SCF antibody (3.5 ng/µl in PBS, pH 7.5, 0.05% Tween-20, and 2% FCS), and plates incubated for 30 min at 37° C. Plates were washed four times, streptavidin-peroxidase conjugate (Bio-Rad Laboratories, Richmond, Calif.) added, and the plates incubated for 30 min at 37° C. Plates were again washed four times and chromogen substrate (Bio-Rad Laboratories, Richmond, Calif.) added.

The plates were then incubated at room temperature to the desired extinction, and the reaction terminated with 50 µl/well of 3M H$_2$SO$_4$ solution. Plates were read at 490 nm in an ELISA reader. Standards were ½ log dilutions of recombinant SCF from 10 pg/ml to 100 ng/ml. This ELISA method consistently detected SCF concentrations above 250 pg/ml. The SCF antibody ELISA did not cross-react with mIL-3, mIL-1α, mTNF, mMIP-1α, IL-6, mJE, mMIP-1β, HMCP-1, hIL-8, hRANTES, hMIP-1α, hTNF, and hMIP-1β.

4. In Vivo Neutralization of SCF

Neutralization of SCF was carried out using a polyclonal rabbit anti-murine SCF antibody. The protein A column purified anti-SCF or control antibody was intraperitoneally 1 h prior to acetaminophen treatment. Likewise, paraffin embedded liver sections were stained and the damage was quantitated at the various time points post-challenge.

5. Immunohistochemical Localization of SCF in the Liver

Paraffin embedded tissue sections mounted on poly-L-lysine slides were deparaffinized with xylene followed by stepwise rehydration in 100%, 95%, 70%, and 50% ethanol followed by 10 min incubation in PBS. All tissue sections were blocked with normal goat serum for 30 min. The sections were covered with the rabbit anti-murine SCF serum diluted in PBS (1:250) for 30 min at 37° C. After rinsing 3× with PBS the sections were overlaid for 20 min with biotinylated goat anti-rabbit IgG (Biogenex, San Ramon, Calif. supersensitive reagent 1:30). After rinsing 3 times with PBS the liver sections were incubated for 20 min with streptavidin-peroxidase (Biogenex, 1:1000) at 37° C. The slides were rinsed with PBS and overlaid with AEC solution until color development was observed (10–20 min). Sections were rinsed and counterstained with Mayer's hemotoxylin.

6. Assessment of Hepatic Repair and Injury

Hepatic damage was measured using an AXIO-HOME microscope by 2 independent investigators. Sections of liver tissue (2 from each animal) were stained with hematoxylin and eosin and the area of hepatic damage was outlined and expressed as a % of total liver area examined.

7. Statistical Analysis

Statistical significance was determined by analysis of variance and Student's t-test as appropriate, with $P \leq 0.05$ considered significant.

C. Results

1. Acetaminophen-induced Liver Damage Correlates with Decreased SCF Levels

To determine the level of acetaminophen that was necessary to induce liver damage, a dose response was performed. In these studies, normal CBA/J mice were fasted for 8 h and subsequently given an intraperitoneal injection of acetaminophen dissolved in PBS or PBS alone for control. Mouse survival was followed for 4 days when the study was terminated. 20 mice/group were used in 2 separate studies.

The preliminary studies indicated that a sublethal dose of 200 mg/kg could induce significant liver pathology with no lethality, while 300 mg/kg induced catastrophic liver damage and was nearly 100% lethal by 48 h.

SCF levels were then measured in liver tissue in mice treated with lethal (300 mg/kg) or sub-lethal (200 mg/kg) doses of acetaminophen. A portion of the liver from euthanized mice was taken and weighed immediately after extraction at various time points after acetaminophen administration. The liver tissue was ground in PBS with 0.1% Triton X-100 containing anti-proteases and the cell-free supernatant was assayed in a SCF-specific ELISA. Data was obtained from at least 6 mice/time point; the mean±SE was calculated, with P values of=0.05 being determined.

In such studies, in animals treated with either low or high dose of acetaminophen, a significant decrease in SCF levels was observed, which correlated with hepatic damage. In the low dose treated animals, which recover from the injury, the SCF levels begin to rebound by day 2 and continue to rise at day 4 and by to day 6 when livers appeared to be normal histologically the levels of SCF were similar to control livers.

In the high dose acetaminophen treatment, the SCF levels in the liver demonstrated a significant decrease with no recovery, correlating with the lack of liver regeneration and death. In addition, the serum levels of SCF showed an increase in SCF at 6 to 12 h post-acetaminophen, suggesting a release from the damaged liver into circulation. Altogether, these data indicate that SCF levels are produced constitutively in the liver and subsequently altered during acetaminophen poisoning, correlating directly with the health of the liver.

2. Cellular Localization and Neutralization of SCF During Acetaminophen Poisoning To determine which cells were producing SCF within the liver, immunohistochemical staining in regenerating liver samples was utilized. Tissue sections were incubated with control or anti-SCF antibody and examined for specific staining.

SCF staining was found within the bile duct epithelial cells with additional SCF staining in the nuclear area of hepatocytes. In regenerating livers from the low dose acetaminophen treated animals, SCF localization was found in areas within regenerating tissue. This pattern was consistent with previously published results on SCF staining within the liver (Rao et al., 1996; Fujio et al., 1994).

Next, in order to determine the role of SCF in acetaminophen-induced liver tissue, animals were passively immunized with anti-SCF antibody (or control serum) intraperitoneally 1 h prior to low dose acetaminophen treatment. The survival of animals was recorded for 4 days and then terminated. Livers were harvested and examined histological. % survival data was gathered from 2 separate studies with a total of 20 mice in each treatment group. It was determined that in those animals given anti-SCF, only 40% of the mice survived, compared to the control antibody treated group that had 80% of the animals survive.

Livers from the treated animals that survived were then examined histologically and the necrotic areas measured morphometrically. Sections of liver tissue (2 from each of the foregoing animals) were stained with hematoxylin and eosin and the area of hepatic damage was determined morphometrically and expressed as a % of total liver area examined. Data were analyzed from at least 8 mice/group and the means±SE were calculated.

These studies showed that the level of damage at day 4 (a time when regeneration was normally beginning in acetaminophen treated animals) demonstrated a significant increase in necrotic area in anti-SCF treated animals as compared to control serum treated animals ($P \leq 0.05$). These data suggested either increased damage or a lower level of regeneration in SCF-depleted animals. Thus, SCF appears to have a significant role in maintaining the health of the liver within this model of acetaminophen toxicity.

3. Exogenous SCF Protects Mice From a Lethal Acetaminophen Dose

In order to finally determine whether SCF has a role in protecting the animals from acetaminophen toxicity, 1 µg of recombinant murine SCF or saline was injected i.v. at the time of or within 30 min. of acetaminophen challenge. The survival of animals was recorded for 4 days and the study was terminated. % Survival data was collected from 2 separate studies with a total of 20 mice in each treatment group.

In these studies, when animals were given exogenous SCF, they were protected from a lethal dose of acetaminophen with 90% of the animals surviving, compared to only 30% of the control animals surviving in the control treated group of animals.

These data were followed by examining liver damage at 48 h post-acetaminophen treatment. Livers from animals given exogenous SCF have no evidence of damage histologically at 4 days post-lethal acetaminophen (300 mg/kg) administration. Animals were treated with 1 µg of recombinant SCF or saline within 30 min of acetaminophen administration (300 mg/kg). The survival of animals was recorded for 4 days and the study was terminated. The livers were examined histologically and demonstrated that animals treated with recombinant SCF had no necrotic areas, whereas large areas of damage could easily be found in saline-treated animals.

This demonstrates the ability of exogenous SCF to attenuate the damage of the liver. The livers from the mice given SCF appear to be normal with minimal damage, whereas the livers from control treated animals have significant necrotic areas. Overall, these data demonstrate that SCF has a significant role in altering liver damage in response to acetaminophen poisoning.

D. Discussion

The regeneration of liver tissue after damage is an area of intense investigation. It appears that multiple factors may be involved, including several cytokines and cellular interactions (Chanda and Mehendale, 1996; Bisgaard and Thorgeirsson, 1996). In this study, the inventors examined the involvement of SCF in liver damage and regeneration. Previous studies have indicated the presence of SCF in liver tissue, which was localized within the bile duct epithelial cells (Omori et al., 1997), an area of the liver that appears to be the focal point of regeneration (Alison et al., 1996).

The present studies also demonstrated immunohistochemical localization of SCF to the same areas in normal tissue as was found in the above study. In addition, these investigations indicate increased SCF staining in areas of the liver where regeneration was occurring after acetaminophen-induced damage. Interestingly, when SCF was measured from liver samples a high constitutive level was observed in normal livers, which was significantly decreased as the hepatic damage was induced with the acetaminophen treatment. The hepatic SCF levels then rose again as the tissue began to regenerate and returned to control levels at 6 days post-acetaminophen treatment, a time when the tissue appeared near normal, histologically.

Although the latter data are only correlative, the anti-SCF treatment demonstrated a significant increase in lethality to a sublethal dose of acetaminophen. In addition, there was also a higher level of tissue damage and therefore decreased tissue regeneration at day 4. These data can be interpreted several ways. First, SCF may have direct effects on hepatocyte growth and differentiation. Preliminary results indicate that SCF can directly induce hepatocyte proliferation in vitro. An alternative hypothesis may be that SCF could "protect" the liver tissue from toxic injury. This would follow the fact that SCF has been shown to attenuate radiation-induced injury in multiple cell populations (Zsebo et al., 1992; Leigh et al., 1995; Liebmann et al., 1994), an event which relies on oxidative metabolites.

The data from this study demonstrate that SCF levels actually fall during damage and do not return until regeneration has occurred. In addition, the fact that livers have high constitutive levels of SCF may suggest that its persistence within the liver may be necessary to protect cells from damage. The anti-SCF treatment may reduce that level of protection and increase the damage induced by acetaminophen treatment.

The present studies were followed by administration of exogenous SCF. The effects of the lethal dose could be almost totally abrogated by giving SCF at the time of acetaminophen poisoning, indicating a therapeutic role for SCF in liver damage.

There is a paucity of data concerning the role of SCF during disease. The extra-hematopoietic activity of SCF is only now being examined. Its importance in structural cell growth and differentiation may be most prominently exhibited when examining cancerous cell populations. Many different types of cancerous cell populations have demonstrated the presence of SCF production and c-kit expression, including neuroblastomas, melanoma, pulmonary small cell adenocarcinoma, and hepatomas (Ricotti et al., 1998; Papadimitriou et al., 1995; Beck et al., 1997; Bar-Eli, 1997; Turner et al., 1992). Again, the role for SCF in tumor cells may be two-fold, either a growth factor and/or a way to protect cells from injurious immunological/inflammatory insults. This hypothesis, although untested, would be attractive for cancerous cells as an additional mechanism for continued growth and avoidance of the immune system.

SCF is most notably known for its hematopoictic ability for growth and differentiation of bone marrow-derived cells, including erythrocytes, lymphocytes, neutrophils, as well as being absolutely required for mast cell growth, differentiation, and survival (Galli et al., 1994; Wershil et al., 1992). Interestingly, the fetal liver is a prominent site for hematopoiesis and it is reasonable that SCF would be made within these tissues (Emerson, 1990; Timens and Kamps, 1997). However, the production of constitutive levels of SCF into adulthood, a time when the hematopoietic activity of the liver is minimal, may indicate that SCF has alternative functions. As discussed earlier, SCF is now envisioned to have important roles as either a molecule that promotes cell growth and differentiation or as a factor to prevent the tissue from damage induced by pathological insults.

These data suggest that SCF is produced within the liver and has alternative functions other than just a bone marrow associated hematopoietic factor. The correlation of SCF levels with liver regeneration, and the neutralization data that indicates higher levels of damage in animals treated with SCF, indicates that SCF plays an important role in the health and regeneration of the liver during disease pathogenesis. SCF can thus be used to protect hepatocyte damage and encourage growth.

All of the compositions and methods disclosed and claimed herein can be made and executed without undue experimentation in light of the present disclosure. While the compositions and methods of this invention have been described in terms of certain preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Akerman, Cote, Yang, McClain, Nelson, Bagby, Diehl, "Antibodies to tumor necrosis factor-α inhibit liver regeneration after partial hepatectomy," Am. J. Physiol., 263:G579–G585, 1992.

Alison, Golding, and Sarraf, "Pluripotential liver stem cells: facultative stem cells located in the biliary tree," Cell Prolif., 29:373–402, 1996.

Alison, Golding, Sarraf, "Liver stem cells: when the going gets tough they get going," Int. J. Exp. Path., 78:365–381, 1997.

Alpini, Phillips, Vroman, LaRusso, "Recent advances in the isolation of liver cells," Hepatology, 20:494–514, 1994.

Anisowicz et al., "Functional diversity of gro gene expression in human fibroblasts and mammary epithelial cells," Proc. Natl. Acad. Sci. USA, 85:9645–49, 1988.

Atillasoy and Berk, "Fulminant hepatic failure: pathophysiology, treatment, and survival," Annu. Rev. Med., 46:181–191, 1995.

Baggiolini, Walz, Kunkel, "Neutrophil-activating peptide-1/interleukin-8, a novel cytokine that activates neutrophils," J. Clin. Invest, 84:1045–49, 1989.

Bao, Zhang, Kuo, "Adenoviral delivery of recombinant DNA into transgenic mice bearing hepatocellular carcinomas," Hum. Gene Ther., 7(3):355–365, 1996.

Bar-Eli, "Molecular mechanisms of melanoma metastasis," J. Cell Physiol., 173:275–278, 1997.

Bautista, "Chronic alcohol intoxication induces hepatic injury through enhanced macrophage inflammatory protein-2 production and intercellular adhesion molecule-1 expression in the liver," Hepatology, 25(2):335–342, 1997.

Beck, Gross, Brognara, and Perruisseau, "Expression of stem cell factor and its receptor by human neuroblastoma cells and tumors," Blood, 86:3132–3138, 1995.

Bell et al., "Recombinant human adenovirus with rat MIP-2 gene insertion causes prolonged PMN recruitment to the murine brain," Eur. J. Neurosci., 8(9):1803–1811, 1996.

Bernal, Wendon, Rela, Heaton, Williams, "Use and outcome of liver transplantation in acetaminophen-induced acute liver failure," Hepatology, 27:1050–1055, 1998.

Berry and Friend, "High-yield preparation of isolated rat liver parenchymal cells. A biochemical and fine structural study," J. Cell. Bio., 43:506–520, 1969.

Beyer and Stanley, "Tumor necrosis factor-α increases hepatic DNA and RNA and hepatocyte mitosis," Biochem. Int., 22:405–410, 1990.

Bisgaard and Thorgeirsson, "Hepatic regeneration: The role of regeneration in pathogenesis of chronic liver diseases," Clin. Lab. Med., 16:325–339, 1996.

Blazka et al., "Role of proinflammatory cytokines in acetaminophen hepatotoxicity," Toxicol Appl. Pharmacol., 133(1):43–52, 1995.

Bruccoleri et al., "Induction of early-immediate genes by tumor necrosis factor alpha contribute to liver repair following chemical-induced hepatotoxicity," Hepatology, 25:133–141, 1997.

Burgess-Beusse, Timchenko, Darlington, "CCAAT/Enhancer binding protein α (C/EBPα) is an important mediator of mouse C/EBPβ protein isoform production," Hepatology, 29:597–601, 1999.

Cacalano, Lee, Kikly, Ryan, Pitts-Meek, Hulgren, Wood, Moore, "Neutrophil and B cell expansion in mice that lack the murine IL-8 receptor homolog," Science, 265:682–684, 1994.

Casey and Tracey, "N-acetylcysteine (NAC)—a safe antidote in paracetamol poisoning?," Ir. Med. J., 90:38, 1997.

Casley et al., "Differences in caffeine 3-demethylation activity among inbred mouse strains: a comparison of hepatic Cyp1a2 gene expression between two inbred strains," *Fundam. Appl. Toxicol.*, 40(2):228–237, 1997.

Castell et al., "Adenovirus-mediated gene transfer into human hepatocytes: analysis of the biochemical functionality of transduced cells," *Gene Ther.*, 4(5):455–464, 1997.

Chanda and Mehendale, "Hepatic cell division and tissue repair: a key to survival after liver injury," *Mol. Med. Today*, 2:82–89, 1996.

Chanda et al., "Stimulated hepatic tissue repair underlies heteroprotection by thioacetamide against acetaminophen-induced lethality," *Hepatology*, 21(2):477–486, 1995.

Chang et al., *J. Biol. Chem.*, 269(41):25277–82, 1994.

Chuntharapai and Kim, "Regulation of the expression of the IL-8 receptor A/B by IL-8: possible functions of each receptor," *J. Immunol.*, 155:2587–2594, 1995.

Clark-Lewis, Dewald, Geiser, Moser, Baggiolini, "Platelet factor-4 binds to interleukin-8 receptors and activates neutrophils when its N-terminus is modified with Glu-Leu-Arg," *Proc. Natl. Acad Sci. USA*, 90:3574–3577, 1993.

Clark-Lewis, Kim, Rajarathnam, Gong, Dewald, Moser, Baggiolini, Sykes, "Structure-activity relationships of chemokines," *J. Leuk. Biol.*, 57:703–711, 1995.

Colletti, Remick, Burtch, Kunkel, Strieter, Campbell Jr., "Role of tumor necrosis factor-α in the pathophysiologic alterations after hepatic ischemia/reperfusion injury in the rat," *J. Clin. Invest.*, 85:1936–1943, 1990a.

Colletti, Burtch, Remick, Kunkel, Strieter, Guice, Oldham, Campbell Jr., "The production of tumor necrosis factor-α and the development of a pulmonary capillary injury following hepatic ischemia/reperfusion," *Transplantation*, 49:268–272, 1990b.

Colletti, Kunkel, Burdick, Walz, Strieter, "TNF triggers the release of ENA-78 which mediates liver injury following hepatic ischemia-reperfusion (I/R)," *FASEB J.*, 8(5):A663, #3845, 1994.

Colletti, Kunkel, Walz, Burdick, Kunkel, Wilke, Strieter, "Chemokine expression during hepatic ischemia/reperfusion-induced lung injury in the rat. The role of epithelial neutrophil activating protein," *J. Clin. Invest.*, 95(1):134–141, 1995.

Colletti, Kunkel, Walz, Burdick, Kunkel, Wilke, Strieter, "The role of cytokine networks in the local liver injury following hepatic ischemia/reperfusion in the rat," *Hepatology*, 23:506–514, 1996a.

Colletti, Kunkel, Green, Burdick, Strieter, "Hepatic inflammation following 70% hepatectomy may be related to up-regulation of epithelial neutrophil activating protein-78," *Shock*, 6:397–402, 1996b.

Colletti, Kunkel, Green, Burdick, Strieter, "Removal of the ischemic lobe following hepatic ischemia/reperfusion does not eliminate the pathophysiologic changes associated with hepatic ischemia/reperfusion," *Shock*, 5:371–377, 1996c.

Colletti, Green, Burdick, Kunkel, Strieter, "Proliferative effects of CXC chemokines in rat hepatocytes in vitro and in vivo," *Shock*, 10:248–257, 1998.

Colletti, Green, Burdick, Strieter, "The ratio of ELR+ to ELR– CXC chemokines affects the lung and liver injury following hepatic Ischemia/reperfusion in the Rat [In Process Citation]," *Hepatology*, 31:435–445, 2000.

Corbett et al., *Biochem. Biophys. Res. Comm.*, 205(1):612–17, 1994.

Costa, Demetri, Harrist, Dvorak, Hayes, Merica, Gringeri, Schwartz, and Galli, "Recombinant human stem cell factor (kit ligand) promotes human mast cell and melanocyte hyperplasia and functional activation in vivo," *J. Exp. Med.*, 183:2681–2686, 1996.

Cressman, Diamond, Taub, "Rapid activation of the Stat3 transcription complex in liver regeneration," *Hepatology*, 21:1443–1449, 1995.

Cressman, Greenbaum, DeAngelis, Ciliberto, Furth, Poli, Taub, "Liver failure and defective hepatocyte regeneration in interleukin-6-deficient mice," *Science*, 274:1379–1383, 1996.

Davern and Scharschmidt, "Gene therapy for liver disease," *Dig. Dis.*, 16:23–37, 1998.

De Groote and Van Steenbergen, "Paracetamol intoxication and N-acetyl-cysteine treatment," *Acta. Gastroenterol. Belg.*, 58:326–334, 1995.

Delanty and Fitzgerald, "Paracetamol poisoning: the action line and the timing of acetylcysteine therapy," *Ir. Med. J.*, 89:156, 158, 1996.

Descombes, Chojkier, Lichtsteiner, Schibler, "LAP, A novel member of the C/EBP gene family, encodes a liver-enriched transcriptional activator protein," *Genes Dev.*, 4:1541–1551, 1990.

Diehl, Yin, Fleckenstein, Yang, Lin, Brenner, Westwick, Bagby, Nelson, "Tumor necrosis factor-A induces C-Jun during the regenerative response to liver injury," *Am. J. Physio.*, 267:G552–G561, 1994.

Diehl, Yang, Yin, Lin, Nelson, Bagby, "Tumor necrosis factor-α modulates CCAAT/enhancer binding proteins-DNA binding activities and promotes hepatocyte-specific gene expression during liver regeneration," *Hepatology*, 22:252–261, 1995.

Diehl and Rai, "Review: regulation of liver regeneration by pro-inflammatory cytokines," *J. Gastroent. Hepatol.*, 11:466–470, 1996a.

Diehl, John, Yang, Lin, Yin, Matelis, Lawrence, "Adenovirus-mediated transfer of CCAAT/Enhancer-binding protein-α identifies a dominant antiproliferative role for this isoform in hepatocytes," *J. Biol. Chem.*, 271:7343–7350, 1996b.

Diehl, "Roles of CCAAT/Enhancer-binding proteins in regulation of liver regenerative growth," *J. Biol. Chem.*, 273:30843–30846, 1998.

Diez-Ruiz, Tilz, Gutierrez-Gea, Gil-Extremera, Murr, Wachter, Fuchs "Neopterin and soluble tumor necrosis factor receptor type 1 in alcohol-induced cirrhosis," *Hepatology*, 21:976–978, 1995.

Driscoll, Hassenbein, Howard, Isfort, Cody, Tindal, Suchanek, Carter, "Cloning, expression, and functional characterization of rat MIP-2: a neutrophil chemoattractant and epithelial cell mitogen," *J. Leuk. Biol.*, 58:359–364, 1995.

Duval, Howard, McCalden, Billings, "The determination of myeloperoxidase activity in liver," *Life Sciences*, 47:PL145–PL150, 1990.

Emerson, "The regulation of hematopoiesis in the fetal liver," *Prog. Clin. Biol. Res.*, 352:21–28, 1990.

Evanoff, Burdick, Moore, Kunkel, Strieter, "A sensitive ELISA for the detection of human monocyte chemoattractant protein-1 (MCP-1)," *Immunol. Invest.*, 21:39–49, 1992.

Fahey et al., "Cytokine production in a model of wound healing: the appearance of MIP-1, MIP-2, cachectin/TNF, and IL-1," *Cytokine*, 2:92–99, 1990.

Farrell, "Drug-induced hepatic injury," *J. Gastroenterol. Hepatol.*, 12(9–10):S242–S250, 1997.

Fausto, Laird, Webber, "Liver regeneration. 2. Role of growth factors and cytokines in hepatic regeneration," *FASEB. J.*, 9:1527–1536, 1995.

Fausto, Laird, Webber, "Role of growth factors and cytokines in hepatic regeneration," *FASEB J.*, 9:1527–1536, 1996.

Feingold, Soued, Grunfeld, "Tumor necrosis factor stimulates DNA synthesis in the liver of intact rats," *Biochem. Biophys. Res. Comm.*, 153:576–582, 1988.

Foley et al., "Adenoviral gene transfer of macrophage inflammatory protein-2 in rat lung," *Am. J. Pathol.*, 149 (4):1395–1403, 1996.

Frevert et al., "Functional characterization of rat chemokine macrophage inflammatory protein-2, " *Inflammation*, 19(1): 133–142, 1995.

Fujio, Evarts, Hu, Marsden, and Thorgeirsson, "Expression of stem cell factor and its receptor, c-kit, during liver regeneration from putative stem cells in adult rat," *Lab. Invest.*, 70:511–516, 1994.

Galli, Zsebo, and Geissler, "The kit ligand, stem cell factor," *Adv. Immunol.*, 55:1–96, 1994.

Ghosh-Choudhury, G. and Graham, F. L. *Biochem. Biophys. Res. Comm.*, 147:964–973, 1987.

Glantz, "Alternatives to analysis of variance and the t test based on ranks," *In: Primer of Biostatistics*, Glantz S A, New York N.Y.: McGraw-Hill Book Company, Inc., pp. 287–331, 1987.

Gluzman, Reichl, and Solnick, in: *Eukaryotic Viral Vectors* (Gluzman, Y., Ed.) pp. 187–192, Cold Spring Harbor Press, Cold Spring Harbor, N.Y., 1982.

Greenbaum, Li, Cressman, Peng, Ciliberto, Poli, Taub, "CCAAT enhancer-binding protein b is required for normal hepatocyte proliferation in mice sfter partial hepatectomy," *J. Clin. Invest.*, 102:996–1007, 1998.

Greenberger et al., "Neutralization of macrophage inflammatory protein-2 attenuates neutrophil recruitment and bacterial clearance in murine Klebsiella pneumonia," *J. Infect. Dis.*, 173(1):159–165, 1996.

Haskill et al., *Proc. Natl. Acad. Sci. USA*, 87:7732–7736, 1990.

Hendricks-Taylor and Darlington, *Nucleic Acid Res.*, 23:4726–4733, 1995.

Herbert, Vitangcol, Baker, "Scanning mutagenesis of interleukin-8 identifies a cluster of residues required for receptor binding," *J. Biol. Chem.*, 266:18989–18994, 1991.

Heubi, Barbacci, Zimmerman, "Therapeutic misadventures with acetaminophen:
hepatoxicity after multiple doses in children," *J. Pediatr.*, 132(1):22–27, 1998.

Higgins and Anderson, "Experimental pathology of the liver; restoration of the liver of the white rat following partial surgical removal," *Arch. Path.*, 12:186–202, 1931.

Hoffman, Rosen, Ljubimova, Sher, Podesta, Demetriou, Makowka, "Hepatic regeneration: current concepts and clinical implications," *Sem. Liv. Dis.*, 14:190–210, 1994.

Hogaboam et al., "Therapeutic effects of interleukin-4 gene transfer in experimental inflammatory bowel disease," *J. Clin. Invest.*, 100:2766–2776, 1997.

Hogaboam, Gallinat, Bone-Larson, Chensue, Lukacs, Stieter, Kunkel, "Collagen deposition in a non-fibrotic lung granuloma model after nitric oxide inhibition," *Am. J. Path.*, 153:1861–1872, 1998.

Hogaboam, Bone-Larson, Steinhauser, Lukacs, Colletti, Simpson, Strieter, Kunkel, "Novel CXCR2-dependent liver regenerative qualities of ELR-containing CXC chemokines," *FASEB J.*, 13:1565–1574, 1999a.

Hogaboam, Bone-Larson, Lipinski, Lukacs, Chensue, Strieter, Kunkel, "Differential monocyte chemoattractanat protein-1 and chemokine receptor 2 expression by murine lung fibroblasts derived from Th1- and Th2-type pulmonary granuloma models," *J. Immunol.* 163, 2193–2201. 1999b.

Huang, Chan, Wu, Pai, Chao, Lee, "Serum levels of interleukin-8 in alcoholic liver disease: relationship with disease stage, biochemical parameters and survival," *J. Hepatol.*, 24:377–384, 1996.

Huard et al., "The route of administration is a major determinant of the transduction efficiency of rat tissues by adenoviral recombinants," *Gene Ther.*, 2(2): 107–15, 1995.

Iida and Grotendorst, *Molecular and Cellular Biology*, 10(10):5596–5599, 1990.

Jaeschke, "Chemokines, neutrophils, and inflammatory liver injury", *Shock*, 6(6):403–404, 1996.

Jiang and Hiscox, "Hepatocyte growth factor/scatter factor, a cytokine playing multiple and converse roles," *Histol. Histopathol.*, 12:537–555, 1997.

Karlsson, Van Doren, Schweiger, Nienhuis, and Gluzman, *EMBO J.*, 5, 2377–2385, 1986.

Kay and Fausto, "Liver regeneration: prospects for therapy based on new technologies," *Mol. Med. Today*, 3(3) :108–115, 1997.

Kay et al., "Transient immunomodulation with anti-CD40 ligand antibody and CTLA4Ig enhances persistence and secondary adenovirus-mediated gene transfer into mouse liver," *Proc. Natl. Acad. Sci. USA*, 94(9):4686–4691, 1997.

Khoruts, Stahnke, McClain, Logan, Allen, "Circulating tumor necrosis factor, interleukin-1, and interleukin-6 concentrations in chronic alcoholic patients," *Hepatology*, 13:267–276, 1991.

Kobayashi, Narumi, Tamatani, Lane, Miyano, "Serum IFN-inducible protein-10: a new clinical prognostic predictor of hepatocyte death in biliary atresia," *J. Pediatr Surg.*, 34:308–311, 1999.

Koch, Polverini, Kunkel, Harlow, DiPietro, Elner, Elner, Streiter, "Interleukin-8 (IL-8) as a macrophage-derived mediator of angiogenesis," *Science*, 258:1798–1801, 1992.

Kubo, Yasunaga, Masuhara, Terai, Nakamura, Okita, "Hepatocyte proliferation induced in rats by lead nitrate is suppressed by several tumor necrosis factor-α inhibitors," *Hepatology*, 23:104–114, 1996.

Kulke, Bornscheuer, Schluter, Bartels, Rowert, Sticherling, Christophers, "The CXC receptor 2 is overexpressed in psoriatic epidermis," *J. Invest. Dermatol.*, 110(1):90–94, 1998.

Kwan, Bartle, Walker, "Abnormal serum transaminases following therapeutic doses of acetaminophen in the absence of known risk factors," *Dig. Dis. Sci.*, 40(9):1951–1655, 1995.

Kyte and Doolittle, "A simple method for displaying the hydropathic character of a protein," *J. Mol. Biol.*, 157(1) :105–132, 1982.

Lee, Cacalano, Camerato, Toy, Moore, Wood, "Chemokine binding and activities mediated by the mouse IL-8 receptor," *J. Immunol.*, 155:2158–2164, 1995.

Leigh, Khan, Hancock, and Knox, "Stem cell factor enhances the survival of murine intestinal stem cells after photon irradiation," *Radiat. Res.*, 142:12–15, 1995.

Lentsch, Yoshidome, Cheadle, Miller, Edwards, "Chemokine involvement in hepatic ischemia/reperfusion injury in mice: roles for macrophage inflammatory protein-2 and KC [corrected and republished article originally printed in *Hepatology* February;27(2): 507–12, 1998,]" *Hepatology*, 27:1172–1177, 1998.

Liebmann, DeLuca, Epstein, Steinberg, Morstyn, and Mitchell, "Protection from lethal irradiation by the combination of stem cell factor and tempol," *Radiat. Res.*, 137:400–404, 1994.

Lindley et al., *Proc. Natl. Acad. Sci. USA*, 85:9199–9203, 1988.

Lores Arnaiz et al., "Oxidative stress by acute acetaminophen administration in mouse liver," *Free Radic. Biol. Med.*, 19(3):303–310, 1995.

Louis et al., "Hepatoprotective role of interleukin 10 in galactosamine/lipopolysaccharide mouse liver injury," *Gastroenterology*, 112(3):935–942, 1997.

Lukacs, Strieter, Lincoln, Brownell, Pullen, Schock, Chensue, Taub, and Kunkel, "Stem cell factor (c-kit ligand) influences eosinophil recruitment and histamine levels in allergic airway inflammation," *J. Immunol.* 156 (10):3945–51, 1996.

Luster et al., *Nature*, 315:672–676, 1985.

Luster et. al., *Proc. Natl. Acad Sci. USA*, 84:2868–2871, 1987.

Luster and Ravetch, *J. Exp. Med.*, 166:1084–1097, 1987a.

Luster and Ravetch, "Genomic characterization of a gamma-interferon-inducible gene (IP-10) and identification of an interferon-inducible hypersensitive site," *Mol. Cell. Biol.*, 7:3723–31, 1987b.

Maher, Scott, Burton, *Hepatology*, 22(4,Pt.2):288A, #725, 1995.

Maione, Gray, Petro, Hunt, Donner, Bauer, Carson, Sharpe, "Inhibition of angiogenesis by recombinant human platelet factor-4," *Science*, 247:77–79, 1990.

Makin and Williams, "Acetaminophen-induced hepatotoxicity: predisposing factors and treatments," *Adv. Intern. Med.*, 42:453–483, 1997.

Manautou, Tveit, Hoivik, Khairallah, Cohen, "Protection by clofibrate against acetaminophen hepatotoxicity in male CD-1 mice is associated with an early increase in biliary concentration of acetaminophen-glutathione adducts," *Toxicol. Appl. Pharmacol.*, 140(1):30–38, 1996.

Martins-Green and Bissell, *J. Cell Biol.*, 110:581–595, 1990.

Martins-Green et al., *Cell Regulation*, 2:739–752, 1991.

Maruyama, Harada, Kurokawa, Kobayashi, Nonami, Nakao, Takagi, "Duration of liver ischemia and hepatic regeneration after hepatectomy in rats," *J. Surg. Res.*, 58:290–294, 1995.

Matsushima and Oppenheim, "Interleukin-8 and MCAF: novel inflammatory cytokines inducible by IL-1 and TNF," *Cytokine*, 1:2–13, 1989.

Matsushima et al., "Molecular cloning of a human monocyte-derived neutrophil chemotactic factor (MDNCF) and the induction of MDNCF mRNA by interleukin-1 and tumor necrosis factor," *J. Exp. Med.*, 167:1883–93, 1988.

Mawet, Shiratori, Hikiba, Takada, Yoshida, Okano, Komatsu, Matsumura, Niwa, Omata, "Cytokine-induced neutrophil chemoattractant release from hepatocytes is modulated by Kupffer cells," *Hepatology*, 23:353–358, 1996.

McGrory, Bautista, and Graham, Virol., 163, 614–617, 1988.

Michel, Kemeny, Peter, Beetz, Ried, Arenberger, Ruzicka, "Interleukin-8 receptor-mediated chemotaxis of normal human epidermal cells," *FEBS Letters*, 305:241–243, 1992.

Miller and Krangel, "Biology and biochemistry of the chemokines: a family of chemotactic and inflammatory cytokines," *Crit. Rev. Immunol.*, 12:17–46, 1992.

Modi et. al., *Hu. Genet*, 84:185–187, 1990.

Murphy, Swartz, Watkins, "Severe acetaminophen toxicity in a patient receiving isoniazid," *Ann. Intern. Med.*, 113:99–800, 1990.

Mukaidaet. al., *J. Immunol*, 143:1366–1371, 1989.

Muruve, Barnes, Stillman, Libermann, "Adenoviral gene therapy leads to rapid induction of multiple chemokines and acute neutrophil-dependent hepatic injury in vivo," *Hum Gene Ther.*, 10:965–976, 1999.

Mutimer, Ayres, Neuberger, Davies, Holguin, Buckels, "Serious paracetamol poisoning and the results of liver transplantation," *Gut.*, 35:809–814, 1994.

Nagy, Bisgaard, Thorgeirsson, "Expression of hepatic transcription factors during liver development and oval cell differentiation," *J. Cell. Biol.*, 126:223–233, 1994.

Nakamura, Tomita, Ichihara, "Density-dependent growth control of adult rat hepatocytes in primary culture," *J. Biochem.*, 94:1029–1035, 1983.

Narumi, Tominaga, Tamaru, Shimai, Okumura, Nishioji, Itoh, Okanoue, "Expression of IFN-inducible protein-10 in chronic hepatitis," *J. Immunol.*, 158:5536–5544, 1997.

Nielsen et al., "Recombinant E1-deleted adenovirus-mediated gene therapy for cancer: efficacy of studies with p53 tumor suppressor gene and liver histology in tumor xenograft models," *Hum. Gen. Ther.*, 9:681–694, 1998.

Omori, Omori, Evarts, Termoto, and Thorgeirsson, "Coexpression of flt-3 ligand/flt-3 and SCF/c-kit signal transduction system in bile-duct-ligated SI and W mice," *Am. J. Pathol.*, 150:1179–1187, 1997.

Oppenheim, Zachariae, Mukaida, Matsushima, "Properties of the novel proinflammatory supergene "intercrine" cytokine family," *Ann. Rev. Immunol.*, 9:617–648, 1991.

Papadimitriou, Topp, Serve, Oelmann, Koenigsmann, Maurer, Oberberg, Reufi, Thiel, and Berdel, "Recombinant human stem cell factor does exert minor stimulation of growth in small cell lung cancer and melanoma cell lines," *Eur. J. Cance.*, 31:2371–2378, 1995.

Peeters et al., "Adenovirus-mediated hepatic gene transfer in mice: comparison of intravascular and biliary administration," *Hum. Gene Ther.*, 7(14):1693–1699, 1996.

Pessayre et al., "Effect of fasting on metabolite-mediated hepatotoxicity in the rat," *Gastroenterology*, 77:264–271, 1979.

Power et. al., "Cloning of a full-length cDNA encoding the neutrophil-activating peptide ENA-78 from human platelets," *Gene*, 151(1–2):333–334, 1994.

Prescott and Critchley, "The treatment of acetominophen poisoning," *Annu. Rev. Pharacol. Toxicol.*, 23:87–101, 1983.

Prescott, "Liver damage with non-narcotic analgesics," *Med. Toxicol.*, 1:44–56, 1983.

Proost et al., "Human and bovine granulocyte chemotactic protein-2: complete amino acid sequence and functional characterization as chemokines," *Biochemistry*, 32(38):10170–7, 1993.

Rai, Yang, McClain, Karp, Klein, Diehl, "Kupffer cell depletion by gadolinium chloride enhances liver regeneration after partial hepatectomy in rats," *Am. J. Physiol.*, 270:G909–G918, 1996.

Rai, Loffreda, Karp, Yang, Lin, Diehl, "Kupffer cell depletion abolishes induction of interleukin-10 and permits sustained over-expression of tumor necrosis factor alpha messenger RNA in the regenerating rat liver," *Hepatology*, 25:889–895, 1997.

Rao, Yukawa, Omori, Thorgeirsson, and Reddy, "Expression of transcription factors and stem cell factor precedes hepatocyte differentiation in rat pancreas," *Gene Expr.*, 6:15–22, 1996.

Raper and Wilson, "Gene therapy for human liver disease," *Prog. Liver Dis.*, 13:201–230, 1995.

Renic et al., "The effect of interleukin-1 alpha on acetaminophen-induced hepatotoxicity," *Cytokine*, 5:192–197, 1993.

Richmond et al., *EMBO J.*, 7:2025–2033, 1988.

Ricotti, Fagioli, Garelli, Linari, Crescenzio, Horenstein, Pistamiglio, Vai, Berger, Montezemolo, Madon, and Basso, "c-kit is expressed in soft tissue sarcoma of neuroectodermic origin and its ligand prevents apoptosis of neoplastic cells," *Blood*, 91:2397–2405, 1998.

Riordan and Williams, "Cause and prognosis in acute liver failure," *Liver Transplantation and Surgery*, 5:86–89, 1999.

Rosen, Shackleton, Martin, "Indications for and timing of liver transplantation," *Med. Clin. North Am.*, 80:1069–1102, 1996.

Rosenfeld, Siegfried, Yoshimura, Yoneyama, Fukayama, Stier, Pääkkö, Gilardi, Stratford-Perricaudet, Perricaudet, Jallat, Pavirani, Lecocq, and Crystal, *Science*, 252, 431–434, 1991.

Rosenfeld, Yoshimura, Trapnell, Yoneyama, Rosenthal, Dalemans, Fukayama, Bargon, Stier, Stratford-Perricaudet, Perricaudet, Guggino, Pavirani, Lecocq, and Crystal, *Cell*, 68, 143–155, 1992.

Sanchez et al., "CXC chemokines suppress proliferation of myeloid progenitor cells by activation of the CXC chemokine receptor 2," *J. Immunol.*, 160(2):906–910, 1998.

Satoh, Adachi, Suda, Yamazaki, Mizuno, "TNF-driven inflammation during mouse liver regeneration after partial hepatectomy and its role in growth regulation of liver," *Mol. Biother.*, 3:136–147, 1991.

Schiodt, Attilasoy, Shakil, Schiff, Caldwell, Kowdley, Stribling, Crippin, Flamm, Somberg, Rosen, McCashland, Hay, Lee, Group, t. A. L. F. S., "Etiology and outcome for 295 patients with acute liver failure in the United States," *Liver Transplant. Surg.*, 5:29–34, 1999.

Schmid and Weissmann, *The Journal of Immunology*, 139 (1):250–256, 1987.

Sheron, Bird, Koskinas, Portmann, Ceska, Lindley, "Circulating and tissue levels of neutrophil chemotaxin interleukin-8 are elevated in severe acute alcoholic hepatitis, and tissue levels correlate with neutrophil infiltration," *Hepatology*, 18:41–46, 1993.

Sherr, "Cancer cell cycles," *Science*, 274:1672–1677, 1996.

Shimoda, Begum, Shibuta, Mori, Bonkovsky, Banner, Barnard, "Interleukin-8 and hIRH (SDF1-α/PBSF) mRNA expression and histological activity index in patients with chronic hepatitis C," *Hepatology*, 28:108–115, 1998.

Soriano, Kang, Finegold, Hicks, Wang, Harrison, Darlington, "Lack of C/EBP α gene expression results in increased DNA synthesis and an increased frequency of immortalization of freshly isolated mice hepatocytes," *Hepatology*, 27:392–401, 1998.

Sprenger, Kaufmann, Garn, Lahme, Gemsa, Gressner, "Induction of neutrophil-attracting chemokines in transforming rat hepatic stellate cells," *Gastroenterology*, 113 (1):277–285, 1997.

Stratford-Perricaudet, Levrero, Chasse, Perricaudet, and Briand, *Hum. Gene Ther.*, 1, 241–256, 1992.

Stratford-Perricaudet, Makeh, Perricaudet, and Briand, *J. Clin. Invest.*, 90, 626–630, 1992.

Strieter, Kunkel, Burdick, Lincoln, Walz, "The detection of a novel neutrophil-activating peptide (ENA-78) using a sensitive ELISA," *Immunol. Invest.*, 21:589–96, 1992.

Strieter, Lukacs, Standiford, Kunkel, "Cytokines and lung inflammation," *Thorax*, 48:765–769, 1993.

Strieter, Polverini, Kunkel, Arenberg, Burdick, Kasper, Dzuiba, VanDamme, Walz, Marriott, "The functional role of the ELR motif in CXC chemokine-mediate angiogenesis," *J. Biol. Chem.*, 270:27348–27357, 1995a.

Strieter, Polverini, Arenberg, Kunkel, "The role of CXC chemokines as regulators of angiogenesis," *Shock*, 4:155–160, 1995b.

Strieter, Standiford, Huffnagle, Colletti, Lukacs, Kunkel, "'The good, the bad, and the ugly.' The role of chemokines in models of human disease," *J. Immunol.*, 156(10) :3583–3586, 1996.

Sullivan et al., "Liver-directed gene transfer in non-human primates," *Hum. Gene Ther.*, 8(10):1195–1206, 1997.

Takada, Mawet, Shiratori, Hikiba, Nakata, Yoshida, Okano, Kamii, Omata, "Chemotactic factors released from hepatocytes exposed to acetaminophen," *Dig. Dis. Sci.*, 40:1831–1836, 1995.

Taub, Greenbaum, Peng, "Transcriptional regulatory signals define cytokine-dependent and -independent pathways in liver tegeneration," *Semin. Liv. Dis.*, 19:117–127, 1999.

Thomsen, Stenberg, Goins, and Stinski, *Proc. Natl. Acad. Sci. USA*, 81, 659–663, 1984.

Thornton, Strieter, Lindley, Baggiolini, Kunkel, "Cytokine-induced gene expression of a neutrophil chemotactic factor/IL-8 in human hepatocytes," *J. Immunol.*, 144:2609–2613, 1990.

Thornton, Ham, Kunkel, "Kupffer cell-derived cytokines induce synthesis of a leukocyte chemotactic peptide, interleukin-8, in human hepatoma and primary hepatocyte cultures," *Hepatology*, 14:1–11, 1991.

Tiggelman et al., "Interleukin-6 production by human liver (myo)fibroblasts in culture. Evidence for a regulatory role of LPS, IL-I beta and TNF alpha," *J. Hepatol.*, 23(3) :295–306, 1995.

Timens and Kamps, "Hemopoiesis in human fetal and embryonic liver," *Micros. Res. Tech.*, 39:387–397, 1997.

Trautwein, Caelles, van der Geer, Hunter, Karin, Chojkier, "Transactivation by NF-IL6/LAP is enhanced by phosphorylation of its activation domain," *Nature*, 364:544–547, 1993.

Trautwein, Rakiemann, Pietrangelo, Plumpe, Montosi, Manns, "C/EBP-b/LAP controls the down-regulation of albumin gene transcription during liver regeneration," *J. Biol. Chem.*, 271:22262–22270, 1996a.

Trautwein, Rakemann, Niehof, Rose-John, Mannus, "APRF, increased binding and target gene activation during liver regeneration," *Gastroenterology*, 110:28, 1996.

Trautwein et al., "Concanavalin A-induced liver injury triggers hepatocyte proliferation," *J. Clin. Invest.*, 101:1960–1969, 1998.

Turner, Zsebo, Martin, Jacobsen, Bennett, and Broudy, "Nonhematopoietic tumor cell lines express stem cell factor and display c-kit receptors," *Blood*, 80:374–381, 1992.

Vickers et al., "In vivo gene transfer to the human biliary tract," *Gene Ther.*, 3(9):825–828, 1996.

Walz, Burgener, Car, Baggiolini, Kunkel, Strieter, "Structure and neutrophil-activating properties of a novel inflammatory peptide (ENA-78) with homology to interleukin-8," *J. Exp. Med.*, 174:1355–1362, 1991.

Watkins, Condreay, Huber, Jacombs, Adams, *Cancer Res.*, 56:1063–1067, 1996.

Weinbren and Hadjis, "Compensatory hyperplasia of the liver," In: *Surgery of the Liver and Biliary Tract*, Blumgart LH (ed), United Kingdom: Churchill Livingstone, pp. 51–54, 1990.

Wenger et. al., *Blood*, 73:1498-, 1989.

Wershil, Tsai, Geissler, Zsebo, and Galli, "The rat c-kit ligand, stem cell factor, induces c-kit receptor-dependent mouse mast cell activation in vivo. Evidence that signaling through the c-kit receptor can induce expression of cellular function," *J. Exp. Med.*, 175:245–255, 1992.

Whitcomb and Block, "Association of acetaminophen hepatotoxicity with fasting and ethanol use," *JAMA*, 272(23):1845–1850, 1994.

Wigmore, Fearon, Maingay, Lai, Ross, "Interleukin-8 can mediate acute-phase protein production by isolated human hepatocytes," *Am. J. Physiol.*, 273:E720–726, 1997.

Williams, "Classification, etiology, and considerations of outcome in acute liver failure," *Semin. Liver Dis.*, 16:343–348.

Yamada, Kirillova, Peschon, Fausto, "Initiation of liver growth by tumor necrosis factor: deficient liver regeneration in mice lacking type I tumor necrosis factor receptor," *Proc. NatL. Acad. Sci. USA*, 94:1441–1446, 1997.

Yang et al., "Immune responses to viral antigens versus transgene product in the elimination of recombinant adenovirus-infected hepatocytes in vivo," *Gene Ther.*, 3(2):137–144, 1996.

Yang et al., "Transient subversion of CD40 ligand function diminishes immune responses to adenovirus vectors in mouse liver and lung tissues," *J. Virol.*, 70(9):6370–6377, 1996.

Yoshidome, Lentsch, Miller, Edwards, "Roles of MIP-2 and KC in hepatic ischemia/reperfusion injury in mice," *FASEB J.*, 11(3):A295, #1712, 1997.

Zhang, Sun, Samols, Kushner, "STAT3 participates in transcriptional activation of the C-reactive protein gene by interleukin-6," *J. Biol. Chem.*, 271:9503–9, 1996.

Zhong, Wen, Darnell, "Stat3: a Stat family member activated by tyrosine phosphorylation in response to epidermal growth factor and interleukin-6," *Science*, 264:95–98, 1994.

Zsebo, Smith, Hartley, Greenblatt, Cooke, Rich, and McNiece, "Radioprotection of mice by recombinant rat stem cell factor," *Proc. Nat. Acad. Sci. USA*, 89:9464–9468, 1992.

What is claimed is:

1. A method of stimulating hepatocyte proliferation, comprising providing to a hepatocyte at least a first composition comprising at least a first CXC chemokine that activates the CXC chemokine receptor 2 (CXCR2) in an amount effective to stimulate hepatocyte proliferation.

2. The method of claim 1, wherein said composition is provided to said hepatocyte in vivo by administering said composition to an animal.

3. The method of claim 1, wherein said composition comprises at least a first ELR-containing CXC chemokine that binds to and activates the CXCR2 receptor.

4. The method of claim 3, wherein said composition comprises the ELR-containing CXC chemokine MIP-2, ENA-78 or IL-8.

5. The method of claim 4, wherein said composition comprises the ELR-containing CXC chemokine MIP-2.

6. The method of claim 4, wherein said composition comprises the ELR-containing CXC chemokine ENA-78.

7. The method of claim 4, wherein said composition comprises the ELR-containing CXC chemokine IL-8.

8. A method of stimulating hepatic regeneration, comprising providing to an animal an amount of at least a first CXC chemokine composition effective to activate the CXCR2 receptor, thereby stimulating hepatic regeneration in said animal.

9. The method of claim 8, wherein said composition comprises the ELR-containing CXC chemokine MIP-2.

10. The method of claim 8, wherein said composition comprises the ELR-containing CXC chemokine ENA-78.

11. The method of claim 8, wherein said composition comprises the ELR-containing CXC chemokine IL-8.

12. The method of claim 8, wherein said animal has liver damage associated with surgical intervention.

13. The method of claim 8, wherein said animal has liver damage associated with excess acetaminophen ingestion.

14. The method of claim 8, wherein said animal has liver damage associated with adenovirus infection of liver cells or adenovirus-mediated gene therapy.

15. The method of claim 8, wherein said animal is a human patient.

16. A method of treating an animal with liver damage, comprising administering to said animal at least a first composition comprising at least a first CXC chemokine that activates the CXC chemokine receptor 2 (CXCR2); wherein said composition is administered in an amount and for a time effective to treat said liver damage in said animal.

17. The method of claim 16, wherein said composition comprises at least a first ELR-containing CXC chemokine that binds to and activates the CXCR2 receptor.

18. The method of claim 17, wherein said composition comprises the ELR-containing CXC chemokine GCP-2 (granulocyte chemotactic protein-2), NAP-2 (neutrophil activating peptide-2), CTAP-III (connective tissue activating protein-III), βTG (β-thromboglobulin), GRO-α (growth related oncogene peptide-α), GRO-β (growth related oncogene peptide-β) or GRO-γ (growth related oncogene peptide-γ).

19. The method of claim 16, wherein said composition comprises at least one of MIP-2, ENA-78 or IL-8.

20. The method of claim 19, wherein said composition comprises the ELR-containing CXC chemokine MIP-2 (macrophage inflammatory protein-2).

21. The method of claim 19, wherein said composition comprises the ELR-containing CXC chemokine ENA-78 (epithelial neutrophil activating protein-78).

22. The method of claim 19, wherein said composition comprises the ELR-containing CXC chemokine IL-8 (interleukin-8).

23. The method of claim 16, wherein said composition comprises at least a first and second CXC chemokine.

24. The method of claim 16, wherein said composition comprises at least a first CXC chemokine protein.

25. The method of claim 16, wherein said composition further comprises at least a first hepatoproliferative agent other than a CXC chemokine in an amount effective to further stimulate hepatocyte proliferation in said animal.

26. The method of claim 25, wherein said composition further comprises the hepatoproliferative agent, NAC (N-acetyl-cysteine), HGF (hepatocyte growth factor), stem cell factor (SCF), TNF-α (tumor necrosis factor-α) or IL-6 (interleukin-6).

27. The method of claim 16, wherein said liver damage is associated with exposure to alcohol, a hepatotoxic drug, an infectious agent or surgical intervention.

28. The method of claim 16, wherein said liver damage is associated with excess acetaminophen ingestion.

29. The method of claim 16, wherein said liver damage is associated with adenovirus infection of liver cells.

30. The method of claim 29, wherein said liver damage is associated with adenovirus-mediated gene therapy.

31. The method of claim 16, wherein said liver damage is chronic liver damage and said composition is administered to said animal over an extended biologically effective time period.

32. The method of claim 16, wherein said liver damage is acute liver damage and at least a first dose of said composition is administered to said animal within a biologically effective time period after onset of said liver damage.

33. The method of claim 32, wherein said liver damage is acute liver damage and at least a first dose of said composition is administered to said animal at a time between about ten minutes and about 72 hours after onset of said liver damage.

34. The method of claim 32, wherein said liver damage is acute liver damage and at least a first dose of said composition is administered to said animal at a time between about ten hours and about 72 hours after onset of said liver damage.

35. The method of claim 16, claim wherein said animal is a human patient.

36. The method of claim 16, wherein said composition further comprises a biologically effective amount of at least a first hepatoproliferative agent other than a CXC chemokine.

37. A method of treating an animal with liver damage, comprising administering to said animal at least a first ELR-containing CXC chemokine in an amount effective to treat liver damage in said animal.

38. A method of timely treating a patient with acute liver damage, comprising administering to said patient an amount of at least a first CXC chemokine composition effective to treat acute liver damage in said patient; wherein said composition comprises at least a first CXC chemokine that activates the CXC chemokine receptor 2 (CXCR2) in said patient and wherein said composition is administered at a time between about ten hours and about 72 hours after the onset of said liver damage.

39. A method of treating acetaminophen-induced liver damage, comprising administering to a patient with acetaminophen-induced liver damage an amount of at least a first CXC chemokine composition effective to promote liver cell proliferation and liver regeneration in said patient; wherein said CXC chemokine composition comprises at least a first CXC chemokine that activates the CXC chemokine receptor 2 (CXCR2).

40. The method of claim 39, wherein said patient presents with fulminant hepatic failure outside the therapeutic window for treatment with NAC (N-acetyl-cysteine).

41. A method of treating an animal with liver damage, comprising administering to said animal an amount of at least a first CXC chemokine composition effective to activate the CXCR2 receptor in said animal, thereby stimulating hepatic regeneration and treating said liver damage in said animal.

42. A method of treating an animal with liver damage associated with excess acetaminophen or surgical intervention, comprising administering to said animal an amount of at least a first CXC chemokine composition effective to activate the CXCR2 receptor in said animal, thereby stimulating hepatic regeneration and treating said liver damage in said animal.

43. A method of treating an animal with liver damage, comprising administering to said animal an amount of at least a first ELR-containing CXC chemokine effective to stimulate hepatic regeneration and treat said liver damage in said animal.

44. A method of stimulating hepatocyte proliferation, comprising providing to a hepatocyte a biologically effective amount of at least a first composition comprising at least a first CXC chemokine that activates the CXC chemokine receptor 2 (CXCR2).

45. A method of treating an animal with liver damage, comprising administering to said animal a therapeutically effective amount of at least a first composition comprising at least a first CXC chemokine that activates the CXC chemokine receptor 2 (CXCR2) in said animal.

46. A method of treating an animal with liver damage, comprising administering to said animal a therapeutically effective amount of at least a first ELR-containing CXC chemokine.

47. A method of timely treating a patient with acute liver damage, comprising administering to said patient a therapeutically effective amount of at least a first CXC chemokine composition at a time between about ten hours and about 72 hours after the onset of said liver damage; wherein said composition comprises at least a first CXC chemokine that activates the CXC chemokine receptor 2 (CXCR2) in said patient.

48. A method of treating acetaminophen-induced liver damage, comprising administering to a patient with acetaminophen-induced liver damage a therapeutically effective amount of at least a first CXC chemokine composition comprising at least a first CXC chemokine that activates the CXC chemokine receptor 2 (CXCR2), thereby promoting liver cell proliferation and liver regeneration in said patient.

49. A method of stimulating hepatocyte proliferation, comprising providing to a hepatocyte at least a first composition comprising at least a first ELR-containing CXC chemokine selected from the group consisting of MIP-2, ENA-78 and IL-8 in an amount effective to stimulate hepatocyte proliferation.

50. A method of stimulating hepatic regeneration, comprising providing to an animal at least a first ELR-containing CXC chemokine selected from the group consisting of MIP-2, ENA-78 and IL-8 in an amount effective to activate the CXCR2 receptor, thereby stimulating hepatic regeneration in said animal.

51. A method of treating an animal with liver damage, comprising administering to said' animal at least a first composition comprising at least a first ELR-containing CXC chemokine selected from the group consisting of MIP-2, ENA-78 and IL-8; wherein said composition is administered in an amount and for a time effective to treat said liver damage in said animal.

* * * * *